United States Patent
Arend et al.

(10) Patent No.: US 8,269,008 B2
(45) Date of Patent: Sep. 18, 2012

(54) OXAZOLOPYRIDINE AND ISOXAZOLOPYRIDINE DERIVATIVES FOR USE IN THE TREATMENT OF HIF-MEDIATED CONDITIONS

(75) Inventors: Michael P. Arend, Foster City, CA (US); Heng Cheng, Foster City, CA (US); Lee A. Flippin, Woodside, CA (US); Danny Ng, Daly City, CA (US); Eric D. Turtle, Belmont, CA (US); Min Wu, Sunnyvale, CA (US)

(73) Assignee: FibroGen, Inc., San Francisco, CA (US)

( * ) Notice: Subject to any disclaimer, the term of this patent is extended or adjusted under 35 U.S.C. 154(b) by 215 days.

(21) Appl. No.: 12/734,895

(22) PCT Filed: Dec. 2, 2008

(86) PCT No.: PCT/US2008/085286

§ 371 (c)(1),
(2), (4) Date: Aug. 16, 2010

(87) PCT Pub. No.: WO2009/073669

PCT Pub. Date: Jun. 11, 2009

(65) Prior Publication Data

US 2010/0303928 A1 Dec. 2, 2010

Related U.S. Application Data

(60) Provisional application No. 60/991,948, filed on Dec. 3, 2007.

(51) Int. Cl.
*C07D 221/18* (2006.01)
*C07D 221/02* (2006.01)
*C07D 221/22* (2006.01)
*A01N 43/42* (2006.01)
*A01N 43/40* (2006.01)
*A61K 31/44* (2006.01)
*A61K 31/435* (2006.01)
*A61P 25/00* (2006.01)
*A61P 3/04* (2006.01)
*C07C 63/00* (2006.01)
*C07C 65/00* (2006.01)
*C12N 9/99* (2006.01)
*C12N 9/14* (2006.01)

(52) U.S. Cl. .......... 546/116; 546/26; 546/112; 546/115; 424/94.6; 424/94.63; 435/183; 435/154; 435/195; 435/212; 514/13.5; 514/16.4; 514/17.5; 514/17.7; 514/277; 514/299; 514/302; 514/338; 514/339; 514/344; 514/345; 514/346; 514/350; 514/351; 562/400; 562/405; 562/433; 562/443

(58) Field of Classification Search .................... 546/26, 546/112, 115, 116; 514/13.5, 16.4, 17.5, 514/17.7, 277, 299, 302, 338, 339, 344, 345, 514/346, 350, 351; 562/400, 405, 433, 443; 424/94.6, 94.63; 435/183, 184, 195, 212
See application file for complete search history.

(56) References Cited

U.S. PATENT DOCUMENTS

| | | |
|---|---|---|
| 7,323,475 B2 | 1/2008 | Arend et al. |
| 7,618,940 B2 | 11/2009 | Fourney et al. |
| 7,629,357 B2 | 12/2009 | Arend et al. |
| 7,696,223 B2 | 4/2010 | Deng et al. |
| 7,713,986 B2 | 5/2010 | Seeley et al. |
| 7,863,292 B2 | 1/2011 | Arend et al. |
| 2003/0153503 A1 | 8/2003 | Klaus et al. |
| 2003/0176317 A1 | 9/2003 | Guenzler-Pukall et al. |
| 2004/0204356 A1 | 10/2004 | Guenzler-Pukall et al. |
| 2004/0235082 A1 | 11/2004 | Fourney et al. |
| 2005/0020487 A1 | 1/2005 | Klaus et al. |
| 2006/0178316 A1 | 8/2006 | Klaus et al. |
| 2006/0178317 A1 | 8/2006 | Klaus et al. |
| 2006/0183695 A1 | 8/2006 | Klaus et al. |
| 2006/0199836 A1 | 9/2006 | Turtle et al. |
| 2006/0251638 A1 | 11/2006 | Guenzler-Pukall et al. |
| 2006/0258660 A1 | 11/2006 | Guenzler-Pukall et al. |
| 2006/0258702 A1 | 11/2006 | Guenzler-Pukall et al. |
| 2006/0270699 A1 | 11/2006 | Guenzler-Pukall et al. |
| 2006/0276477 A1 | 12/2006 | Klaus et al. |
| 2007/0004627 A1 | 1/2007 | Seeley et al. |
| 2007/0155784 A1 | 7/2007 | Arend et al. |
| 2007/0292433 A1 | 12/2007 | Seeley et al. |
| 2007/0293575 A1 | 12/2007 | Seeley et al. |
| 2007/0298104 A1 | 12/2007 | Arend et al. |
| 2008/0293763 A1 | 11/2008 | Arend et al. |
| 2010/0047367 A1 | 2/2010 | Deng et al. |
| 2010/0303928 A1 | 12/2010 | Arend et al. |
| 2010/0330199 A1 | 12/2010 | Zhou et al. |
| 2010/0331400 A1 | 12/2010 | Ho et al. |

FOREIGN PATENT DOCUMENTS

| | | |
|---|---|---|
| WO | WO 03/053997 A2 | 7/2003 |
| WO | WO 2004/052284 A2 | 6/2004 |
| WO | WO 2004/052285 A2 | 6/2004 |
| WO | WO 2004/108121 A1 | 12/2004 |
| WO | WO 2004/108681 A1 | 12/2004 |

(Continued)

OTHER PUBLICATIONS

U.S. Appl. No. 13/042,281, filed Mar. 7, 2011, Arend et al.

*Primary Examiner* — Johann Richter
*Assistant Examiner* — Jane C Oswecki
(74) *Attorney, Agent, or Firm* — Foley & Lardner LLP

(57) ABSTRACT

The present invention relates to novel compounds capable of modulating the stability and/or activity of hypoxia inducible factor (HIF) by inhibiting the activity of at least one HIF hydroxylase enzyme.

32 Claims, No Drawings

FOREIGN PATENT DOCUMENTS

| | | |
|---|---|---|
| WO | WO 2005/007192 A2 | 1/2005 |
| WO | WO 2006/094292 A2 | 9/2006 |
| WO | WO 2006/133391 A2 | 12/2006 |
| WO | WO 2006/138511 A2 | 12/2006 |
| WO | WO 2007/090068 A2 | 8/2007 |
| WO | WO 2007/115315 A2 | 10/2007 |
| WO | WO 2007/146425 A2 | 12/2007 |
| WO | WO 2007/146438 A1 | 12/2007 |
| WO | WO 2009/073669 A1 | 6/2009 |
| WO | WO 2009/089547 A1 | 7/2009 |
| WO | WO 2009/100250 A1 | 8/2009 |
| WO | WO 2010/022240 A1 | 2/2010 |
| WO | WO 2010/056767 A1 | 5/2010 |

OXAZOLOPYRIDINE AND ISOXAZOLOPYRIDINE DERIVATIVES FOR USE IN THE TREATMENT OF HIF-MEDIATED CONDITIONS

This application is a National Phase application under 35 U.S.C. §371 of PCT Application PCT/US2008/085286, filed Dec. 2, 2008, which claims benefit from U.S. Provisional Application No. 60/991,948, filed Dec. 3, 2007, which are hereby incorporated by reference in their entirety.

BACKGROUND OF THE INVENTION

1. Field of the Invention

The present invention relates to novel compounds, methods, and compositions capable of decreasing HIF hydroxylase enzyme activity, thereby increasing the stability and/or activity of hypoxia inducible factor (HIF).

2. State of the Art

Hypoxia inducible factor (HIF) is a basic helix-loop-helix (bHLH) PAS (Per/Arnt/Sim) transcriptional activator that mediates changes in gene expression in response to changes in cellular oxygen concentration. HIF is a heterodimer containing an oxygen-regulated α-subunit (HIFα), and a constitutively expressed β-subunit (HIFβ/ARNT). In oxygenated (normoxic) cells, HIFα subunits are rapidly degraded by a mechanism that involves ubiquitination by the von Hippel-Lindau tumor suppressor (pVHL) E3 ligase complex. Under hypoxic conditions, HIFα is not degraded, and an active HIFα/β complex accumulates in the nucleus, and activates the expression of several genes including glycolytic enzymes, glucose transporters, erythropoietin (EPO), and vascular endothelial growth factor (VEGF). (Jiang et al. (1996) *J. Biol. Chem.* 271:17771-17778; Iliopoulus et al. (1996) *Proc. Natl. Acad. Sci. USA,* 93:10595-10599; Maxwell et al. (1999) *Nature* 399:271-275; Sutter et al. (2000) *Proc. Natl. Acad. Sci. USA* 97:4748-4753; Cockman et al. (2000) *J. Biol. Chem.* 275:25733-25741; and Tanimoto et al. (2000) *EMBO J.* 19:4298-4309.)

Levels of HIFα are elevated in most cells in response to hypoxia, and HIFα is induced in vivo when animals are subjected to anemia or hypoxia. HIFα levels rise within a few hours after the onset of hypoxia, and induce numerous beneficial cellular processes including cytoprotective effects, enhanced erythropoiesis, and physiological adaptation to ischemic or hypoxic states. Induction of HIFα is potentially beneficial in conditions such as heart attack, stroke, peripheral vascular disease, chronic ischemia, inflammation, and anemia.

HIFα levels are also increased by a number of factors that mimic hypoxia, including iron chelators such as desferrioxamine (DFO), and divalent metal salts such as $CoCl_2$. Additionally, several compounds originally identified as inhibitors of procollagen prolyl hydroxylase enzymes have been found to stabilize HIFα. Examples of such compounds can be found, e.g., in Majamaa et al. (1984) *Eur. J. Biochem.* 138: 239-245; Majamaa et al. (1985) *Biochem. J.* 229:127-133; Kivirikko, and Myllyharju (1998) *Matrix Biol.* 16:357-368; Bickel et al. (1998) *Hepatology* 28:404-411; Friedman et al. (2000) *Proc. Natl. Acad. Sci. USA* 97:4736-4741; Franklin (1991) *Biochem. Soc. Trans.* 19):812-815; and Franklin et al. (2001) *Biochem. J.* 353:333-338. Additionally, compounds that stabilize HIFα have been described in, e.g., International Publication Nos. WO 03/049686, WO 02/074981, WO 03/080566, WO 2004/108681, WO 06/094292, WO 07/038, 571, WO 07/090,068, and WO 07/103,905.

There remains a need for compounds that are effective in the treatment and prevention of conditions and disorders associated with HIF, including anemia and tissue damage caused by ischemia and/or hypoxia. Compounds are provided herein that modulate HIF and can thus be used to treat and prevent HIF-associated conditions and disorders including conditions involving anemia, ischemia, and hypoxia.

SUMMARY OF THE INVENTION

The present invention is directed to novel compounds and methods of using the compounds to modulate hydroxylation of the alpha subunit of hypoxia inducible factor.

In one aspect, there are provided compounds of Formula I:

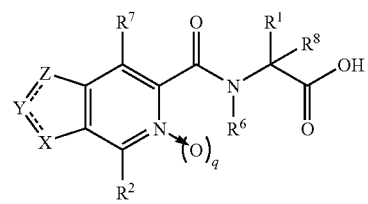

wherein q is 0 or 1;

X and Z are independently selected from the group consisting of —O—, =N—, and =C($R^3$)—; Y is =C($R^5$)— or =N—, with the proviso that at least one of the following is present
a) one of X or Z is —O— and the other is =N—, and Y is =C($R^5$)—; or
b) one of X or Z is —O— and the other is =C($R^3$)—, and Y is =N—;

$R^1$ is selected from the group consisting of hydrogen, deuterium, alkyl, and substituted alkyl;

$R^2$ is selected from the group consisting of hydrogen, halo, cyano, nitro, alkyl, substituted alkyl, alkenyl, substituted alkenyl, alkynyl, substituted alkynyl, alkoxy, substituted alkoxy, cycloalkyl, substituted cycloalkyl, cycloalkoxy, substituted cycloalkoxy, amino, substituted amino, aminoacyl, acylamino, aryl, substituted aryl, aryloxy, substituted aryloxy, heteroaryl, substituted heteroaryl, heteroaryloxy, substituted heteroaryloxy, heterocyclyl, substituted heterocyclyl, heterocyclyloxy, substituted heterocyclyloxy, alkylthio, substituted alkylthio, cycloalkylthio, substituted cycloalkylthio, arylthio, substituted arylthio, heteroarylthio, substituted heteroarylthio, heterocyclicthio, substituted heterocyclicthio, and acyl;

$R^3$ and $R^5$ are independently selected from the group consisting of hydrogen, hydroxy, cyano, halo, nitro, acyl, amino, substituted amino, acylamino, sulfonyl, substituted sulfonyl, alkyl, substituted alkyl, alkenyl, substituted alkenyl, alkynyl, substituted alkynyl, cycloalkyl, substituted cycloalkyl, cycloalkoxy, substituted cycloalkoxy, alkoxy, substituted alkoxy, aryl, substituted aryl, aryloxy, substituted aryloxy, alkylthio, substituted alkylthio, cycloalkylthio, substituted cycloalkylthio, arylthio, substituted arylthio, heteroarylthio, substituted heteroarylthio, heterocyclicthio, substituted heterocyclicthio, heterocyclic, substituted heterocyclic, heterocyclyloxy, substituted heterocyclyloxy, heteroaryl, substituted heteroaryl, heteroaryloxy, and substituted heteroaryloxy;

R[6] is selected from the group consisting of hydrogen, alkyl, and substituted alkyl;

R[7] is selected from the group consisting of hydroxy, alkoxy, substituted alkoxy, cycloalkoxy, substituted cycloalkoxy, aryloxy, substituted aryloxy, heteroaryloxy, substituted heteroaryloxy, heterocyclyloxy, substituted heterocyclyloxy, mercapto, alkylthio, substituted alkylthio, cycloalkylthio, substituted cycloalkylthio, arylthio, substituted arylthio, heteroarylthio, substituted heteroarylthio, heterocyclicthio, substituted heterocyclicthio, amino, substituted amino, and acylamino; and R[8] is selected from the group consisting of hydrogen, deuterium, and methyl;

or a pharmaceutically acceptable salt, single stereoisomer, mixture of stereoisomers, ester, or prodrug thereof.

In one aspect, there are provided compounds of Formula I(a) or I(a)':

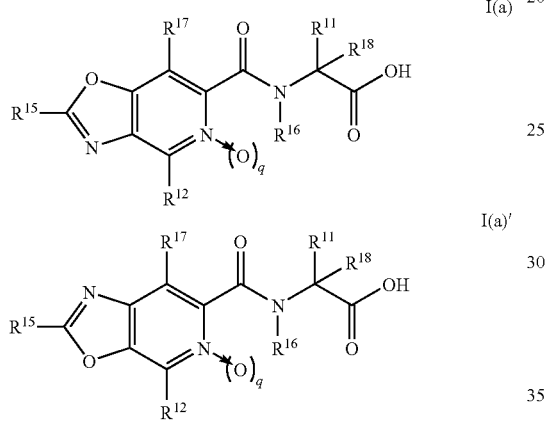

wherein
q is 0 or 1;
R[11] is selected from the group consisting of hydrogen, deuterium, alkyl, and substituted alkyl;
R[12] is selected from the group consisting of hydrogen, halo, cyano, nitro, alkyl, substituted alkyl, alkenyl, substituted alkenyl, alkynyl, substituted alkynyl, alkoxy, substituted alkoxy, cycloalkyl, substituted cycloalkyl, cycloalkoxy, substituted cycloalkoxy, amino, substituted amino, aminoacyl, acylamino, aryl, substituted aryl, aryloxy, substituted aryloxy, heteroaryl, substituted heteroaryl, heteroaryloxy, substituted heteroaryloxy, heterocyclyl, substituted heterocyclyl, heterocyclyloxy, substituted heterocyclyloxy, alkylthio, substituted alkylthio, cycloalkylthio, substituted cycloalkylthio, arylthio, substituted arylthio, heteroarylthio, substituted heteroarylthio, heterocyclicthio, substituted heterocyclicthio, and acyl;
R[15] is selected from the group consisting of hydrogen, hydroxy, cyano, halo, nitro, acyl, amino, substituted amino, acylamino, sulfonyl, substituted sulfonyl, alkyl, substituted alkyl, alkenyl, substituted alkenyl, alkynyl, substituted alkynyl, cycloalkyl, substituted cycloalkyl, cycloalkoxy, substituted cycloalkoxy, alkoxy, substituted alkoxy, aryl, substituted aryl, aryloxy, substituted aryloxy, alkylthio, substituted alkylthio, cycloalkylthio, substituted cycloalkylthio, arylthio, substituted arylthio, heteroarylthio, substituted heteroarylthio, heterocyclicthio, substituted heterocyclicthio, heterocyclyloxy, substituted heterocyclyloxy, heterocyclic, substituted heterocyclic, heteroaryl, substituted heteroaryl, heteroaryloxy, and substituted heteroaryloxy;

R[16] is selected from the group consisting of hydrogen, alkyl, and substituted alkyl;

R[17] is selected from the group consisting of hydroxy, alkoxy, substituted alkoxy, cycloalkoxy, substituted cycloalkoxy, aryloxy, substituted aryloxy, heteroaryloxy, substituted heteroaryloxy, heterocyclyloxy, substituted heterocyclyloxy, mercapto, alkylthio, substituted alkylthio, cycloalkylthio, substituted cycloalkylthio, arylthio, substituted arylthio, heteroarylthio, substituted heteroarylthio, heterocyclicthio, substituted heterocyclicthio, amino, substituted amino, and acylamino; and R[18] is selected from the group consisting of hydrogen, deuterium, and methyl;

or a pharmaceutically acceptable salt, single stereoisomer, mixture of stereoisomers, ester, or prodrug thereof.

In one aspect, there are provided compounds of Formula I(b) or I(b)':

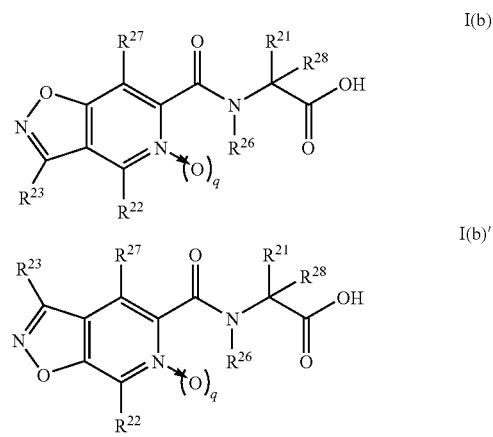

wherein
q is 0 or 1;
R[21] is selected from the group consisting of hydrogen, deuterium, alkyl, and substituted alkyl;
R[22] is selected from the group consisting of hydrogen, halo, cyano, nitro, alkyl, substituted alkyl, alkenyl, substituted alkenyl, alkynyl, substituted alkynyl, alkoxy, substituted alkoxy, cycloalkyl, substituted cycloalkyl, cycloalkoxy, substituted cycloalkoxy, amino, substituted amino, aminoacyl, acylamino, aryl, substituted aryl, aryloxy, substituted aryloxy, heteroaryl, substituted heteroaryl, heteroaryloxy, substituted heteroaryloxy, heterocyclyl, substituted heterocyclyl, heterocyclyloxy, substituted heterocyclyloxy, alkylthio, substituted alkylthio, cycloalkylthio, substituted cycloalkylthio, arylthio, substituted arylthio, heteroarylthio, substituted heteroarylthio, heterocyclicthio, substituted heterocyclicthio, and acyl;
R[23] is selected from the group consisting of hydrogen, hydroxy, cyano, halo, nitro, acyl, amino, substituted amino, acylamino, sulfonyl, substituted sulfonyl, alkyl, substituted alkyl, alkenyl, substituted alkenyl, alkynyl, substituted alkynyl, cycloalkyl, substituted cycloalkyl, cycloalkoxy, substituted cycloalkoxy, alkoxy, substituted alkoxy, aryl, substituted aryl, aryloxy, substituted aryloxy, alkylthio, substituted alkylthio, cycloalkylthio, substituted cycloalkylthio, arylthio, substituted arylthio, heteroarylthio, substituted heteroarylthio, heterocyclicthio, substituted heterocyclicthio, heterocyclyoxy, heterocyclyoxy, heterocyclic, substituted heterocyclic, heteroaryl, substituted heteroaryl, heteroaryloxy, and substituted heteroaryloxy;

$R^{26}$ is selected from the group consisting of hydrogen, alkyl, and substituted alkyl;

$R^{27}$ is selected from the group consisting of hydroxy, alkoxy, substituted alkoxy, cycloalkoxy, substituted cycloalkoxy, aryloxy, substituted aryloxy, heteroaryloxy, substituted heteroaryloxy, heterocyclyoxy, substituted heterocyclyoxy, mercapto, alkylthio, substituted alkylthio, cycloalkylthio, substituted cycloalkylthio, arylthio, substituted arylthio, heteroarylthio, substituted heteroarylthio, heterocyclicthio, substituted heterocyclicthio, amino, substituted amino, and acylamino; and $R^{28}$ is selected from the group consisting of hydrogen, deuterium, and methyl;

or a pharmaceutically acceptable salt, single stereoisomer, mixture of stereoisomers, ester, or prodrug thereof.

The invention also provides pharmaceutical compositions comprising one or more compounds of Formula I, I(a), I(a)', I(b), or I(b)' and a pharmaceutically acceptable excipient. In some embodiments, the composition further comprises at least one additional therapeutic agent. In some embodiments, the agent is selected from the group consisting of vitamin $B_{12}$, folic acid, ferrous sulfate, recombinant human erythropoietin, and an erythropoiesis stimulating agent (ESA).

The invention is also directed to methods of treating, pretreating, or delaying onset or progression of a condition associated with or mediated, at least in part, by hypoxia inducible factor (HIF), the method comprising administering to a patient a therapeutically effective amount of a compound of Formula I, I(a), I(a)', I(b), or I(b)' or a pharmaceutical composition comprising one or more compounds of Formula I, I(a), I(a)', I(b), or I(b)' and a pharmaceutically acceptable excipient. In one embodiment, the condition associated with or mediated by HIF is tissue damage associated with ischemia or hypoxia. In one aspect, the ischemia is associated with an acute event including, but not limited to, an acute event selected from the group consisting of myocardial infarction, pulmonary embolism, intestinal infarction, ischemic stroke, and renal ischemic-reperfusion injury. In another aspect, the ischemia is associated with a chronic event including, but not limited to, a chronic event selected from the group consisting of cardiac cirrhosis, transient ischemic attack, macular degeneration, chronic kidney failure, peripheral artery disease, and congestive heart failure.

The invention is also directed to methods of treating, pretreating, or delaying onset or progression of a condition associated with or mediated at least in part by erythropoietin (EPO), the method comprising administering to a patient a therapeutically effective amount of a compound of Formula I, I(a), I(a)', I(b), or I(b)' or a pharmaceutical composition comprising one or more compounds of Formula I, I(a), I(a)', I(b), or I(b)'.

The invention is also directed to methods of treating, pretreating, or delaying onset or progression of anemia, the method comprising administering to a patient a therapeutically effective amount of a compound of Formula I, I(a), I(a)', I(b), or I(b)' or a pharmaceutical composition comprising one or more compounds of Formula I, I(a), I(a)', I(b), or I(b)'.

The invention is also directed to methods of inhibiting the activity of at least one HIF hydroxylase enzyme, the method comprising bringing into contact the HIF hydroxylase enzyme and a compound of the invention. In one embodiment, the HIF hydroxylase enzyme is an asparaginyl hydroxylase such as Factor Inhibiting HIF (FIH). In another embodiment, the HIF hydroxylase enzyme is a prolyl hydroxylase including, but not limited to, a HIF prolyl hydroxylase selected from the group consisting of human EGLN1, EGLN2, or EGLN3, or an orthologous enzyme from another species.

DETAILED DESCRIPTION OF THE INVENTION

Before the present compositions, and methods are described, it is to be understood that the invention is not limited to the particular compounds, compositions, methodologies, protocols, cell lines, assays, and reagents described, as these may vary. It is also to be understood that the terminology used herein is intended to describe particular embodiments of the present invention, and is in no way intended to limit the scope of the present invention as set forth in the appended claims.

1. Compounds of the Invention

The invention is directed to compounds of Formula I:

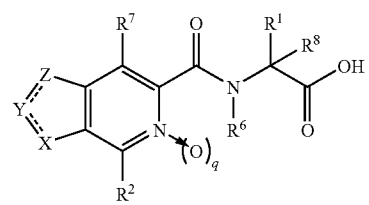

wherein q is 0 or 1;

X and Z are independently selected from the group consisting of —O—, =N—, and =C($R^3$)—; Y is =C($R^5$)— or =N—, with the proviso that at least one of the following is present
  a) one of X or Z is —O— and the other is =N—, and Y is =C($R^5$)—; or
  b) one of X or Z is —O— and the other is =C($R^3$)—, and Y is =N—;

$R^1$ is selected from the group consisting of hydrogen, deuterium, alkyl, and substituted alkyl;

$R^2$ is selected from the group consisting of hydrogen, halo, cyano, nitro, alkyl, substituted alkyl, alkenyl, substituted alkenyl, alkynyl, substituted alkynyl, alkoxy, substituted alkoxy, cycloalkyl, substituted cycloalkyl, cycloalkoxy, substituted cycloalkoxy, amino, substituted amino, aminoacyl, acylamino, aryl, substituted aryl, aryloxy, substituted aryloxy, heteroaryl, substituted heteroaryl, heteroaryloxy, substituted heteroaryloxy, heterocyclyl, substituted heterocyclyl, heterocyclyoxy, substituted heterocyclyoxy, alkylthio, substituted alkylthio, cycloalkylthio, substituted cycloalkylthio, arylthio, substituted arylthio, heteroarylthio, substituted heteroarylthio, heterocyclicthio, substituted heterocyclicthio, and acyl;

R³ and R⁵ are independently selected from the group consisting of hydrogen, hydroxy, cyano, halo, nitro, acyl, amino, substituted amino, acylamino, sulfonyl, substituted sulfonyl, alkyl, substituted alkyl, alkenyl, substituted alkenyl, alkynyl, substituted alkynyl, cycloalkyl, substituted cycloalkyl, cycloalkoxy, substituted cycloalkoxy, alkoxy, substituted alkoxy, aryl, substituted aryl, aryloxy, substituted aryloxy, alkylthio, substituted alkylthio, cycloalkylthio, substituted cycloalkylthio, arylthio, substituted arylthio, heteroarylthio, substituted heteroarylthio, heterocyclicthio, substituted heterocyclicthio, heterocyclic, substituted heterocyclic, heterocyclyloxy, substituted heterocyclyloxy, heteroaryl, substituted heteroaryl, heteroaryloxy, and substituted heteroaryloxy;

R⁶ is selected from the group consisting of hydrogen, alkyl, and substituted alkyl;

R⁷ is selected from the group consisting of hydroxy, alkoxy, substituted alkoxy, cycloalkoxy, substituted cycloalkoxy, aryloxy, substituted aryloxy, heteroaryloxy, substituted heteroaryloxy, heterocyclyloxy, substituted heterocyclyloxy, mercapto, alkylthio, substituted alkylthio, cycloalkylthio, substituted cycloalkylthio, arylthio, substituted arylthio, heteroarylthio, substituted heteroarylthio, heterocyclicthio, substituted heterocyclicthio, amino, substituted amino, and acylamino; and R⁸ is selected from the group consisting of hydrogen, deuterium, and methyl;

or a pharmaceutically acceptable salt, single stereoisomer, mixture of stereoisomers, ester, or prodrug thereof.

In certain embodiments, q is 0.

In certain embodiments, R¹ is hydrogen or alkyl. In particular embodiments, R¹ is methyl.

In certain embodiments, R² is selected from the group consisting of hydrogen, cyano, halo, amino, substituted amino, alkyl, substituted alkyl, alkynyl, substituted alkynyl, cycloalkyl, aryl, substituted aryl, heteroaryl, substituted heteroaryl, and acyl. In particular embodiments, R² is selected from hydrogen, cyano, bromo, (ethanic acid-2-yl)amino, methyl, ethyl, butyl, trifluoromethyl, pyrazol-1-ylmethyl, cyclopropyl, benzyl, ethynyl, phenylethynyl, phenyl, 4-fluorophenyl, 3-methoxyphenyl, pyridine-2-yl, pyridine-3-yl, pyridine-4-yl, 1-benzyl-1H-[1,2,3]triazol-4-yl, and acetyl.

In certain embodiments, R³ is alkyl, substituted alkyl, cycloalkyl, substituted cycloalkyl, aryl, substituted aryl, heteroaryl, or substituted heteroaryl. In particular embodiments, the R³ is selected from the group consisting of methyl, ethyl, cyclohex-1-enyl, phenyl, 4-t-butylphenyl, 4-trifluoromethylphenyl, 2-trifluoromethoxyphenyl, 3-trifluoromethoxyphenyl, 4-trifluoromethoxyphenyl, 2-chlorophenyl, 3-chlorophenyl, 4-chlorophenyl, 2-chloro-6-fluorophenyl, 4-fluorophenyl, 2,4-dichlorophenyl, 4-methoxyphenyl, 3-cyanophenyl, 4-cyanophenyl, 4-phenoxyphenyl, 4-methanesulfonylphenyl, biphenyl-4-yl, thiophen-2-yl, 5-bromo-furan-2-yl, and pyridine-4-yl.

In certain embodiments, R⁵ is aryl or substituted aryl. In particular embodiments, R⁵ is phenyl or 4-fluorophenyl.

In some embodiments, R⁶ and R⁸ are hydrogen.

In some embodiments, R⁷ is hydroxy. In particular embodiments wherein R⁷ is hydroxy, R¹, R⁶ and R⁸ are all hydrogen. In other embodiments wherein R⁷ is hydroxy, R¹ is methyl and R⁶ and R⁸ are hydrogen.

In another embodiment, the present invention relates to compounds of Formula I(a) or I(a)':

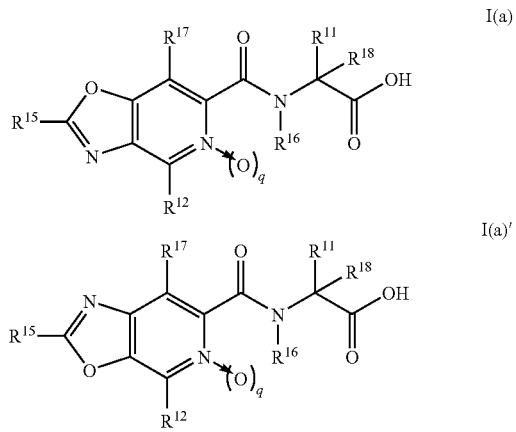

wherein q is 0 or 1;

R¹¹ is selected from the group consisting of hydrogen, deuterium, alkyl, and substituted alkyl;

R¹² is selected from the group consisting of hydrogen, halo, cyano, nitro, alkyl, substituted alkyl, alkenyl, substituted alkenyl, alkynyl, substituted alkynyl, alkoxy, substituted alkoxy, cycloalkyl, substituted cycloalkyl, cycloalkoxy, substituted cycloalkoxy, amino, substituted amino, aminoacyl, acylamino, aryl, substituted aryl, aryloxy, substituted aryloxy, heteroaryl, substituted heteroaryl, heteroaryloxy, substituted heteroaryloxy, heterocyclyl, substituted heterocyclyl, heterocyclyloxy, substituted heterocyclyloxy, alkylthio, substituted alkylthio, cycloalkylthio, substituted cycloalkylthio, arylthio, substituted arylthio, heteroarylthio, substituted heteroarylthio, heterocyclicthio, substituted heterocyclicthio, and acyl;

R¹⁵ is selected from the group consisting of hydrogen, hydroxy, cyano, halo, nitro, acyl, amino, substituted amino, acylamino, sulfonyl, substituted sulfonyl, alkyl, substituted alkyl, alkenyl, substituted alkenyl, alkynyl, substituted alkynyl, cycloalkyl, substituted cycloalkyl, cycloalkoxy, substituted cycloalkoxy, alkoxy, substituted alkoxy, aryl, substituted aryl, aryloxy, substituted aryloxy, alkylthio, substituted alkylthio, cycloalkylthio, substituted cycloalkylthio, arylthio, substituted arylthio, heteroarylthio, substituted heteroarylthio, heterocyclicthio, substituted heterocyclicthio, heterocyclyloxy, substituted heterocyclyloxy, heterocyclic, substituted heterocyclic, heteroaryl, substituted heteroaryl, heteroaryloxy, and substituted heteroaryloxy;

R¹⁶ is selected from the group consisting of hydrogen, alkyl, and substituted alkyl;

R¹⁷ is selected from the group consisting of hydroxy, alkoxy, substituted alkoxy, cycloalkoxy, substituted cycloalkoxy, aryloxy, substituted aryloxy, heteroaryloxy, substituted heteroaryloxy, heterocyclyloxy, substituted heterocyclyloxy, mercapto, alkylthio, substituted alkylthio, cycloalkylthio, substituted cycloalkylthio, arylthio, substituted arylthio, heteroarylthio, substituted heteroarylthio, heterocyclicthio, substituted heterocyclicthio, amino, substituted amino, and acylamino; and R¹⁸ is selected from the group consisting of hydrogen, deuterium, and methyl;

or a pharmaceutically acceptable salt, single stereoisomer, mixture of stereoisomers, ester, or prodrug thereof.

In certain embodiments, $R^{11}$ is hydrogen.

In certain embodiments, $R^{12}$ is selected from the group consisting of hydrogen, alkyl, alkynyl, substituted alkynyl, aryl, and substituted aryl.

In certain embodiments, $R^{15}$ is aryl or substituted aryl.

In certain embodiments, $R^{16}$ and $R^{18}$ are hydrogen.

In certain embodiments, $R^{17}$ is hydroxy.

In certain embodiments, the invention relates to compounds of Formula I(a) or I(a)' wherein $R^{11}$, $R^{16}$, and $R^{18}$ are hydrogen;
  $R^{12}$ is selected from the group consisting of hydrogen, alkyl, alkynyl, substituted alkynyl, aryl, and substituted aryl;
  $R^{15}$ is selected from the group consisting of aryl and substituted aryl; and
  $R^{17}$ is hydroxy.

In certain embodiments, the invention relates to compounds of Formula I(a) or I(a)' wherein
  $R^{11}$, $R^{16}$, and $R^{18}$ are hydrogen;
  $R^{12}$ is selected from the group consisting of hydrogen, methyl, ethyl, butyl, phenylethynyl, phenyl, 4-fluorophenyl, and 3-methoxyphenyl;
  $R^{15}$ is phenyl or 4-fluorophenyl; and
  $R^{17}$ is hydroxy.

In another embodiment, the present invention relates to compounds of Formula I(b) or I(b)':

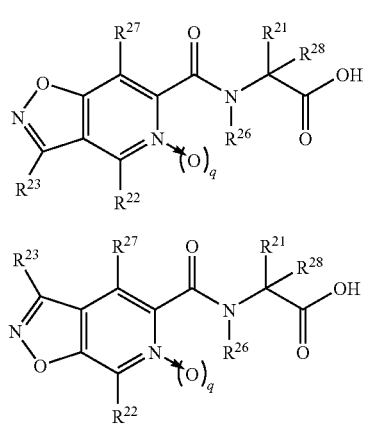

wherein
q is 0 or 1;
$R^{21}$ is selected from the group consisting of hydrogen, deuterium, alkyl, and substituted alkyl;
$R^{22}$ is selected from the group consisting of hydrogen, halo, cyano, nitro, alkyl, substituted alkyl, alkenyl, substituted alkenyl, alkynyl, substituted alkynyl, alkoxy, substituted alkoxy, cycloalkyl, substituted cycloalkyl, cycloalkoxy, substituted cycloalkoxy, amino, substituted amino, aminoacyl, acylamino, aryl, substituted aryl, aryloxy, substituted aryloxy, heteroaryl, substituted heteroaryl, heteroaryloxy, substituted heteroaryloxy, heterocyclyl, substituted heterocyclyl, heterocyclyloxy, substituted heterocyclyloxy, alkylthio, substituted alkylthio, cycloalkylthio, substituted cycloalkylthio, arylthio, substituted arylthio, heteroarylthio, substituted heteroarylthio, heterocyclicthio, substituted heterocyclicthio, and acyl;

$R^{23}$ is selected from the group consisting of hydrogen, hydroxy, cyano, halo, nitro, acyl, amino, substituted amino, acylamino, sulfonyl, substituted sulfonyl, alkyl, substituted alkyl, alkenyl, substituted alkenyl, alkynyl, substituted alkynyl, cycloalkyl, substituted cycloalkyl, cycloalkoxy, substituted cycloalkoxy, alkoxy, substituted alkoxy, cycloalkyl, substituted cycloalkyl, aryl, substituted aryl, aryloxy, substituted aryloxy, alkylthio, substituted alkylthio, cycloalkylthio, substituted cycloalkylthio, arylthio, substituted arylthio, heteroarylthio, substituted heteroarylthio, heterocyclicthio, substituted heterocyclicthio, heterocyclyloxy, substituted heterocyclyloxy, heterocyclic, substituted heterocyclic, heteroaryl, substituted heteroaryl, heteroaryloxy, and substituted heteroaryloxy;
$R^{26}$ is selected from the group consisting of hydrogen, alkyl, and substituted alkyl;
$R^{27}$ is selected from the group consisting of hydroxy, alkoxy, substituted alkoxy, cycloalkoxy, substituted cycloalkoxy, aryloxy, substituted aryloxy, heteroaryloxy, substituted heteroaryloxy, heterocyclyloxy, substituted heterocyclyloxy, mercapto, alkylthio, substituted alkylthio, cycloalkylthio, substituted cycloalkylthio, arylthio, substituted arylthio, heteroarylthio, substituted heteroarylthio, heterocyclicthio, substituted heterocyclicthio, amino, substituted amino, and acylamino; and
$R^{28}$ is selected from the group consisting of hydrogen, deuterium, and methyl;
or a pharmaceutically acceptable salt, single stereoisomer, mixture of stereoisomers, ester, or prodrug thereof.

In certain embodiments, $R^{21}$ is hydrogen or alkyl.

In certain embodiments, $R^{22}$ is selected from the group consisting of hydrogen, cyano, halo, amino, substituted amino, alkyl, substituted alkyl, alkynyl, substituted alkynyl, cycloalkyl, aryl, heteroaryl, substituted heteroaryl, and acyl.

In certain embodiments, $R^{23}$ is alkyl, substituted alkyl, cycloalkyl, substituted cycloalkyl, aryl, substituted aryl, heteroaryl, or substituted heteroaryl.

In certain embodiments, $R^{26}$ and $R^{28}$ are hydrogen.

In certain embodiments, $R^{27}$ is hydroxy.

In certain embodiments, the invention relates to compounds of Formula I(b) or I(b)' wherein
  $R^{21}$ is hydrogen or alkyl;
  $R^{22}$ is selected from the group consisting of hydrogen, cyano, halo, amino, substituted amino, alkyl, substituted alkyl, alkynyl, substituted alkynyl, cycloalkyl, aryl, heteroaryl, substituted heteroaryl, and acyl;
  $R^{23}$ is alkyl, substituted alkyl, cycloalkyl, substituted cycloalkyl, aryl, substituted aryl, heteroaryl, or substituted heteroaryl;
  $R^{26}$ and $R^{28}$ are hydrogen; and
  $R^{27}$ is hydroxy.

In another embodiment, the invention relates to compounds of Formula I(b) or I(b)' wherein
  $R^{21}$ is hydrogen or methyl;
  $R^{22}$ is selected from the group consisting of hydrogen, cyano, bromo, (ethanic acid-2-yl)amino, methyl, trifluoromethyl, pyrazol-1-ylmethyl, cyclopropyl, benzyl, ethynyl, phenylethynyl, phenyl, pyridin-2-yl, pyridin-3-yl. pyridin-4-yl, 1-benzyl-1H-[1,2,3]triazol-4-yl, and acetyl;
  $R^{23}$ is selected from the group consisting of methyl, ethyl, cyclohex-1-enyl, phenyl, 4-t-butylphenyl, 4-trifluoromethylphenyl, 2-trifluoromethoxyphenyl, 4-trifluoromethoxyphenyl, 2-chlorophenyl, 3-chlorophenyl, 4-chlorophenyl, 2-chloro-6-fluorophenyl, 4-fluorophenyl, 2,4-dichlorophenyl, 4-methoxyphenyl, 3-cyanophenyl, 4-cyanophenyl, 4-phenoxyphenyl, 4-methanesulfonylphenyl, biphenyl-4-yl, 3-trifluoromethoxyphenyl, thiophen-2-yl, 5-bromo-furan-2-yl, and pyridine-4-yl.

$R^{26}$ and $R^{28}$ are hydrogen; and
$R^{27}$ is hydroxy.

Compounds of the invention include, but are not limited to, [(7-hydroxy-2-phenyl-oxazolo[4,5-c]pyridine-6-carbonyl)-amino]-acetic acid, {[2-(4-fluoro-phenyl)-7-hydroxy-oxazolo[4,5-c]pyridine-6-carbonyl]-amino}-acetic acid, [(7-hydroxy-4-methyl-2-phenyl-oxazolo[4,5-c]pyridine-6-carbonyl)-amino]-acetic acid, [(4-ethyl-7-hydroxy-2-phenyl-oxazolo[4,5-c]pyridine-6-carbonyl)-amino]-acetic acid, [(7-hydroxy-2,4-diphenyl-oxazolo[4,5-c]pyridine-6-carbonyl)-amino]-acetic acid, [(7-hydroxy-2-phenyl-4-phenylethynyl-oxazolo[4,5-c]pyridine-6-carbonyl)-amino]-acetic acid, [(4-butyl-7-hydroxy-2-phenyl-oxazolo[4,5-c]pyridine-6-carbonyl)-amino]-acetic acid, {[4-(4-fluoro-phenyl)-7-hydroxy-2-phenyl-oxazolo[4,5-c]pyridine-6-carbonyl]-amino}-acetic acid, [(7-hydroxy-2-phenyl-oxazolo[5,4-c]pyridine-6-carbonyl)-amino]-acetic acid, {[7-hydroxy-4-(3-methoxy-phenyl)-2-phenyl-oxazolo[4,5-c]pyridine-6-carbonyl]-amino}-acetic acid, [(4-hydroxy-3-phenyl-isoxazolo[5,4-c]pyridine-5-carbonyl)-amino]-acetic acid, [(4-hydroxy-7-methyl-3-phenyl-isoxazolo[5,4-c]pyridine-5-carbonyl)-amino]-acetic acid, [(4-hydroxy-3,7-diphenyl-isoxazolo[5,4-c]pyridine-5-carbonyl)-amino]-acetic acid, {[3-(4-chloro-phenyl)-4-hydroxy-isoxazolo[5,4-c]pyridine-5-carbonyl]-amino}-acetic acid, {[3-(2-chloro-phenyl)-4-hydroxy-isoxazolo[5,4-c]pyridine-5-carbonyl]-amino}-acetic acid, {[4-hydroxy-3-(4-methoxy-phenyl)-isoxazolo[5,4-c]pyridine-5-carbonyl]-amino}-acetic acid, {[3-(3-chloro-phenyl)-4-hydroxy-isoxazolo[5,4-c]pyridine-5-carbonyl]-amino}-acetic acid, {[3-(2-chloro-6-fluoro-phenyl)-4-hydroxy-isoxazolo[5,4-c]pyridine-5-carbonyl]-amino}-acetic acid, {[3-(4-fluoro-phenyl)-4-hydroxy-isoxazolo[5,4-c]pyridine-5-carbonyl]-amino}-acetic acid, [(7-cyano-4-hydroxy-3-phenyl-isoxazolo[5,4-c]pyridine-5-carbonyl)-amino]-acetic acid, {[3-(4-chloro-phenyl)-4-hydroxy-7-methyl-isoxazolo[5,4-c]pyridine-5-carbonyl]-amino}-acetic acid, {[7-bromo-3-(4-fluoro-phenyl)-4-hydroxy-isoxazolo[5,4-c]pyridine-5-carbonyl]-amino}-acetic acid, {[7-cyano-3-(4-fluoro-phenyl)-4-hydroxy-isoxazolo[5,4-c]pyridine-5-carbonyl]-amino}-acetic acid, {[7-bromo-3-(4-chloro-phenyl)-4-hydroxy-isoxazolo[5,4-c]pyridine-5-carbonyl]-amino}-acetic acid, {[3-(4-chloro-phenyl)-7-cyano-4-hydroxy-isoxazolo[5,4-c]pyridine-5-carbonyl]-amino}-acetic acid, {[3-(4-fluoro-phenyl)-4-hydroxy-7-methyl-isoxazolo[5,4-c]pyridine-5-carbonyl]-amino}-acetic acid, {[3-(3-chloro-phenyl)-7-(ethanic acid-2-yl)amino-4-hydroxy-isoxazolo[5,4-c]pyridine-5-carbonyl]-amino}-acetic acid, {[3-(4-chloro-phenyl)-7-ethynyl-4-hydroxy-isoxazolo[5,4-c]pyridine-5-carbonyl]-amino}-acetic acid, [(3-biphenyl-4-yl-4-hydroxy-isoxazolo[5,4-c]pyridine-5-carbonyl)-amino]-acetic acid, (S)-2-[(4-hydroxy-3-phenyl-isoxazolo[5,4-c]pyridine-5-carbonyl)-amino]-propionic acid, (R)-2-[(4-hydroxy-3-phenyl-isoxazolo[5,4-c]pyridine-5-carbonyl)-amino]-propionic acid, {[4-hydroxy-3-(3-trifluoromethoxy-phenyl)-isoxazolo[5,4-c]pyridine-5-carbonyl]-amino}-acetic acid, [(4-hydroxy-3-phenyl-7-pyridin-3-yl-isoxazolo[5,4-c]pyridine-5-carbonyl)-amino]-acetic acid, {[4-hydroxy-3-(4-trifluoromethyl-phenyl)-isoxazolo[5,4-c]pyridine-5-carbonyl]-amino}-acetic acid, {[4-hydroxy-3-(2-trifluoromethoxy-phenyl)-isoxazolo[5,4-c]pyridine-5-carbonyl]-amino}-acetic acid, [(4-hydroxy-3-phenyl-7-pyridin-4-yl-isoxazolo[5,4-c]pyridine-5-carbonyl)-amino]-acetic acid, [(4-hydroxy-3-phenyl-7-pyridin-2-yl-isoxazolo[5,4-c]pyridine-5-carbonyl)-amino]-acetic acid, [(4-hydroxy-3-phenyl-7-trifluoromethyl-isoxazolo[5,4-c]pyridine-5-carbonyl)-amino]-acetic acid, {[4-hydroxy-3-(4-trifluoromethoxy-phenyl)-isoxazolo[5,4-c]pyridine-5-carbonyl]-amino}-acetic acid, {[3-(4-tert-butyl-phenyl)-4-hydroxy-isoxazolo[5,4-c]pyridine-5-carbonyl]-amino}-acetic acid, [(7-bromo-4-hydroxy-3-phenyl-isoxazolo[5,4-c]pyridine-5-carbonyl)-amino]-acetic acid, [(7-hydroxy-3-phenyl-isoxazolo[4,5-c]pyridine-6-carbonyl)-amino]-acetic acid, (S)-2-[(7-hydroxy-3-phenyl-isoxazolo[4,5-c]pyridine-6-carbonyl)-amino]-propionic acid, (R)-2-[(7-hydroxy-3-phenyl-isoxazolo[4,5-c]pyridine-6-carbonyl)-amino]-propionic acid, {[3-(4-fluoro-phenyl)-7-hydroxy-isoxazolo[4,5-c]pyridine-6-carbonyl]-amino}-acetic acid, {[7-hydroxy-3-(4-methoxy-phenyl)-isoxazolo[4,5-c]pyridine-6-carbonyl]-amino}-acetic acid, [(7-hydroxy-3-thiophen-2-yl-isoxazolo[4,5-c]pyridine-6-carbonyl)-amino]-acetic acid, [(7-hydroxy-3-pyridin-4-yl-isoxazolo[4,5-c]pyridine-6-carbonyl)-amino]-acetic acid, {[3-(5-bromo-furan-2-yl)-7-hydroxy-isoxazolo[4,5-c]pyridine-6-carbonyl]-amino}-acetic acid, [(7-hydroxy-4-methyl-3-phenyl-isoxazolo[4,5-c]pyridine-6-carbonyl)-amino]-acetic acid, [(4-cyano-7-hydroxy-3-thiophen-2-yl-isoxazolo[4,5-c]pyridine-6-carbonyl)-amino]-acetic acid, {[4-cyano-3-(4-fluoro-phenyl)-7-hydroxy-isoxazolo[4,5-c]pyridine-6-carbonyl]-amino}-acetic acid, {[4-cyano-7-hydroxy-3-(4-methoxy-phenyl)-isoxazolo[4,5-c]pyridine-6-carbonyl]-amino}-acetic acid, {[3-(5-bromo-furan-2-yl)-4-cyano-7-hydroxy-isoxazolo[4,5-c]pyridine-6-carbonyl]-amino}-acetic acid, {[7-hydroxy-3-(4-methoxy-phenyl)-4-phenyl-isoxazolo[4,5-c]pyridine-6-carbonyl]-amino}-acetic acid, {[7-hydroxy-3-(4-methoxy-phenyl)-4-methyl-isoxazolo[4,5-c]pyridine-6-carbonyl]amino}-acetic acid, [(7-hydroxy-3-phenyl-4-phenylethynyl-isoxazolo[4,5-c]pyridine-6-carbonyl)-amino]-acetic acid, [(4-ethynyl-7-hydroxy-3-phenyl-isoxazolo[4,5-c]pyridine-6-carbonyl)-amino]-acetic acid, [(4-cyclopropyl-7-hydroxy-3-thiophen-2-yl-isoxazolo[4,5-c]pyridine-6-carbonyl)-amino]-acetic acid, {[7-hydroxy-3-(4-methoxy-phenyl)-4-pyrazol-1-ylmethyl-isoxazolo[4,5-c]pyridine-6-carbonyl]-amino}-acetic acid, [(4-acetyl-7-hydroxy-3-phenyl-isoxazolo[4,5-c]pyridine-6-carbonyl)-amino]-acetic acid, [(4-benzyl-7-hydroxy-3-phenyl-isoxazolo[4,5-c]pyridine-6-carbonyl)-amino]-acetic acid, {[4-(1-benzyl-1H-[1,2,3]triazol-4-yl)-7-hydroxy-3-phenyl-isoxazolo[4,5-c]pyridine-6-carbonyl]-amino}-acetic acid, [(7-hydroxy-3-phenyl-4-trifluoromethyl-isoxazolo[4,5-c]pyridine-6-carbonyl)-amino]-acetic acid, [(3-cyclohex-1-enyl-7-hydroxy-isoxazolo[4,5-c]pyridine-6-carbonyl)-amino]acetic acid, and [(3-ethyl-7-hydroxy-isoxazolo[4,5-c]pyridine-6-carbonyl)-amino]-acetic acid, {[3-(3-Cyano-phenyl)-4-hydroxy-isoxazolo[5,4-c]pyridine-5-carbonyl]-amino}-acetic acid, {[3-(4-Cyano-phenyl)-4-hydroxy-isoxazolo[5,4-c]pyridine-5-carbonyl]-amino}-acetic acid, {[4-Hydroxy-3-(4-phenoxy-phenyl)-isoxazolo[5,4-c]pyridine-5-carbonyl]-amino}-acetic acid, [(4-Hydroxy-3-methyl-isoxazolo[5,4-c]pyridine-5-carbonyl)-amino]-acetic acid, [(4-Hydroxy-3-methyl-7-phenyl-isoxazolo[5,4-c]pyridine-5-carbonyl)-amino]-acetic acid, [(4-Hydroxy-3,7-dimethyl-isoxazolo[5,4-c]pyridine-5-carbonyl)-amino]-acetic acid, {[4-Hydroxy-7-methyl-3-(4-trifluoromethoxy-phenyl)-isoxazolo[5,4-c]pyridine-5-carbonyl]-amino}-acetic acid, {[4-Hydroxy-3-(4-methoxy-phenyl)-7-methyl-isoxazolo[5,4-c]pyridine-5-carbonyl]-amino}-acetic acid, {[3-(2,4-Dichloro-phenyl)-4-hydroxy-isoxazolo[5,4-c]pyridine-5-carbonyl]amino}-acetic acid, and {[4-Hydroxy-3-(4-methanesulfonyl-phenyl)-isoxazolo[5,4-c]pyridine-5-carbonyl]-amino}-acetic acid.

2. Compositions and Methods of the Invention

The invention provides for use of a compound of Formula I, I(a), I(a)', I(b), or I(b)' for the manufacture of a medicament for use in treating various conditions or disorders as described herein. In one embodiment, a pharmaceutical composition is provided comprising at least one compound of Formula I, I(a), I(a)', I(b), or I(b)' and a pharmaceutically acceptable excipient or carrier.

The medicament or composition can further comprise at least one additional therapeutic agent. In one embodiment, the agent is selected from the group consisting of vitamin $B_{12}$, ferrous sulfate, folic acid, and/or recombinant erythropoietin or an erythropoiesis stimulating agent (ESA).

The compounds of the present invention, or medicaments or compositions comprising the compounds, can be used to modulate the stability and/or activity of HIF, and thereby activate HIF-regulated gene expression. The compound, or composition or medicament thereof, can be used in methods to treat, pretreat, or delay progression or onset of conditions mediated at least in part by HIF including, but not limited to, anemia and various aspects of ischemic and hypoxic conditions. In various embodiments, the compound is administered immediately following an acute condition producing ischemia, e.g., myocardial infarction, pulmonary embolism, intestinal infarction, ischemic stroke, acute respiratory failure, renal ischemic-reperfusion injury, etc. In another embodiment, the compound, or composition or medicament thereof, is administered to a patient diagnosed with a chronic condition associated with the development of ischemia, e.g., cardiac cirrhosis, macular degeneration, neonatal respiratory distress syndrome, peripheral artery disease, chronic kidney failure, congestive heart failure, etc. In yet another embodiment, the compound, or composition or medicament thereof, is administered immediately after a trauma or injury. In other embodiments, the compound, or composition or medicament thereof, can be administered to a subject based on predisposing conditions, e.g., hypertension, diabetes, occlusive arterial disease, chronic venous insufficiency, Raynaud's disease, chronic skin ulcers, cirrhosis, congestive heart failure, transient ischemic attack, and systemic sclerosis. In still other embodiments, compounds may be administered to a subject to decrease or prevent the development of tissue damage associated with ischemia or hypoxia.

The compounds of the present invention, or compositions or medicaments thereof, can also be used to increase endogenous erythropoietin (EPO). The compounds, or composition or medicament thereof, can be administered to prevent, pretreat, or treat EPO-associated conditions, including, e.g., conditions associated with anemia and neurological disorders. In one embodiment, the compounds of the present invention, or compositions or medicaments thereof, can be used to treat, pretreat, or delay onset of anemia such as anemia that may develop in association with various conditions or disorders. Conditions associated with anemia include disorders such as acute or chronic kidney disease, diabetes, cancer, ulcers, infection with virus, e.g., HIV, bacteria, or parasites; inflammation, etc. Anemic conditions can further include those associated with procedures or treatments including, e.g., radiation therapy, chemotherapy, dialysis, anesthesia, and surgery. Disorders associated with anemia additionally include abnormal hemoglobin and/or erythrocytes, such as found in disorders such as microcytic anemia, hypochromic anemia, aplastic anemia, etc.

The compounds can be used to increase endogenous EPO in a subject undergoing a specific treatment or procedure, prophylactically or concurrently, for example, an HIV-infected anemic patient being treated with azidothymidine (zidovudine) or other reverse transcriptase inhibitors, an anemic cancer patient receiving cyclic cisplatin- or non-cisplatin-containing chemotherapeutics, or an anemic or non-anemic patient scheduled to undergo surgery. Additionally, the compounds can be used to increase endogenous EPO levels in an anemic or non-anemic patient scheduled to undergo surgery to reduce the need for allogenic blood transfusions or to facilitate banking of blood prior to surgery.

The invention is also directed to a method of inhibiting the activity of at least one hydroxylase enzyme which modifies the alpha subunit of hypoxia inducible factor. The HIF hydroxylase enzyme may be an asparaginyl hydroxylase such as Factor Inhibiting HIF (FIH); and/or a prolyl hydroxylase including, but not limited to, a prolyl hydroxylase selected from the group consisting of EGLN1, EGLN2, and EGLN3. In one embodiment, the method comprises contacting the hydroxylase enzyme with an effective amount of one or more compounds selected from the group comprising compounds of Formula I, I(a), I(a)', I(b), or I(b)'.

3. Definitions

It must be noted that as used herein, and in the appended claims, the singular forms "a," "an," and "the" include plural references unless the context clearly dictates otherwise.

Unless defined otherwise, all technical and scientific terms used herein have the same meanings as commonly understood by one of ordinary skill in the art to which this invention belongs. Although any methods and materials similar or equivalent to those described herein can be used in the practice or testing of the present invention, the preferred methods, devices, and materials are now described. All publications cited herein are incorporated herein by reference in their entirety for the purpose of describing and disclosing the methodologies, reagents, and tools reported in the publications that might be used in connection with the invention. Nothing herein is to be construed as an admission that the invention is not entitled to antedate such disclosure by virtue of prior invention.

The practice of the present invention will employ, unless otherwise indicated, conventional methods of chemistry, biochemistry, molecular biology, cell biology, genetics, immunology, and pharmacology, within the skill of the art. Such techniques are explained fully in the literature. (See, e.g., Gennaro, A. R., ed. (1990) Remington's Pharmaceutical Sciences, 18$^{th}$ ed., Mack Publishing Co.; Colowick, S. et al., eds., Methods In Enzymology, Academic Press, Inc.; D. M. Weir, and C. C. Blackwell, eds. (1986) Handbook of Experimental Immunology, Vols. I-IV, Blackwell Scientific Publications; Maniatis, T. et al., eds. (1989) Molecular Cloning: A Laboratory Manual, 2$^{nd}$ edition, Vols. I-III, Cold Spring Harbor Laboratory Press; Ausubel, F. M. et al., eds. (1999) Short Protocols in Molecular Biology, 4$^{th}$ edition, John Wiley & Sons; Ream et al., eds. (1998) Molecular Biology Techniques: An Intensive Laboratory Course, Academic Press; Newton & Graham eds. (1997) PCR (Introduction to Biotechniques Series), 2nd ed., Springer Verlag).

The term "HIFα" refers to the alpha subunit of hypoxia inducible factor protein. HIFα may be any human or other mammalian protein, or fragment thereof, including, but not limited to, human HIF-1α (Genbank Accession No. Q16665), HIF-2α (Genbank Accession No. AAB41495), and HIF-3α (Genbank Accession No. AAD22668); murine HIF-1α (Genbank Accession No. Q61221), HIF-2α (Genbank Accession No. BAA20130, and AAB41496), and HIF-3α (Genbank Accession No. AAC72734); rat HIF-1α (Genbank Accession No. CAA70701), HIF-2α (Genbank Accession No. CAB96612), and HIF-3α (Genbank Accession No. CAB96611); and bovine HIF-1α (Genbank Accession No. BAA78675), HIF-2α (GenBank Accession No. BAA78676), and HIF-3α (Genbank Accession No. NP_001098812). HIFα may also be any non-mammalian protein or fragment thereof, including *Xenopus laevis* HIF-1α (Genbank Accession No. CAB96628), *Drosophila melanogaster* HIF-1α (Genbank Accession No. JC4851), and chicken HIF-1α (Genbank Accession No. BAA34234).

A fragment of HIFα includes any fragment retaining at least one functional or structural characteristic of HIFα. Fragments of HIFα include, e.g., the regions defined by human HIF-1α from amino acids 401 to 603 (Huang et al., supra), amino acid 531 to 575 (Jiang et al. (1997) *J. Biol. Chem.* 272:19253-19260), amino acid 556 to 575 (Tanimoto et al., supra), amino acid 557 to 571 (Srinivas et al. (1999) *Biochem. Biophys. Res. Commun.* 260:557-561), and amino acid 556 to 575 (Ivan and Kaelin (2001) *Science* 292:464-468). Further, HIFα fragments include any fragment containing at least one occurrence of the motif LXXLAP, e.g., such as occurs in the human HIF-1α native sequence from $L_{397}$ to $P_{402}$, and from $L_{559}$ to $P_{564}$.

The terms "HIF-associated conditions" and "conditions mediated at least in part by HIF" are used inclusively and refer to any condition that can be associated with below normal, abnormal, or inappropriate modulation of HIF. HIF-associated conditions include any condition wherein an increase in HIF level would provide therapeutic benefit. HIF-associated conditions include ishemic, hypoxic, and anemic conditions such as those described below.

The term "HIF hydroxylase" refers to any enzyme that modifies the alpha subunit of HIF by hydroxylation of one or more amino acid residues. HIF hydroxylases include Factor Inhibiting HIF (FIH) (GenBank Accession AAL27308; Mahon et al. (2001) *Genes Dev.* 15:2675-2686; Lando et al. (2002) *Science* 295:858-861; and Lando et al. (2002) *Genes Dev.* 16:1466-1471, which modifies at least one asparagine residue found within HIFα. (Also, see, Elkins et al. (2002) *J. Biol. Chem.* C200644200.) HIF hydroxylases also include HIF prolyl hydroxylases (HIF PHs), each of which modifies at least one proline residue found within HIFα.

The terms "HIF prolyl hydroxylase" and "HIF PH" refer to any enzyme that modifies the alpha subunit of HIF protein by hydroxylation of one or more proline residues. Preferably, the proline residue hydroxylated by HIF PH includes the proline found within the motif LXXLAP. HIF PH includes members of the Egl-Nine (EGLN) gene family described by Taylor (2001, *Gene* 275:125-132), and characterized by Aravind, and Koonin (2001, Genome Biol 2: RESEARCH 0007), Epstein et al. (2001, *Cell* 107:43-54), and Bruick and McKnight (2001, *Science* 294:1337-1340). HIF PH2, as used in exemplary assays described herein (infra), may be any HIF PH2, e.g., human EGLN1 (GenBank Accession No. AAG33965; Dupuy et al. (2000) *Genomics* 69:348-54), mouse EGLN1 (GenBank Accession No. CAC42515), rat EGLN1 (GenBank Accession No. P59722), etc. Alternatively, another HIF PH may be used in the assay. Such HIF PH enzymes include, but are not limited to, human EGLN2 isoform 1 (GenBank Accession No. CAC42510; Taylor, supra), human EGLN2 isoform 3 (GenBank Accession No. NP_542770), mouse EGLN2 (GenBank Accession No. CAC42516), and rat EGLN2 (GenBank Accession No. AA046039); and human EGLN3 (GenBank Accession No. CAC42511; Taylor, supra), mouse EGLN3 (GenBank Accession No. CAC42517), and rat EGLN3 (SM-20) (GenBank Accession No. AAA19321). In other embodiments of the present invention, EGLN may include *Caenorhabditis elegans* EGL-9 (GenBank Accession No. AAD56365) and *Drosophila melanogaster* CG1114 gene product (GenBank Accession No. AAF52050). HIF PH also includes any fragment of the foregoing full-length proteins that retains at least one structural or functional characteristic.

The term "ischemia" refers to a deficient supply of blood to a cell, tissue, organ, etc. Ischemia is associated with a reduction in nutrients, including oxygen, delivered to tissues. Ischemia may arise due to conditions such as atherosclerosis, formation of a thrombus in an artery or vein, blockage of an artery or vein by an embolus, vascular closure due to other causes, e.g., vascular spasm, etc. Such conditions may reduce blood flow, producing a state of hypoperfusion to an organ or tissue, or block blood flow completely. Other conditions that can lead to ischemia include tissue damage due to trauma or injury, such as, e.g., spinal cord injury; viral infection, which can lead to, e.g., congestive heart failure, etc. The term "ischemic condition" refers to conditions or events that are associated with or result in ischemia. Such conditions or events may be acute or chronic. An acute event that is associated with or results in ischemia may include, but is not limited to, an event selected from the group consisting of myocardial infarction, ischemic stroke, pulmonary embolism, perinatal hypoxia, circulatory shock including, e.g., hemorrhagic, septic, cardiogenic, etc.; mountain sickness, acute respiratory failure, etc.; intestinal infarction, acute kidney failure, renal ischemia reperfusion injury, etc. A chronic event that is associated with or results in ischemia may include, but is not limited to, an event selected from the group consisting of atherosclerosis, chronic venous insufficiency, congestive heart failure, cardiac cirrhosis, diabetes, macular degeneration, sleep apnea, Raynaud's disease, systemic sclerosis, nonbacterial thrombotic endocarditis, occlusive artery disease, angina pectoris, transient ischemic attacks (TIAs), chronic alcoholic liver disease, chronic kidney failure, peripheral vascular disorders, ulcers, burns, chronic wounds etc. Ischemia can also result when individuals are placed under general anesthesia, and can cause tissue damage in organs prepared for transplant.

The terms "hypoxia" and "hypoxic" refer to an environment with levels of oxygen below normal. The term "hypoxic condition" includes, but is not limited to, ischemic conditions (ischemic hypoxia) such as those listed above, wherein hypoxia results from reduced circulation; pulmonary disorders (hypoxic hypoxia) such as chronic obstructive pulmonary disease (COPD), severe pneumonia, pulmonary edema, pulmonary hypertension, hyaline membrane disease, and the like, wherein hypoxia results from reduced oxygenation of the blood in the lungs; anemic conditions (anemic hypoxia) such as gastric or duodenal ulcers, liver or renal disease, thrombocytopenia or blood coagulation disorders, cancer or other chronic illness, cancer chemotherapy and other therapeutic interventions that produce anemia, and the like, wherein hypoxia results from a decreased concentration of hemoglobin or red blood cells; and altitude sickness, etc.

The term "anemia" as used herein refers to any abnormality or deficiency in hemoglobin or erythrocytes that leads to reduced oxygen levels in the blood. Anemia can be associated with abnormal production, processing, or performance of erythrocytes and/or hemoglobin. The term anemia refers to any reduction in the number of red blood cells and/or in the level of hemoglobin in blood relative to normal blood levels.

The term "anemic condition" refers to any condition, disease, or disorder associated with anemia. Anemia can arise due to various conditions, for example, acute or chronic kidney disease, infections, inflammation, cancer, irradiation, toxins, diabetes, and surgery. Infections may be due to, e.g., virus, bacteria, and/or parasites, etc. Inflammation may be due to infection or autoimmune disorders, such as rheumatoid arthritis, etc. Anemia can be associated with blood loss due to, e.g., stomach ulcers, duodenal ulcers, hemorrhoids, cancer of the stomach or large intestine, trauma, injury, surgical procedures, etc. Anemia can develop in association with radiation therapy, chemotherapy, and kidney dialysis. Anemia can also develop in HIV-infected patients undergoing treatment with azidothymidine (zidovudine) or other reverse transcriptase inhibitors, and can develop in cancer patients undergoing chemotherapy, e.g., with cyclic cisplatin- or non-cisplatin-containing chemotherapeutics. Aplastic anemia and myelodysplastic syndromes are diseases associated with bone marrow failure which results in decreased production of erythrocytes. Further, anemia can result from defective or abnormal hemoglobin or erythrocytes, such as in disorders including microcytic anemia, hypochromic anemia, etc. Anemia can result from disorders in iron transport, processing, and utilization, see, e.g., sideroblastic anemia, etc.

The terms "disorders," "diseases," and "conditions" are used inclusively herein and refer to any condition deviating from normal.

The terms "erythropoietin" and "EPO" refer to any naturally occurring, recombinant, or synthetic erythropoietin, erythropoiesis stimulating protein (ESP), or erythropoiesis stimulating agent (ESA) including, e.g., human erythropoietin (GenBank Accession No. AAA52400; Lin et al. (1985) Proc. Nat'l. Acad. Sci. USA 82:7580-7584), EPOETIN human recombinant erythropoietin (Amgen, Inc., Thousand Oaks Calif.), ARANESP human recombinant erythropoietin (Amgen), PROCRIT human recombinant erythropoietin (Ortho Biotech Products, L.P., Raritan N.J.), Continuous erythropoiesis receptor activator (CERA; F. Hoffmann-La Roche Ltd., Basel, Switzerland), etc.

The terms "erythropoietin-associated conditions" and "conditions mediated at least in part by erythropoietin" are used inclusively and refer to any condition that can be associated with below normal, abnormal, or inappropriate modulation of erythropoietin. EPO-associated conditions include any condition wherein an increase in EPO level would provide therapeutic benefit. Erythropoietin-associated conditions include anemic conditions such as those described above.

EPO-associated conditions further include neurological disorders and/or injuries, including cases of stroke, trauma, epilepsy, neurodegenerative disease, and the like, wherein erythropoietin may provide a neuroprotective effect. Neurodegenerative diseases contemplated by the invention include Alzheimer's disease, Parkinson's disease, Huntington's disease, and the like.

The terms "treating," "treatment" and the like, are used herein to mean administering a therapy to a patient in need thereof. The therapy may be administered thereby providing a prophylactic effect in terms of completely or partially preventing a disorder or sign or symptom thereof; and/or the therapy may be administered thereby providing a partial or complete cure for a disorder and/or adverse effect attributable to the disorder.

The term "alkyl" refers to saturated monovalent hydrocarbyl groups having from 1 to 10 carbon atoms, more particularly from 1 to 5 carbon atoms, and even more particularly 1 to 3 carbon atoms. This term is exemplified by groups such as methyl, ethyl, n-propyl, iso-propyl, n-butyl, t-butyl, n-pentyl, and the like.

The term "substituted alkyl" refers to an alkyl group of from 1 to 10 carbon atoms, more particularly 1 to 5 carbon atoms, and having from 1 to 5 substituents, preferably 1 to 3 substituents, each of which substituents is independently selected from the group consisting of alkoxy, substituted alkoxy, acyl, acylamino, acyloxy, amino, substituted amino, aminoacyl, aminocarbonylamino, aminothiocarbonylamino, aminocarbonyloxy, aryl, substituted aryl, aryloxy, substituted aryloxy, aryloxyaryl, substituted aryloxyaryl, cyano, halogen, hydroxyl, nitro, oxo, thioxo, carboxyl, carboxyl esters, cycloalkyl, substituted cycloalkyl, thio, alkylthio, substituted alkylthio, arylthio, substituted arylthio, cycloalkylthio, substituted cycloalkylthio, heteroarylthio, substituted heteroarylthio, heterocyclicthio, substituted heterocyclicthio, sulfonyl, substituted sulfonyl, heteroaryl, substituted heteroaryl, heterocyclic, substituted heterocyclic, cycloalkoxy, substituted cycloalkoxy, heteroaryloxy, substituted heteroaryloxy, heterocyclyloxy, substituted heterocyclyloxy, oxycarbonylamino, oxythiocarbonylamino, —OS(O)$_2$-alkyl, —OS(O)$_2$-substituted alkyl, —OS(O)$_2$-aryl, —OS(O)$_2$-substituted aryl, —OS(O)$_2$-heteroaryl, —OS(O)$_2$-substituted heteroaryl, —OS(O)$_2$-heterocyclic, —OS(O)$_2$-substituted heterocyclic, and —OSO$_2$—NR$^{40}$R$^{40}$, —NR$^{40}$S(O)$_2$NR$^{40}$-alkyl, —NR$^{40}$S(O)$_2$—NR$^{40}$-substituted alkyl, —NR$^{40}$S(O)$_2$—NR$^{40}$-aryl, —NR$^{40}$S(O)$_2$—NR$^{40}$-substituted aryl, —NR$^{40}$S(O)$_2$—NR$^{40}$-heteroaryl, —NR$^{40}$S(O)$_2$—NR$^{40}$-substituted heteroaryl, —NR$^{40}$S(O)$_2$—NR$^{40}$-heterocyclic, and —NR$^{40}$S(O)$_2$—NR$^{40}$-substituted heterocyclic, where each R$^{40}$ is independently selected from hydrogen or alkyl. This group is exemplified by groups such as trifluoromethyl, benzyl, pyrazol-1-ylmethyl, etc.

The term "alkoxy" refers to the group "alkyl-O—" which includes, by way of example, methoxy, ethoxy, n-propoxy, iso-propoxy, n-butoxy, t-butoxy, sec-butoxy, n-pentoxy, and the like.

The term "substituted alkoxy" refers to the group "substituted alkyl-O—".

The term "acyl" refers to the groups H—C(O)—, alkyl-C(O)—, substituted alkyl-C(O)—, alkenyl-C(O)—, substituted alkenyl-C(O)—, alkynyl-C(O)—, substituted alkynyl-C(O)—, cycloalkyl-C(O)—, substituted cycloalkyl-C(O)—, aryl-C(O)—, substituted aryl-C(O)—, heteroaryl-C(O)—, substituted heteroaryl-C(O), heterocyclic-C(O)—, and substituted heterocyclic-C(O)—, provided that a nitrogen atom of the heterocyclic or substituted heterocyclic is not bound to the —C(O)— group, wherein alkyl, substituted alkyl, alkenyl, substituted alkenyl, alkynyl, substituted alkynyl, cycloalkyl, substituted cycloalkyl, aryl, substituted aryl, heteroaryl, substituted heteroaryl, heterocyclic, and substituted heterocyclic are as defined herein.

The term "aminoacyl" or "amide", or the prefix "carbamoyl," "carboxamide," "substituted carbamoyl" or "substituted carboxamide" refers to the group —C(O)NR$^{42}$R$^{42}$ where each R$^{42}$ is independently selected from the group consisting of hydrogen, alkyl, substituted alkyl, alkenyl, substituted alkenyl, alkynyl, substituted alkynyl, aryl, substituted aryl, cycloalkyl, substituted cycloalkyl, heteroaryl, substituted heteroaryl, heterocyclic, and substituted heterocyclic; or where each R$^{42}$ is joined to form together with the nitrogen atom a heterocyclic or substituted heterocyclic wherein alkyl, substituted alkyl, alkenyl, substituted alkenyl, alkynyl, substituted alkynyl, cycloalkyl, substituted cycloalkyl, aryl, substituted aryl, heteroaryl, substituted heteroaryl, heterocyclic, and substituted heterocyclic are as defined herein.

The term "acyloxy" refers to the groups alkyl-C(O)O—, substituted alkyl-C(O)O—, alkenyl-C(O)O—, substituted alkenyl-C(O)O—, alkynyl-C(O)O—, substituted alkynyl-C(O)O—, aryl-C(O)O—, substituted aryl-C(O)O—, cycloalkyl-C(O)O—, substituted cycloalkyl-C(O)O—, heteroaryl-C(O)O—, substituted heteroaryl-C(O)O—, heterocyclic-C(O)O—, and substituted heterocyclic-C(O)O—, wherein alkyl, substituted alkyl, alkenyl, substituted alkenyl, alkynyl, substituted alkynyl, cycloalkyl, substituted cycloalkyl, aryl, substituted aryl, heteroaryl, substituted heteroaryl, heterocyclic, and substituted heterocyclic are as defined herein.

The term "alkenyl" refers to a vinyl unsaturated monovalent hydrocarbyl group having from 2 to 6 carbon atoms, and preferably 2 to 4 carbon atoms, and having at least 1, and preferably from 1 to 2 sites of vinyl (>C=C<) unsaturation. Such groups are exemplified by vinyl (ethen-1-yl), allyl, but-3-enyl and the like.

The term "substituted alkenyl" refers to alkenyl groups having from 1 to 3 substituents, and preferably 1 to 2 substituents, selected from the group consisting of alkoxy, substituted alkoxy, acyl, acylamino, acyloxy, amino, substituted amino, aminoacyl, aryl, substituted aryl, aryloxy, substituted aryloxy, cyano, halogen, hydroxyl, nitro, carboxyl, carboxyl esters, cycloalkyl, substituted cycloalkyl, heteroaryl, substituted heteroaryl, heterocyclic, and substituted heterocyclic. This term includes both E (cis) and Z (trans) isomers as appropriate. It also includes mixtures of both E and Z components.

The term "alkynyl" refers to acetylenic unsaturated monovalent hydrocarbyl groups having from 2 to 6 carbon atoms, and preferably 2 to 3 carbon atoms, and having at least 1, and preferably from 1 to 2 sites of acetylenic (—C≡C—) unsaturation. This group is exemplified by ethyn-1-yl, propyn-1-yl, propyn-2-yl, and the like.

The term "substituted alkynyl" refers to alkynyl groups having from 1 to 3 substituents, and preferably 1 to 2 substituents, selected from the group consisting of alkoxy, substituted alkoxy, acyl, acylamino, acyloxy, amino, substituted amino, aminoacyl, aryl, substituted aryl, aryloxy, substituted aryloxy, cyano, halogen, hydroxyl, nitro, carboxyl, carboxyl esters, cycloalkyl, substituted cycloalkyl, heteroaryl, substituted heteroaryl, heterocyclic, and substituted heterocyclic. This group is exemplified by groups such as phenylethynyl, etc.

The term "amino" refers to the group —NH$_2$.

The term "substituted amino" refers to the group —NR$^{41}$R$^{41}$, where each R$^{41}$ is independently selected from the group consisting of hydrogen, alkyl, substituted alkyl, alkenyl, substituted alkenyl, alkynyl, substituted alkynyl, cycloalkyl, substituted cycloalkyl, aryl, substituted aryl, heteroaryl, substituted heteroaryl, heterocyclic, substituted heterocyclic, sulfonyl, and substituted sulfonyl, provided that both R$^{41}$ groups are not hydrogen; or the R$^{41}$ groups can be joined together with the nitrogen atom to form a heterocyclic or substituted heterocyclic ring. This group is exemplified by phenylamino, methylphenylamino, and the like. This group is exemplified by groups such as (ethanic acid-2-yl)amino, etc.

The term "acylamino" refers to the groups —NR$^{45}$C(O)alkyl, —NR$^{45}$C(O)substituted alkyl, —NR$^{45}$C(O)cycloalkyl, —NR$^{45}$C(O)substituted cycloalkyl, —NR$^{45}$C(O)alkenyl, —NR$^{45}$C(O)substituted alkenyl, —NR$^{45}$C(O)alkynyl, —NR$^{45}$C(O)substituted alkynyl, —NR$^{45}$C(O)aryl, —NR$^{45}$C(O)substituted aryl, —NR$^{45}$C(O)heteroaryl, —NR$^{45}$C(O)substituted heteroaryl, —NR$^{45}$C(O)heterocyclic, and —NR$^{45}$C(O)substituted heterocyclic where R$^{45}$ is hydrogen or alkyl, and wherein alkyl, substituted alkyl, alkenyl, substituted alkenyl, alkynyl, substituted alkynyl, cycloalkyl, substituted cycloalkyl, aryl, substituted aryl, heteroaryl, substituted heteroaryl, heterocyclic, and substituted heterocyclic are defined herein.

The term "oxycarbonylamino" refers to the groups —NR$^{46}$C(O)O-alkyl, —NR$^{46}$C(O)O-substituted alkyl, —NR$^{46}$C(O)O-alkenyl, —NR$^{46}$C(O)O-substituted alkenyl, —NR$^{46}$C(O)O-alkynyl, —NR$^{46}$C(O)O-substituted alkynyl, —NR$^{46}$C(O)O-cycloalkyl, —NR$^{46}$C(O)O-substituted cycloalkyl, —NR$^{46}$C(O)O-aryl, —NR$^{46}$C(O)O-substituted aryl, —NR$^{46}$C(O)O -heteroaryl,—NR$^{46}$C(O)O-substituted heteroaryl, —NR$^{46}$C(O)O-heterocyclic, and —NR$^{46}$C(O)O -substitutedheterocyclic where R$^{46}$ is hydrogen or alkyl, and wherein alkyl, substituted alkyl, alkenyl, substituted alkenyl, alkynyl, substituted alkynyl, cycloalkyl, substituted cycloalkyl, aryl, substituted aryl, heteroaryl, substituted heteroaryl, heterocyclic, and substituted heterocyclic are as defined herein.

The term "oxythiocarbonylamino" refers to the groups —NR$^{46}$C(S)O-alkyl, —NR$^{46}$C(S)O -substituted alkyl, —NR$^{46}$C(S)O-alkenyl, —NR$^{46}$C(S)O-substituted alkenyl, —NR$^{46}$C(S)O-alkynyl, —NR$^{46}$C(S)O-substituted alkynyl, —NR$^{46}$C(S)O-cycloalkyl, —NR$^{46}$C(S)O-substituted cycloalkyl, —NR$^{46}$C(S)O-aryl, —NR$^{46}$C(S)O-substituted aryl, —NR$^{46}$C(S)O-heteroaryl, —NR$^{46}$C(S)O-substituted heteroaryl, —NR$^{46}$C(S)O-heterocyclic, and —NR$^{46}$C(S)O-substituted heterocyclic where R$^{46}$ is hydrogen or alkyl, and wherein alkyl, substituted alkyl, alkenyl, substituted alkenyl, alkynyl, substituted alkynyl, cycloalkyl, substituted cycloalkyl, aryl, substituted aryl, heteroaryl, substituted heteroaryl, heterocyclic, and substituted heterocyclic are as defined herein.

The term "aminocarbonyloxy," or the prefix "carbamoyloxy" or "substituted carbamoyloxy," refers to the groups —OC(O)NR$^{47}$R$^{47}$ where each R$^{47}$ is independently selected from the group consisting of hydrogen, alkyl, substituted alkyl, alkenyl, substituted alkenyl, alkynyl, substituted alkynyl, cycloalkyl, substituted cycloalkyl, aryl, substituted aryl, heteroaryl, substituted heteroaryl, heterocyclic, and substituted heterocyclic; or where each R$^{47}$ is joined to form, together with the nitrogen atom, a heterocyclic or substituted heterocyclic, and wherein alkyl, substituted alkyl, alkenyl, substituted alkenyl, alkynyl, substituted alkynyl, cycloalkyl, substituted cycloalkyl, aryl, substituted aryl, heteroaryl, substituted heteroaryl, heterocyclic, and substituted heterocyclic are as defined herein.

The term "aminocarbonylamino" refers to the group —NR$^{49}$C(O)N(R$^{49}$)$_2$ where each R$^{49}$ is independently selected from the group consisting of hydrogen and alkyl.

The term "aminothiocarbonylamino" refers to the group —NR$^{49}$C(S)N(R$^{49}$)$_2$ where each R$^{49}$ is independently selected from the group consisting of hydrogen and alkyl.

The term "aryl" or "Ar" refers to a monovalent aromatic carbocyclic group of from 6 to 14 carbon atoms having a single ring (e.g., phenyl) or multiple condensed rings (e.g., naphthyl or anthryl) which condensed rings may or may not be aromatic (e.g., 2-benzoxazolinone, 2H-1,4-benzoxazin-3 (4H)-one-7-yl, and the like) provided that the point of attachment is the aryl group. Preferred aryls include phenyl and naphthyl.

The term "substituted aryl" refers to aryl groups, as defined herein, which are substituted with from 1 to 4, particularly 1 to 3, substituents selected from the group consisting of hydroxy, acyl, acylamino, acyloxy, alkyl, substituted alkyl, alkoxy, substituted alkoxy, alkenyl, substituted alkenyl, alkynyl, substituted alkynyl, amidino (—C(=NH)-amino or substituted amino), amino, substituted amino, aminoacyl, aminocarbonyloxy, aminocarbonylamino, aminothiocarbonylamino, aryl, substituted aryl, aryloxy, substituted aryloxy, cycloalkoxy, substituted cycloalkoxy, heteroaryloxy, substituted heteroaryloxy, heterocyclyloxy, substituted heterocyclyloxy, carboxyl, carboxyl esters, cyano, thio, alkylthio, substituted alkylthio, arylthio, substituted arylthio, heteroarylthio, substituted heteroarylthio, cycloalkylthio, substituted cycloalkylthio, heterocyclicthio, substituted heterocyclicthio, cycloalkyl, substituted cycloalkyl, guanidino (—NH—C(=NH)-amino or substituted amino), halo, nitro, heteroaryl, substituted heteroaryl, heterocyclic, substituted heterocyclic, oxycarbonylamino, oxythiocarbonylamino, sulfonyl, substituted sulfonyl, —OS(O)$_2$-alkyl, —OS(O)$_2$-substituted alkyl, —OS(O)$_2$-aryl, —OS(O)$_2$-substituted aryl, —OS(O)$_2$-heteroaryl, —OS(O)$_2$-substituted heteroaryl, —OS(O)$_2$-heterocyclic, —OS(O)$_2$-substituted heterocyclic, and —OSO$_2$—NR$^{51}$R$^{51}$, —NR$^{51}$S(O)$_2$—NR$^{51}$-alkyl, —NR$^{51}$S(O)$_2$—NR$^{51}$-substituted alkyl, —NR$^{51}$S(O)$_2$—NR$^{51}$-aryl, —NR$^{51}$S(O)$_2$—NR$^{51}$-substituted aryl, —NR$^{51}$S(O)$_2$—NR$^{51}$-heteroaryl, —NR$^{51}$S(O)$_2$—NR$^{51}$-substituted heteroaryl, —NR$^{51}$S(O)$_2$—NR$^5$-heterocyclic, —NR$^{51}$S(O)$_2$—NR$^{51}$-substituted heterocyclic, where each R$^{51}$ is independently selected from hydrogen or alkyl, wherein each of the terms is as defined herein. This group is exemplified by groups such as 4-fluorophenyl, 3-methoxyphenyl, 4-t-butylphenyl, 4-trifluoromethylphenyl, 2-trifluoromethoxyphenyl, 3-trifluoromethoxyphenyl, 4-trifluoromethoxyphenyl, 2-chlorophenyl, 3-chlorophenyl, 4-chlorophenyl, 2-chloro-6-fluorophenyl, 2,4-dichlorophenyl, 4-methoxyphenyl, 3-cyanophenyl, 4-cyanophenyl, 4-phenoxyphenyl, 4-methanesulfonylphenyl, biphenyl-4-yl, etc.

The term "aryloxy" refers to the group aryl-O— that includes, by way of example, phenoxy, naphthoxy, and the like.

The term "substituted aryloxy" refers to substituted aryl-O— groups.

The term "aryloxyaryl" refers to the group -aryl-O-aryl.

The term "substituted aryloxyaryl" refers to aryloxyaryl groups substituted with from 1 to 3 substituents on either or both aryl rings as defined above for substituted aryl.

The term "carboxyl" refers to —COOH or salts thereof.

The term "carboxyl ester" refers to the groups —C(O)O-alkyl, —C(O)O-substituted alkyl, —C(O)O-alkenyl, —C(O)O-substituted alkenyl, —C(O)O-alkynyl, —C(O)O-substituted alkynyl, —C(O)O-cycloalkyl, —C(O)O-substituted cycloalkyl, —C(O)O-aryl, —C(O)O-substituted aryl, —C(O)O -heteroaryl,—C(O)O-substituted heteroaryl, —C(O)O-heterocyclic, and —C(O)O-substituted heterocyclic.

The term "cyano" refers to the group —CN.

The term "cycloalkyl" refers to a saturated or an unsaturated but nonaromatic cyclic alkyl groups of from 3 to 10, 3 to 8 or 3 to 6 carbon atoms having single or multiple cyclic rings including, by way of example, adamantyl, cyclopropyl, cyclobutyl, cyclopentyl, cyclooctyl, cyclohexenyl, and the like.

The term "substituted cycloalkyl" refers to a cycloalkyl group, having from 1 to 5 substituents selected from the group consisting of oxo (=O), thioxo (=S), alkyl, substituted alkyl, alkoxy, substituted alkoxy, acyl, acylamino, acyloxy, amino, substituted amino, aminoacyl, aryl, substituted aryl, aryloxy, substituted aryloxy, cyano, halogen, hydroxy, nitro, carboxyl, carboxyl esters, cycloalkyl, substituted cycloalkyl, heteroaryl, substituted heteroaryl, heterocyclic, and substituted heterocyclic.

The term "cycloalkoxy" refers to —O-cycloalkyl groups.

The term "substituted cycloalkoxy" refers to —O-substituted cycloalkyl groups.

The term "halo" or "halogen" refers to fluoro, chloro, bromo, and iodo.

The term "hydroxy" or "hydroxyl" refers to the group —OH.

The term "heteroaryl" refers to an aromatic ring of from 1 to 15 carbon atoms, preferably from 1 to 10 carbon atoms, and 1 to 4 heteroatoms within the ring selected from the group consisting of oxygen, nitrogen, and sulfur. Such heteroaryl groups can have a single ring (e.g., pyridinyl, furyl, or thienyl) or multiple condensed rings (e.g., indolizinyl or benzothienyl) provided the point of attachment is through a ring containing the heteroatom and that ring is aromatic. The nitrogen and/or sulfur ring atoms can optionally be oxidized to provide for the N-oxide or the sulfoxide, and sulfone derivatives. Examples of heteroaryls include but are not limited to, pyridinyl, pyrimidinyl, pyrrolyl, indolyl, thiophenyl, thienyl, and furyl.

The term "substituted heteroaryl" refers to heteroaryl groups that are substituted with from 1 to 3 substituents selected from the same group of substituents defined for substituted aryl. This group is exemplified by groups such as 1-benzyl-1H-[1,2,3]triazol-4-yl, 5-bromo-furan-2-yl etc.

The term "heteroaryloxy" refers to the group —O-heteroaryl, and "substituted heteroaryloxy" refers to the group —O-substituted heteroaryl.

The term "heterocyclyl" or "heterocyclic" refers to a saturated or unsaturated (but not aromatic) group having a single ring or multiple condensed rings, from 1 to 10 carbon atoms, and from 1 to 4 hetero atoms selected from the group consisting of nitrogen, sulfur or oxygen within the ring wherein, in fused ring systems, one or more of the rings can be aryl or heteroaryl provided that the point of attachment is at the heterocycle. The nitrogen and/or sulfur ring atoms can optionally be oxidized to provide for the N-oxide or the sulfoxide, and sulfone derivatives.

The term "substituted heterocyclic" refers to heterocycle groups that are substituted with from 1 to 3 of the same substituents as defined for substituted cycloalkyl.

Examples of heterocycles and heteroaryls include, but are not limited to, azetidine, pyrrole, imidazole, pyrazole, pyridine, pyrazine, pyrimidine, pyridazine, indolizine, isoindole, indole, dihydroindole, indazole, purine, quinolizine, isoquinoline, quinoline, phthalazine, naphthylpyridine, quinoxaline, quinazoline, cinnoline, pteridine, carbazole, carboline, phenanthridine, acridine, phenanthroline, isothiazole, phenazine, isoxazole, phenoxazine, phenothiazine, imidazolidine, imidazoline, piperidine, piperazine, indoline, phthalimide, 1,2,3,4-tetrahydroisoquinoline, 4,5,6,7-tetrahydrobenzo[b]thiophene, thiazole, thiazolidine, thiophene, benzo[b]thiophene, morpholinyl, thiomorpholinyl (also referred to as thiamorpholinyl), piperidinyl, pyrrolidine, tetrahydrofuranyl, and the like.

The term "nitro" refers to the group —NO$_2$.

The term "oxo" refers to the atom (=O) or the atom (—O$^-$).

The term "sulfonyl" refers to the group —S(O)$_2$H. The term "substituted sulfonyl" refers to the group —SO$_2$-alkyl, —SO$_2$-substituted alkyl, —SO$_2$-alkenyl, —SO$_2$-substituted alkenyl, —SO$_2$-alkynyl, —SO$_2$-substituted alkynyl, —SO$_2$-cycloalkyl, —SO$_2$-substituted cycloalkyl, —SO$_2$-cycloalkenyl, —SO$_2$-substituted cycloalkenyl, —SO$_2$-aryl, —SO$_2$-substituted aryl, —SO$_2$-heteroaryl, —SO$_2$-substituted heteroaryl, —SO$_2$-heterocyclic, —SO$_2$-substituted heterocyclic, wherein alkyl, substituted alkyl, alkenyl, substituted alkenyl, alkynyl, substituted alkynyl, cycloalkyl, substituted cycloalkyl, cycloalkenyl, substituted cycloalkenyl, aryl, substituted aryl, heteroaryl, substituted heteroaryl, heterocyclic and substituted heterocyclic are as defined herein. Substituted sulfonyl includes groups such as methyl-$SO_2$—, phenyl-$SO_2$—, and 4-methylphenyl-$SO_2$—.

The term "heterocyclyloxy" refers to the group —O-heterocyclic, and "substituted heterocyclyloxy" refers to the group —O-substituted heterocyclic.

The term "thio" or "mercapto" refers to the group —SH.

The term "alkylsulfanyl," "alkylthio," or "thioether" refers to the groups —S-alkyl where alkyl is as defined above.

The term "substituted alkylthio," "substituted alkylsulfanyl," or "substituted alkylthio" refers to the group —S-substituted alkyl where substituted alkyl is as defined above.

The term "cycloalkylthio" or "cycloalkylsulfanyl" refers to the groups —S-cycloalkyl where cycloalkyl is as defined above.

The term "substituted cycloalkylthio" refers to the group —S-substituted cycloalkyl where substituted cycloalkyl is as defined above.

The term "arylthio" or "arylsulfanyl" refers to the group —S-aryl, and "substituted arylthio" refers to the group —S-substituted aryl where aryl and substituted aryl are as defined above.

The term "heteroarylthio" or "heteroarylsulfanyl" refers to the group —S-heteroaryl, and "substituted heteroarylthio" refers to the group —S-substituted heteroaryl where heteroaryl and substituted heteroaryl are as defined above.

The term "heterocyclicthio" or "heterocyclicsulfanyl" refers to the group —S-heterocyclic, and "substituted heterocyclicthio" refers to the group —S-substituted heterocyclic where heterocyclic, and substituted heterocyclic are as defined above.

The term "ester" refers to compounds of Formula I or H that include the group —$COOR^{54}$ where $R^{54}$ is alkyl, substituted alkyl, alkoxy, or substituted alkoxy.

The term "pharmaceutically acceptable salt" refers to pharmaceutically acceptable salts of a compound, which salts are derived from a variety of organic, and inorganic counter ions well known in the art, and include, by way of example only, sodium, potassium, calcium, magnesium, ammonium, tetraalkylammonium, and the like, and when the molecule contains a basic functionality, salts of organic or inorganic acids, such as hydrochloride, hydrobromide, tartrate, mesylate, acetate, maleate, oxalate, and the like.

The terms "stereoisomer" or "stereoisomers" refer to compounds that differ in the chirality of one or more stereocenters. Stereoisomers include enantiomers (compounds are non-superimposable mirror images) and diastereomers (compounds having more than one stereogenic center that are non-mirror images of each other and wherein one or more stereogenic center differs between the two stereoisomers). The compounds of the invention can be present as a mixture of stereoisomers or as a single stereoisomer.

The term "prodrug" as used herein, refers to compounds of Formula I, I(a), I(a)', I(b), or I(b)' that include chemical groups which, in vivo, can be converted into the carboxylate group adjacent to the —$C(R^1)(R^8)$ substituent in compound of Formula I; adjacent to the —$C(R^{11})(R^{18})$ substituent in compound of Formula I(a) or I(a)'; or adjacent to the —$C(R^{21})(R^{28})$ substituent in compound of Formula I(b) or I(b)', and/or can be split off from the amide N-atom and/or can be split off from the oxygen atom beta to the N-atom of the pyridyl ring; and/or can be split off from the N-atom of the pyridyl ring to provide for the active drug, a pharmaceutically acceptable salt thereof, or a biologically active metabolite thereof. Suitable groups are well known in the art and particularly include: for the carboxylic acid moiety, a prodrug selected from, e.g., esters including, but not limited to, those derived from alkyl alcohols, substituted alkyl alcohols, hydroxy substituted aryls and heteroaryls and the like; amides, particularly amides derived from amines of the formula $HNR^{200}R^{210}$ where $R^{200}$ and $R^{210}$ are independently hydrogen, alkyl, substituted alkyl, aryl, substituted aryl, and the like; hydroxymethyl, aldehyde and derivatives thereof; and for the pyridyl N atom, a prodrug selected from, e.g., N-oxides and N-alkyl derivatives.

The term "excipient" as used herein means an inert or inactive substance used in the production of pharmaceutical products or other tablets, including without limitation any substance used as a binder, disintegrant, coating, compression/encapsulation aid, cream or lotion, lubricant, parenteral, sweetener or flavoring, suspending/gelling agent, or wet granulation agent. Binders include, e.g., carbopol, povidone, xanthan gum, etc.; coatings include, e.g., cellulose acetate phthalate, ethylcellulose, gellan gum, maltodextrin, etc.; compression/encapsulation aids include, e.g., calcium carbonate, dextrose, fructose dc, honey dc, lactose (anhydrate or monohydrate; optionally in combination with aspartame, cellulose, or microcrystalline cellulose), starch dc, sucrose, etc.; disintegrants include, e.g., croscarmellose sodium, gellan gum, sodium starch glycolate, etc.; creams and lotions include, e.g., maltodextrin, carrageenans, etc.; lubricants include, e.g., magnesium stearate, stearic acid, sodium stearyl fumarate, etc.; materials for chewable tablets include, e.g., dextrose, fructose dc, lactose (monohydrate, optionally in combination with aspartame or cellulose), etc.; parenterals include, e.g., mannitol, povidone, etc.; plasticizers include, e.g., dibutyl sebacate, polyvinylacetate phthalate, etc.; suspending/gelling agents include, e.g., carrageenan, sodium starch glycolate, xanthan gum, etc.; sweeteners include, e.g., aspartame, dextrose, fructose dc, sorbitol, sucrose dc, etc.; and wet granulation agents include, e.g., calcium carbonate, maltodextrin, microcrystalline cellulose, etc.

It is understood that in all substituted groups defined above, polymers arrived at by defining substituents with further substituents to themselves (e.g., substituted aryl having a substituted aryl group as a substituent which is itself substituted with a substituted aryl group, etc.) are not intended for inclusion herein. Also not included are an infinite numbers of substituents, whether the substituents are the same or different. In such cases, the maximum number of such substituents is three. Each of the above definitions is thus constrained by a limitation that, for example, substituted aryl groups are limited to -substituted aryl-(substituted aryl)-substituted aryl.

Similarly, it is understood that the above definitions are not intended to include impermissible substitution patterns (e.g., methyl substituted with 5 fluoro groups or a hydroxyl group alpha to ethenylic or acetylenic unsaturation). Such impermissible substitution patterns are well known to the skilled artisan.

4. Compound Preparation

The compounds of this invention can be prepared from readily available starting materials using, for example, the following general methods and procedures. It will be appreciated that where typical or preferred process conditions (i.e., reaction temperatures, times, mole ratios of reactants, solvents, pressures, etc.) are given, other process conditions can also be used unless otherwise stated. Optimum reaction conditions may vary with the particular reactants or solvent used, but such conditions can be determined by one skilled in the art by routine optimization procedures.

Additionally, as will be apparent to those skilled in the art, conventional protecting groups may be necessary to prevent certain functional groups from undergoing undesired reactions. Suitable protecting groups for various functional groups as well as suitable conditions for protecting and deprotecting particular functional groups are well known in the art. For example, numerous protecting groups are described in T. W. Greene and G. M. Wuts (1999) *Protecting Groups in Organic Synthesis,* 3rd Edition, Wiley, New York, and references cited therein.

Furthermore, the compounds of this invention may contain one or more chiral centers. Accordingly, if desired, such compounds can be prepared or isolated as pure stereoisomers, i.e., as individual enantiomers or diastereomers, or as stereoisomer-enriched mixtures. All such stereoisomers (and enriched mixtures) are included within the scope of this invention, unless otherwise indicated. Pure stereoisomers (or enriched mixtures) may be prepared using, for example, optically active starting materials or stereoselective reagents well-known in the art. Alternatively, racemic mixtures of such compounds can be separated using, for example, chiral column chromatography, chiral resolving agents, and the like.

The starting materials for the following reactions are generally known compounds or can be prepared by known procedures or obvious modifications thereof. For example, many of the starting materials are available from commercial suppliers such as Aldrich Chemical Co. (Milwaukee, Wis., USA), Bachem (Torrance, Calif., USA), Emka-Chemce or Sigma (St. Louis, Mo., USA). Others may be prepared by procedures, or obvious modifications thereof, described in standard reference texts such as Fieser and Fieser's Reagents for Organic Synthesis, Volumes 1-15 (John Wiley, and Sons, 1991), Rodd's Chemistry of Carbon Compounds, Volumes 1-5, and Supplementals (Elsevier Science Publishers, 1989), Organic Reactions, Volumes 1-40 (John Wiley, and Sons, 1991), March's Advanced Organic Chemistry, (John Wiley, and Sons, 5th Edition, 2001), and Larock's Comprehensive Organic Transformations (VCH Publishers Inc., 1989).

Synthesis of Compounds of the Invention

The oxazolopyridines of this invention are prepared by, for example, the synthetic protocols illustrated in Scheme A.

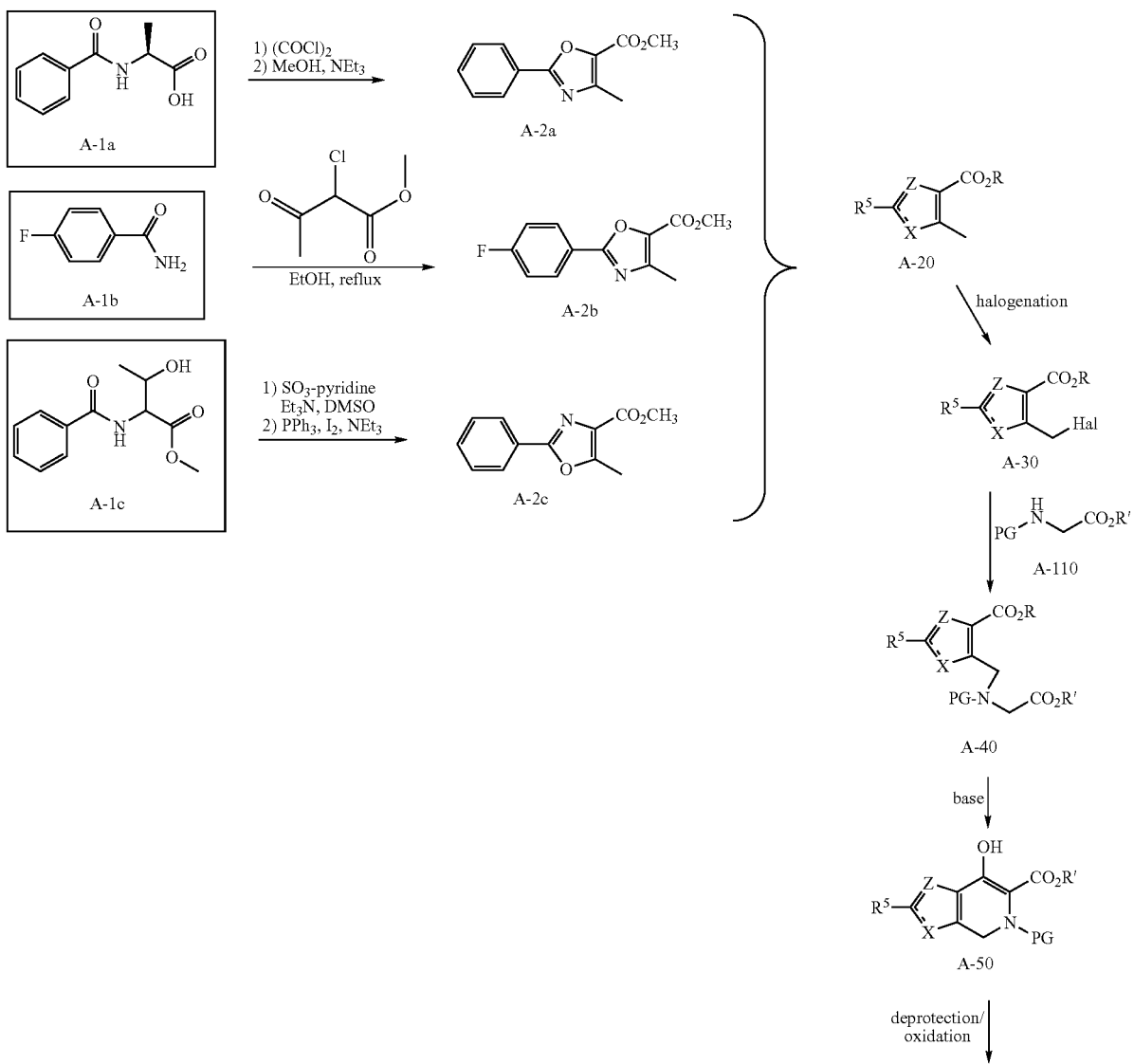

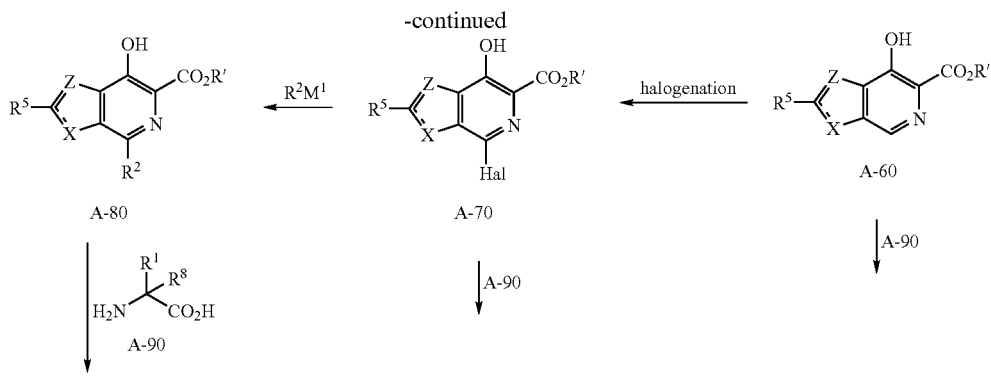

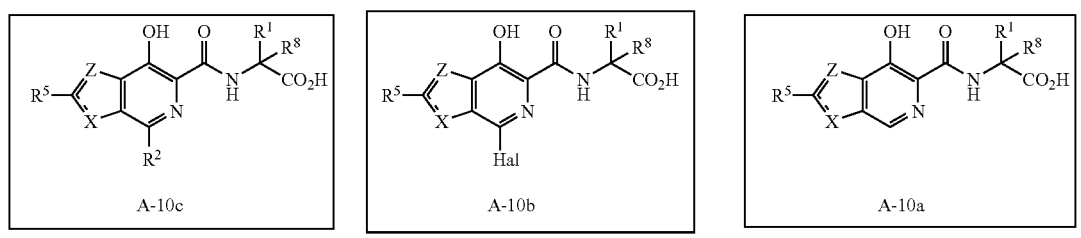

one of Z or X = is —O—, the other is ≡N—

In Scheme A, the substituents R[1], R[2], R[5], and R[8] are as defined herein. Compounds A-20 can be synthesized, for example, from starting materials A-2a, A-2b, and A-2c. These compounds have R[5] as phenyl or substituted phenyl; however, it is contemplated that all variations of R[5] may be employed as starting materials to arrive at the claimed compounds. For example, compound A-2a can be prepared by reacting compound A-1a with oxalylchloride followed by treatment of the resulting 4-methyl-2-phenyl-oxazole-5-carbonyl chloride with methanol and triethylamine according to Cynkowski et al. (J. Chem. Soc., Chem. Commun. (1995) 2335). Compound A-2b can be obtained by reaction of compound A-1b with methyl 2-chloroacetoacetate in ethanol at reflux temperature. Compound A-2c can be obtained by oxidation of compound A-1c with $SO_3$-pyridine, triethylamine in dry DMSO followed by treatment of the resulting 2-benzoylamino-3-oxo-butyric acid methyl ester with triphenylphosphine, iodine, and triethylamine in dichloromethane according to Wipf et al. (Bioorg. Med. Chem., 1997, 5:165).

The aromatic methyl group of compounds A-20 is halogenated using conventional methods to give compounds A-30 (Hal=Cl, Br, I). The halogenation of compounds A-20 is particularly performed with, but not limited to, a stoichiometric amount of NBS in the presence of a catalytic amount of $Bz_2O_2$, azobisisobutyronitrile (AIBN), or another suitable free radical initiator known to one skilled in the art, in $CCl_4$, benzene, or another suitable solvent known to one skilled in the art, typically at, but not limited to, reflux temperature. Upon reaction completion, compounds A-30 can be recovered by conventional techniques such as neutralization, extraction, precipitation, chromatography, filtration and the like; or, alternatively, used in the next step without purification and/or isolation.

Compounds A-30 are used for the N-alkylation of a protected glycine ester A-110 (R'=e.g., alkyl, such as methyl, ethyl, etc.; PG is particularly, but not limited to, Boc or DMB) to give compounds A-40. The N-alkylation step is typically performed in DMF, THF or another suitable solvent known to one skilled in the art, typically at, but not limited to, room temperature or 0° C. in the presence of $K_2CO_3$, NaH, or another suitable base known to one skilled in the art. Upon reaction completion, compounds A-40 can be recovered by conventional techniques such as neutralization, extraction, precipitation, chromatography, filtration and the like; or, alternatively, used in the next step without purification and/or isolation. It is understood that glycine is used for illustrative purposes only.

Compounds A-40 are reacted in THF or another suitable solvent known to one skilled in the art, typically at, but not limited to, −78° C. to room temperature in the presence of KOtBu, or another suitable base known to one skilled in the art to give the compounds A-50. Upon reaction completion, A-50 can be recovered by conventional techniques such as neutralization, extraction, precipitation, chromatography, filtration and the like; or, alternatively, used in the next step without purification and/or isolation.

The compounds A-50 are transformed into compounds A-60 by subsequent deprotection/oxidation. This can be achieved, in addition to other methods known to one skilled in the art, by treatment of A-50 with $SOCl_2$ in a suitable solvent such as $CH_2Cl_2$ (preferred method for PG=DMB); alternatively, A-50 can be deprotected with TFA neat or in a suitable solvent known to one skilled in the art followed by air oxidation in the presence of $NEt_3$ or another suitable base known to one skilled in the art to give the compounds A-60 (preferred method for PG=Boc). Upon reaction completion, A-60 can be recovered by conventional techniques such as neutralization, extraction, precipitation, chromatography, filtration and the like; or, alternatively, used in the next step without purification and/or isolation.

Compounds A-60 are halogenated using conventional methods to give compounds A-70 (Hal=Cl, Br, I). The halogenation of compounds A-60 is particularly performed with, but not limited to, a slight excess of NBS if required in the presence of a catalytic amount of $Bz_2O_2$, in $CCl_4$, benzene, or another suitable solvent known to one skilled in the art, typically at, but not limited to, reflux temperature. Alternatively, the halogenation can be performed with iodine in the presence of a suitable base (particularly, but not limited to, $K_2CO_3$) using a suitable solvent (particularly, but not limited to, $CH_2Cl_2$) at a suitable temperature (particularly, at but not limited to, ambient temperature). Upon reaction completion, compounds A-70 can be recovered by conventional techniques such as neutralization, extraction, precipitation, chromatography, filtration and the like; or, alternatively, used in the next step without purification and/or isolation.

Compounds A-70 are reacted with $R^2M^1$, which includes, but is not limited to, CuCN, suitable boronic acids or their esters such as p-$FC_6H_4B(OH)_2$, or organotin compounds such as n-$Bu_3SnPh$, $Me_4Sn$, etc., or similar reagents known to one skilled in the art in the presence of a suitable catalyst if required (particularly, but not limited to, palladium catalysts known to one skilled in the art such as $Pd(PPh_3)_4$ or $Cl_2Pd(PPh_3)_2$) and if required a suitable base known to one skilled in the art using a suitable solvent known to one skilled in the art to give compounds A-80. Upon reaction completion the compounds A-80 can be recovered by conventional techniques such as neutralization, extraction, precipitation, chromatography, filtration and the like; or, alternatively, used in the next step without purification and/or isolation.

Compounds A-60, A-70, and A-80 are reacted with at least a stoichiometric amount and particularly an excess of an amino acid ($H_2NC(R^1)(R^8)$—$CO_2H$), compound A-90 (e.g., glycine; $R^1=R^8=H$). The reaction is conducted under conventional coupling conditions well known in the art in the presence of particularly sodium methoxide or another suitable base in particularly methanol or another suitable solvent particularly at, but not limited to, reflux temperature. The reaction is continued until it is substantially complete which typically occurs within about 1 to 72 h. Alternatively, the reaction can be performed at elevated temperatures in a microwave oven. Upon reaction completion, the compounds A-10(a-c) can be recovered by conventional techniques such as neutralization, extraction, precipitation, chromatography, filtration and the like.

Alternatively, coupling of compounds A-60, A-70, and A-80 (which are commercially available and are typically in the form of the corresponding free acid) with compound A-90 (typically as an ester derivative) can proceed via conventional peptide coupling procedures, followed by conversion to the corresponding acids using standard methods well known in the art.

Alternatively, compounds A-60, A-70, and A-80 (typically as the corresponding free acid) can be converted into an acid halide and the acid halide coupled with the ester of compound A-90 to provide for the esters of compounds A-10(a-c).

The isoxazolopyridines of this invention, B-300 and B-1100, are preferably prepared by, but are not limited to, the synthetic protocols illustrated in Scheme B-1.

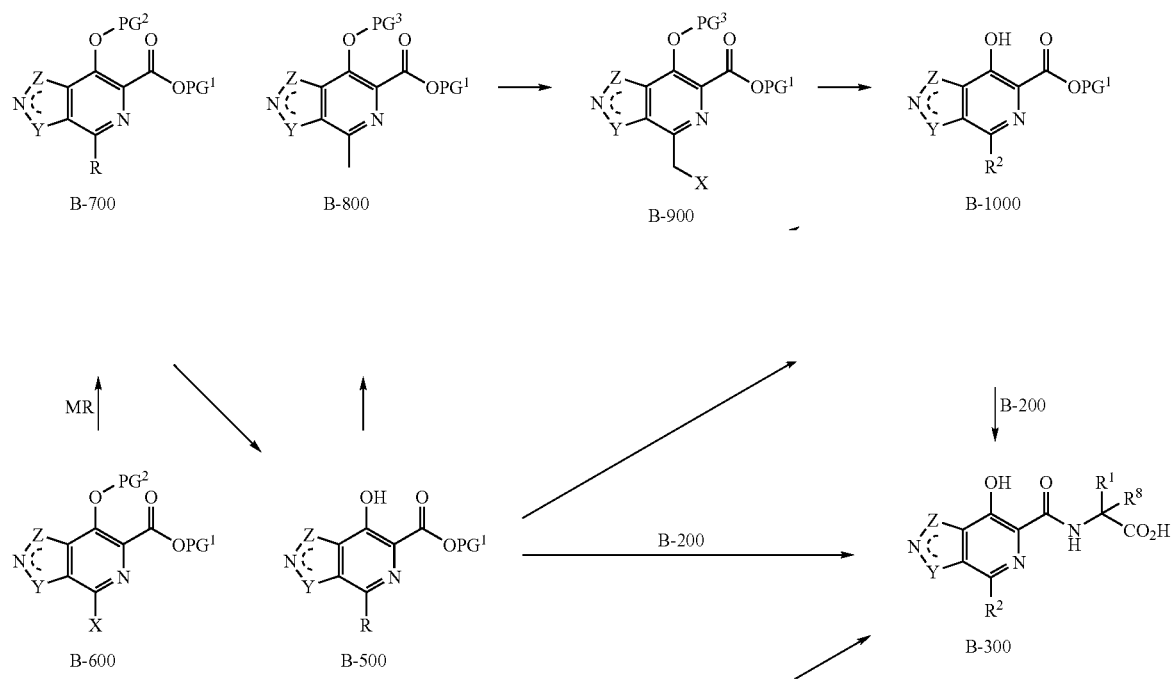

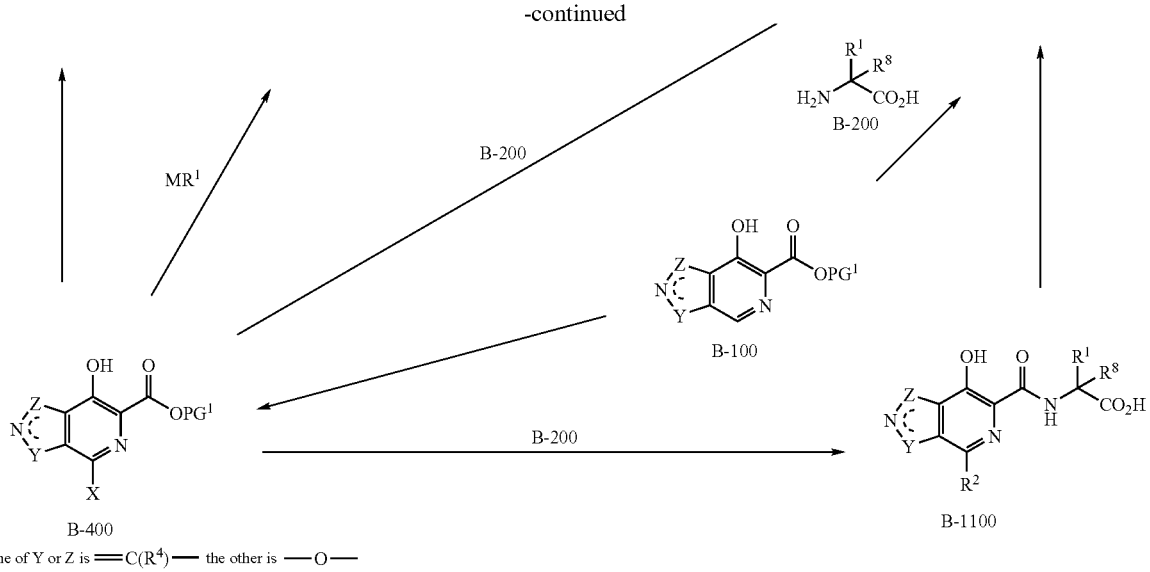

one of Y or Z is =C(R⁴)— the other is —O—

In Scheme B-1, the substituents $R^1$, $R^2$, and $R^8$ are as defined herein, and $R^4$ is either $R^3$ or $R^5$. Compounds B-100, B-400, B-500, and B-1000 (wherein $PG^1$ refers to a suitable protecting group such as methyl, ethyl, butyl, etc.) are reacted with at least a stoichiometric amount and preferably an excess of a suitable alpha-amino acid, compound B-200 (particularly, but not limited to, glycine or alanine). The reaction is conducted under conventional coupling conditions well known in the art. In one embodiment, the reaction is conducted in the presence of sodium methoxide, sodium ethoxide or another suitable base in methanol, DMF or another suitable solvent under elevated reaction temperatures and particularly at reflux. The reaction is continued until it is substantially complete which typically occurs within about 1 to 72 h. Alternatively, the reaction can be performed at elevated temperatures in a microwave oven. Upon reaction completion, the compounds B-300 and B-1100, respectively, can be recovered by conventional techniques such as neutralization, extraction, precipitation, chromatography, filtration and the like.

Alternatively, compounds B-300 ($R^2$=CN) may be obtained by cyanation of compounds B-1100 (wherein X is Cl, Br, or I) with a suitable cyanide source such as, by way of example, CuCN, $Zn(CN)_2$, etc. The cyanation may occur in the presence of a suitable catalyst such as, by way of example, palladium catalyst such as tris(dibenzylideneacetone)dipalladium(0) (see, e.g., Sundermeier et al. (2003) *Eur. J. Inorg. Chem.* 2003(19):3513-3526) and/or additives using a suitable solvent such as, by way of example, DMF, NMP, or N,N-dimethylacetamide. Upon reaction completion, compounds B-300 can be recovered by conventional techniques such as neutralization, extraction, precipitation, chromatography, filtration and the like.

Alternatively, the $R^2$ moiety of compounds B-300 can be modified. For example in one embodiment B-300 (wherein $R^2$ is ethynyl; obtained from the corresponding trimethylsilylethynyl derivative by reaction with $Cs_2CO_3$ in ethanol/dichloromethane) is treated with $HgSO_4/H_2SO_4$ in THF/water using standard reaction conditions well known in the art (not depicted). Upon reaction completion, B-300 (wherein $R^2$ is acetyl) can be recovered by conventional techniques such as neutralization, extraction, precipitation, chromatography, filtration, and the like; or, alternatively, used in the next step without purification and/or isolation.

Compounds B-400 (wherein X is Cl, Br, or I), for use in the reactions depicted in Scheme B-1, can be prepared by halogenation of compounds B-100 using conventional methods. The halogenation of compounds B-100 can for example be performed with a stoichiometric amount or slight excess of, e.g., N-bromosuccinimide in the presence of a catalytic amount of benzoylperoxide, azobisisobutyronitrile, or another suitable free radical initiator, in $CCl_4$, benzene, or another suitable solvent known to one skilled in the art typically at reflux temperature or higher temperatures using a microwave oven. Alternatively, compounds B-100 can be halogenated with a stoichiometric amount or an excess of, e.g., bis(sym-collidine)iodine hexafluorophosphate in $CH_2Cl_2$, or another suitable solvent known to one skilled in the art typically at room temperature. Upon reaction completion, compounds B-400 can be recovered by conventional techniques such as neutralization, extraction, precipitation, chromatography, filtration and the like; or, alternatively, used in the next step without purification and/or isolation.

Compounds B-500 and B-700, for use in the reactions depicted in Scheme B-1 can be prepared by reacting B-400 or B-600 (obtained by protecting the phenolic OH group of B-400 with a suitable protective group, e.g., $PG^2$=anthracen-9-ylmethyl, using standard procedures known to one skilled in the art), respectively, with reagents MR which include, but are not limited to, cyanides such as zinc cyanide, etc.; suitable boronic acids or their derivatives such as $C_6H_4B(OH)_2$, $CH_3B(OH)_2$, trimethylboroxine, potassium benzyltrifluoroborate, etc.; organotin reagents such as n-$Bu_3SnAr$, $Me_4Sn$, etc.; acetylene derivatives such as trimethylsilyl or phenyl acetylene; cadmium/$Br_2CF_2$, copper(I) iodide/methyl fluorosulfonyldifluoroacetate; etc. in the presence of suitable catalyst (such as palladium catalysts including $Pd(PPh_3)_4$, $Cl_2Pd(PPh_3)_2$ or tris(dibenzylideneacetone)dipalladium(0), etc.) and if required suitable mediators, co-catalysts and/or bases known to one skilled in the art using suitable solvents/solvent mixtures. Upon reaction completion, B-500 and B-700 can be recovered by conventional techniques such as neutralization, extraction, precipitation, chromatography, filtration, and the like; or, alternatively, used in the next step without purification and/or isolation.

Alternatively, compounds B-500, for use in the reactions depicted in Scheme B-1, can be prepared by removing $PG^2$ from B-700 using standard deprotection procedures known to one skilled in the art. B-500 can be recovered by conventional techniques such as neutralization, extraction, precipitation, chromatography, filtration, and the like; or, alternatively, used in the next step without purification and/or isolation.

Compounds B-1000, for use in the reactions depicted in Scheme B-1, can be prepared by modification of the R moiety of compounds B-500. In one embodiment B-500 (wherein R is ethynyl; obtained from the corresponding trimethylsilylethynyl derivative by reaction with $Cs_2CO_3$ in ethanol/dichloromethane) is treated with benzylazide using standard reaction conditions well known in the art. Upon reaction completion, B-1000 can be recovered by conventional techniques such as neutralization, extraction, precipitation, chromatography, filtration, and the like; or, alternatively, used in the next step without purification and/or isolation.

In another embodiment the phenolic OH group of B-500 (wherein R is methyl) is protected with a suitable protective group (e.g., $PG^3$=pivaloyl or benzoyl) using standard methods well known to one skilled in the art to give compounds B-800. Subsequently, the compounds B-800 are halogenated to give compounds B-900. The halogenation can for example be performed with a stoichiometric amount or slight excess of, e.g., N-bromosuccinimide in the presence of a catalytic amount of benzoylperoxide, azobisisobutyronitrile, or another suitable free radical initiator, in $CCl_4$, benzene, or another suitable solvent known to one skilled in the art typically at reflux temperature or higher temperatures using a microwave oven. Compounds B-900 are then reacted with suitable nucleophiles such as pyrazole. Upon reaction completion, B-1000 can be recovered by conventional techniques such as neutralization, extraction, precipitation, chromatography, filtration, and the like; or, alternatively, used in the next step without purification and/or isolation.

Compounds B-100 (wherein $PG^1$ refers to a suitable protecting group such as methyl, ethyl, etc.), for use in the reactions depicted in Scheme B-1, are preferably prepared according to, but not limited to, the methods outlined in Scheme B-2. Compounds B-1300 (wherein $PG^4$ refers to a suitable protecting group such as methyl, ethyl, butyl, etc.), for use in the reactions depicted in Scheme B-2, can be obtained by halogenation of compounds B-1200. The halogenation of compounds B-1200 can for example be performed with a stoichiometric amount or excess of, e.g., N-bromosuccinimide in the presence of a catalytic amount of benzoylperoxide, azobisisobutyronitrile, or another suitable free radical initiator, in $CCl_4$, benzene, or another suitable solvent known to one skilled in the art typically at reflux temperature or higher temperatures using a microwave oven. Upon reaction completion, compounds B-1300 can be recovered by conventional techniques such as neutralization, extraction, precipitation, chromatography, filtration and the like; or, alternatively, used in the next step without purification and/or isolation.

Compounds B-1300 are used for the N-alkylation of a protected glycine ester B-1400 ($PG'$=preferably, but not limited to, ethyl; $PG^5$=preferably, but not limited to, DMB) to give compounds B-1500. The N-alkylation step is typically performed in DMF, THF, or another suitable solvent, typically at, but not limited to, room temperature or 0° C. in the presence of $K_2CO_3$, NaH, or another suitable base. Upon reaction completion, the compounds B-1500 can be recovered by conventional techniques such as neutralization, extraction, precipitation, chromatography, filtration, and the like; or, alternatively, used in the next step without purification and/or isolation.

Compounds B-1500 are reacted in THF or another suitable solvent known to one skilled in the art, typically at, but not limited to, 0° C. to room temperature in the presence of KOtBu or another suitable base known to one skilled in the art to give compounds B-1600 (and/or its tautomers; not depicted). Upon reaction completion, B-1600 (and/or its tautomers) can be recovered by conventional techniques such as neutralization, extraction, precipitation, chromatography, fil-

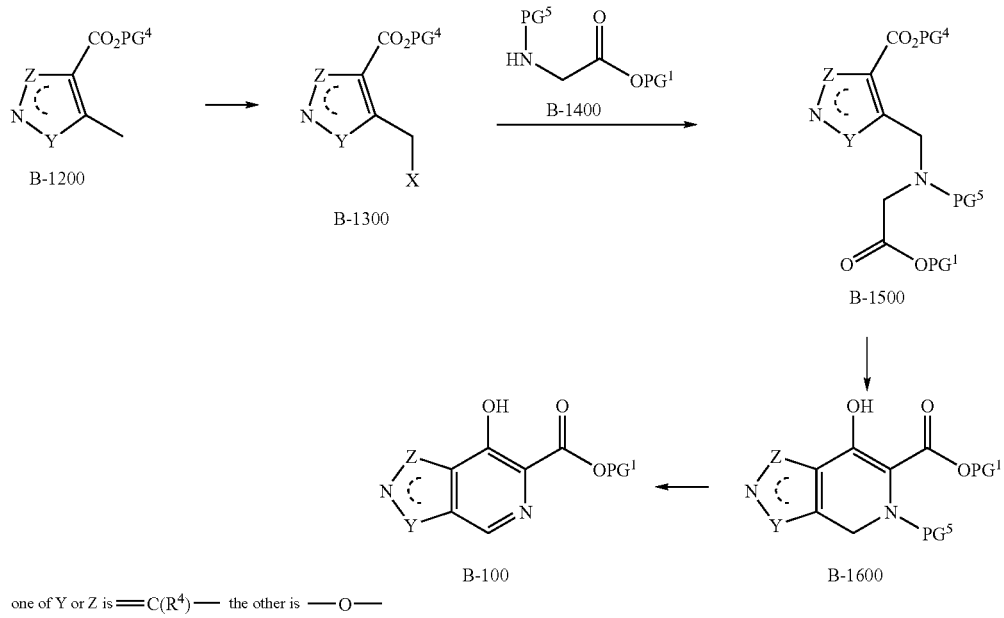

Scheme B-2 one of Y or Z is $=C(R^4)$— the other is —O— tration, and the like; or, alternatively, used in the next step without purification and/or isolation.

Compounds B-1600 (and/or its tautomers) are transformed into compounds B-100 by subsequent deprotection/oxidation. This can be achieved, in addition to other methods known to one skilled in the art, by treatment with $SOCl_2$ in a suitable solvent such as $CH_2Cl_2$. Upon reaction completion, B-100 can be recovered by conventional techniques such as neutralization, extraction, precipitation, chromatography, filtration, and the like; or, alternatively, used in the next step without purification and/or isolation.

Compounds B-1200 (wherein $PG^4$ refers to a suitable protecting group such as methyl, ethyl, etc.), for use in the reactions depicted in Scheme B-2, are preferably prepared according to, but not limited to, the methods outlined in Scheme B-3.

Compounds B-1200 (wherein $PG^4$ refers to a suitable protecting group such as methyl, ethyl, etc.), can be obtained by esterification of compounds B-1700 using standard methods.

Upon reaction completion, the compounds B-1200 can be recovered by conventional techniques such as neutralization, extraction, precipitation, chromatography, filtration, and the like; or, alternatively, used in the next step without purification and/or isolation.

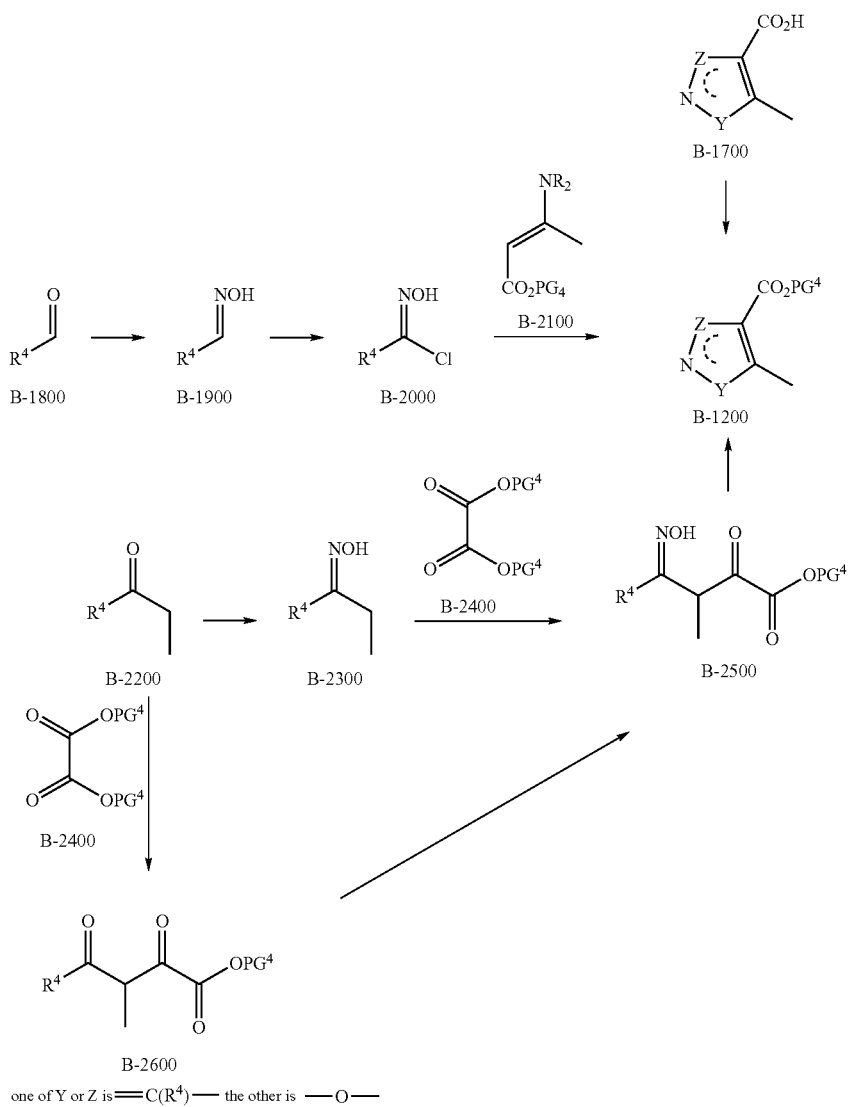

Scheme B-3 one of Y or Z is $=C(R^4)-$ the other is $-O-$

Alternatively, aldehydes B-1800 can be converted by treatment with hydroxylamine (preformed or generated in situ from one of its salts and a suitable base) to the corresponding oximes B-1900 using standard methodologies. Upon reaction completion, the compounds B-1900 can be recovered by conventional techniques such as neutralization, extraction, precipitation, chromatography, filtration, and the like; or, alternatively, used in the next step without purification and/or isolation.

Reaction of the oximes B-1900 with N-chlorosuccinimide provides the corresponding N-hydroxy benzimidoyl chlorides B-2000. Upon reaction completion, the compounds B-2000 can be recovered by conventional techniques such as neutralization, extraction, precipitation, chromatography, filtration, and the like; or, alternatively, used in the next step without purification and/or isolation.

The compounds B-1200 can be obtained by reaction of the N-hydroxy benzimidoyl chlorides B-2000 with enaminoesters B-2100 (wherein $PG^4$=preferably, but not limited to, ethyl; $NR_2$=preferably, but not limited to, pyrrolidino; alternatively, compounds such as alkyl 2-butynoates or suitable salts of alkyl acetoacetates, e.g., the sodium salt of ethyl acetoacetate, can be used instead of enaminoesters B-2100). Upon reaction completion, the compounds B-1200 can be recovered by conventional techniques such as neutralization, extraction, precipitation, chromatography, filtration, and the like; or, alternatively, used in the next step without purification and/or isolation.

Alternatively, ketones B-2200 can be converted by treatment with hydroxylamine (preformed or generated in situ from one of its salts and a suitable base) to the corresponding oximes B-2300 using standard methodologies. Upon reaction completion, the compounds B-2300 can be recovered by conventional techniques such as neutralization, extraction, precipitation, chromatography, filtration, and the like; or, alternatively, used in the next step without purification and/or isolation.

The compounds B-2500 can be obtained by deprotonation of the oximes B-2300 with a suitable base (preferably, but not limited to, LDA) followed by reaction of the resulting dianion with oxalic acid ester B-2400 (wherein $PG^4$=preferably, but not limited to, ethyl). Upon reaction completion, the compounds B-2500 can be recovered by conventional techniques such as neutralization, extraction, precipitation, chromatography, filtration, and the like; or, alternatively, used in the next step without purification and/or isolation. Alternatively, the compounds B-2500 can be obtained by deprotonation of the ketones B-2200 with a suitable base (preferably, but not limited to, LHMDS) followed by reaction of the resulting anion with oxalic acid ester B-2400 (wherein $PG^4$=preferably, but not limited to, ethyl). Upon reaction completion, the resulting compounds B-2600 can be recovered by conventional techniques such as neutralization, extraction, precipitation, chromatography, filtration, and the like; or, alternatively, used in the next step without purification and/or isolation. The conversion to B-2500 can be achieved by the reaction of B-2600 with an equimolar or an excess amount of hydroxylamine (preformed or generated in situ, e.g., from its hydrochloride and suitable base) in aqueous solution. Upon reaction completion, the compounds B-2500 can be recovered by conventional techniques such as neutralization, extraction, precipitation, chromatography, filtration, and the like; or, alternatively, used in the next step without purification and/or isolation.

The compounds B-2500 can be cyclized to the corresponding isoxazoles B-1200 typically by, but not limited to, treatment with sulfuric acid in refluxing ethanol or mesyl chloride/triethyl amine in $CH_2Cl_2$ at room temperature. Upon reaction completion, the compounds B-1200 can be recovered by conventional techniques such as neutralization, extraction, precipitation, chromatography, filtration, and the like; or, alternatively, used in the next step without purification and/or isolation.

Other modifications to arrive at compounds of this invention are well within the skill of the art. For example, modification of the hydroxy group that is beta to the nitrogen of the 5,6-membered bicyclic ring may be done by conventional means to corresponding ethers, etc.

5. Use of Compounds of the Invention

The compounds of the present invention can be used to modulate the stability and/or activity of HIF, and thereby activate HIF-regulated gene expression. The compounds can be used in methods to treat, pretreat, or delay progression or onset of conditions associated with HIF including, but not limited to, anemic, ischemic, and hypoxic conditions. In various embodiments, the compound is administered immediately following an acute condition producing ischemia, e.g., myocardial infarction, pulmonary embolism, intestinal infarction, ischemic stroke, and renal ischemic-reperfusion injury. In another embodiment, the compound is administered to a patient diagnosed with a chronic condition associated with the development of ischemia, e.g., cardiac cirrhosis, macular degeneration, pulmonary embolism, acute respiratory failure, neonatal respiratory distress syndrome, and congestive heart failure. In yet another embodiment, the compound is administered immediately after a trauma or injury. In other embodiments, the compound can be administered to a subject based on predisposing conditions, e.g., hypertension, diabetes, occlusive arterial disease, chronic venous insufficiency, Raynaud's disease, chronic skin ulcers, cirrhosis, congestive heart failure, and systemic sclerosis. In still other embodiments, compounds may be administered to pretreat a subject to decrease or prevent the development of tissue damage associated with ischemia or hypoxia.

In particular embodiments, the compounds of the present invention can be used to increase endogenous erythropoietin (EPO). The compounds can be administered to prevent, pretreat, or treat EPO-associated conditions, including, e.g., conditions associated with anemia and neurological disorders. Conditions associated with anemia include disorders such as acute or chronic kidney disease, diabetes, cancer, ulcers, infection with virus, e.g., HIV, bacteria, or parasites; inflammation, etc. Anemic conditions can further include those associated with procedures or treatments including, e.g., radiation therapy, chemotherapy, dialysis, and surgery. Disorders associated with anemia additionally include abnormal hemoglobin and/or erythrocytes, such as found in disorders such as microcytic anemia, hypochromic anemia, aplastic anemia, etc.

The compounds can be used to increase endogenous EPO in a subject undergoing a specific treatment or procedure, prophylactically or concurrently, for example, an HIV-infected anemic patient being treated with azidothymidine (zidovudine) or other reverse transcriptase inhibitors, an anemic cancer patient receiving cyclic cisplatin- or non-cisplatin-containing chemotherapeutics, or an anemic or non-anemic patient scheduled to undergo surgery. Additionally, the compounds can be used to increase endogenous EPO levels in an anemic or non-anemic patient scheduled to undergo surgery to reduce the need for allogenic blood transfusions or to facilitate banking of blood prior to surgery.

6. Biological Testing

The biological activity of the compounds of the invention may be assessed using any conventionally known methods. Suitable assay methods are well known in the art. The following assays are presented only as examples and are not intended to be limiting. The compounds of the invention are active in at least one of the following assays.

i. Cell-Based HIFα Stabilization Assay

Human cells derived from various tissues are separately seeded into 35 mm culture dishes, and grown at 37° C., 20% $O_2$, 5% $CO_2$ in standard culture medium, e.g., DMEM (Dulbecco's modification of Eagle's medium), 10% FBS (fetal bovine serum). When cell layers reach confluence, the media is replaced with OPTI-MEM media (Invitrogen Life Technologies, Carlsbad Calif.), and cell layers are incubated for approximately 24 hours in 20% $O_2$, 5% $CO_2$ at 37° C. Compound or 0.013% DMSO (dimethyl sulfoxide) is then added to existing medium and incubation is continued overnight.

Following incubation, the media is removed, centrifuged, and stored for analysis (see VEGF and EPO assays below). The cells are washed two times in cold phosphate buffered saline (PBS) and then lysed in 1 mL of 10 mM Tris (pH 7.4), 1 mM EDTA, 150 mM NaCl, 0.5% IGEPAL (Sigma-Aldrich, St. Louis Mo.), and a protease inhibitor mix (Roche Molecular Biochemicals) for 15 minutes on ice. Cell lysates are centrifuged at 3,000×g for 5 minutes at 4° C., and the cytosolic fractions (supernatant) are collected. The nuclei (pellet) are resuspended and lysed in 100 µL of 20 mM HEPES (pH 7.2), 400 mM NaCl, 1 mM EDTA, 1 mM dithiothreitol, and a protease mix (Roche Molecular Biochemicals), centrifuged at 13,000×g for 5 minutes at 4° C., and the nuclear protein fractions (supernatant) are collected.

Nuclear fractions are analyzed for HIF-1α using a QUANTIKINE immunoassay (R&D Systems, Inc., Minneapolis Minn.) according to the manufacturer's instructions.

ii. Cell-Based VEGF and EPO ELISA Assays

Conditioned media collected from cell cultures as described above is analyzed for vascular endothelial growth factor (VEGF) and/or erythropoietin (EPO) expression using an appropriate QUANTIKINE immunoassay (R&D Systems) according to the manufacturer's instructions.

iii. HIF-PH Assay

Ketoglutaric acid α-[1-$^{14}$C]-sodium salt, alpha-ketoglutaric acid sodium salt, and HPLC purified peptide may be obtained from commercial sources, e.g., Perkin-Elmer (Wellesley Mass.), Sigma-Aldrich, and SynPep Corp. (Dublin Calif.), respectively. Peptides for use in the assay may be fragments of HIFα as described above or as disclosed in International Publication WO 2005/118836, incorporated by reference herein. For example, a HLF peptide for use in the HIF-PH assay is [methoxycoumarin]-DLDLEALAPYIPAD-DDFQL-amide. HIF-PH, e.g., HIF-PH2 (EGLN1), can be expressed in, e.g., insect Hi5 cells, and partially purified, e.g., through a SP ion exchange chromatography column. Enzyme activity is determined by capturing $^{14}CO_2$ using an assay described by Kivirikko and Myllyla (1982, *Methods Enzymol.* 82:245-304). Assay reactions contain 50 mM HEPES (pH 7.4), 100 µM α-ketoglutaric acid sodium salt, 0.30 µCi/mL ketoglutaric acid α-[1-$^{14}$C]-sodium salt, 40 µM $FeSO_4$, 1 mM ascorbate, 1541.8 units/mL Catalase, with or without 50 µM peptide substrate and various concentrations of compound of the invention. Reactions are initiated by addition of HIF-PH enzyme.

The peptide-dependent percent turnover is calculated by subtracting percent turnover in the absence of peptide from percent turnover in the presence of substrate peptide. Percent inhibition and $IC_{50}$ are calculated using peptide-dependent percent turnover at given inhibitor concentrations. Calculation of $IC_{50}$ values for each inhibitor is conducted using GraFit software (Erithacus Software Ltd., Surrey UK).

The table below is intended to demonstrate the pharmacological utility of exemplary compounds of the invention. By inhibiting HIF prolyl hydroxylase enzymes, the compounds of the invention stabilize HIFα, which then combines with HIFβ to form an active transcription factor that increases expression of numerous genes involved in response to hypoxic and ischemic conditions.

| Example | Name | Concentration (µM) | % Inhibition (HIF-PH2) |
|---|---|---|---|
| 1 | [(7-Hydroxy-2-phenyl-oxazolo[4,5-c]pyridine-6-carbonyl)-amino]-acetic acid | 200.00 | 99.79 |
| 2 | {[2-(4-Fluoro-phenyl)-7-hydroxy-oxazolo[4,5-c]pyridine-6-carbonyl]-amino}-acetic acid | 200.00 | 100.00 |
| 3 | [(7-Hydroxy-4-methyl-2-phenyl-oxazolo[4,5-c]pyridine-6-carbonyl)-amino]-acetic acid | 200.00 | 48.89 |
| 4 | [(4-Ethyl-7-hydroxy-2-phenyl-oxazolo[4,5-c]pyridine-6-carbonyl)-amino]-acetic acid | 200.00 | 99.17 |
| 5 | [(7-Hydroxy-2,4-diphenyl-oxazolo[4,5-c]pyridine-6-carbonyl)-amino]-acetic acid | 200.00 | 98.70 |
| 6 | [(7-Hydroxy-2-phenyl-4-phenylethynyl-oxazolo[4,5-c]pyridine-6-carbonyl)-amino]-acetic acid | 200.00 | 98.98 |
| 7 | [(4-Butyl-7-hydroxy-2-phenyl-oxazolo[4,5-c]pyridine-6-carbonyl)-amino]-acetic acid | 200.00 | 99.51 |
| 8 | {[4-(4-Fluoro-phenyl)-7-hydroxy-2-phenyl-oxazolo[4,5-c]pyridine-6-carbonyl]-amino}-acetic acid | 200.00 | 97.26 |
| 9 | [(7-Hydroxy-2-phenyl-oxazolo[5,4-c]pyridine-6-carbonyl)-amino]-acetic acid | 200.00 | 98.58 |
| 10 | {[7-Hydroxy-4-(3-methoxy-phenyl)-2-phenyl-oxazolo[4,5-c]pyridine-6-carbonyl]-amino}-acetic acid | 200.00 | 99.04 |
| 11 | [(4-Hydroxy-3-phenyl-isoxazolo[5,4-c]pyridine-5-carbonyl)-amino]-acetic acid | 200.00 | 99.93 |
| 12 | [(4-Hydroxy-7-methyl-3-phenyl-isoxazolo[5,4-c]pyridine-5-carbonyl)-amino]-acetic acid | 200.00 | 98.56 |
| 13 | [(4-Hydroxy-3,7-diphenyl-isoxazolo[5,4-c]pyridine-5-carbonyl)-amino]-acetic acid | 22.22 | 98.43 |
| 14 | {[3-(4-Chloro-phenyl)-4-hydroxy-isoxazolo[5,4-c]pyridine-5-carbonyl]-amino}-acetic acid | 22.22 | 98.80 |
| 15 | {[3-(2-Chloro-phenyl)-4-hydroxy-isoxazolo[5,4-c]pyridine-5-carbonyl]-amino}-acetic acid | 22.22 | 95.68 |

-continued

| Example | Name | Concentration (μM) | % Inhibition (HIF-PH2) |
|---|---|---|---|
| 16 | {[4-Hydroxy-3-(4-methoxy-phenyl)-isoxazolo[5,4-c]pyridine-5-carbonyl]-amino}-acetic acid | 22.22 | 97.89 |
| 17 | {[3-(3-Chloro-phenyl)-4-hydroxy-isoxazolo[5,4-c]pyridine-5-carbonyl]-amino}-acetic acid | 22.22 | 98.58 |
| 18 | {[3-(2-Chloro-6-fluoro-phenyl)-4-hydroxy-isoxazolo[5,4-c]pyridine-5-carbonyl]-amino}-acetic acid | 22.22 | 88.21 |
| 19 | {[3-(4-Fluoro-phenyl)-4-hydroxy-isoxazolo[5,4-c]pyridine-5-carbonyl]-amino}-acetic acid | 22.22 | 97.89 |
| 20 | [(7-Cyano-4-hydroxy-3-phenyl-isoxazolo[5,4-c]pyridine-5-carbonyl)-amino]-acetic acid | 22.22 | 98.52 |
| 21 | {[3-(4-Chloro-phenyl)-4-hydroxy-7-methyl-isoxazolo[5,4-c]pyridine-5-carbonyl]-amino}-acetic acid | 200.00 | 99.42 |
| 22 | {[7-Bromo-3-(4-fluoro-phenyl)-4-hydroxy-isoxazolo[5,4-c]pyridine-5-carbonyl]-amino}-acetic acid | 22.22 | 98.73 |
| 23 | {[7-Cyano-3-(4-fluoro-phenyl)-4-hydroxy-isoxazolo[5,4-c]pyridine-5-carbonyl]-amino}-acetic acid | 22.22 | 98.18 |
| 24 | {[7-Bromo-3-(4-chloro-phenyl)-4-hydroxy-isoxazolo[5,4-c]pyridine-5-carbonyl]-amino}-acetic acid | 22.22 | 100.00 |
| 25 | {[3-(4-Chloro-phenyl)-7-cyano-4-hydroxy-isoxazolo[5,4-c]pyridine-5-carbonyl]-amino}-acetic acid | 22.22 | 98.70 |
| 26 | {[3-(4-Fluoro-phenyl)-4-hydroxy-7-methyl-isoxazolo[5,4-c]pyridine-5-carbonyl]-amino}-acetic acid | 22.22 | 93.85 |
| 27 | {[3-(3-Chloro-phenyl)-7-(ethanic acid-2-yl)amino-4-hydroxy-isoxazolo[5,4-c]pyridine-5-carbonyl]-amino}-acetic acid | 200.00 | 96.45 |
| 28 | {[3-(4-Chloro-phenyl)-7-ethynyl-4-hydroxy-isoxazolo[5,4-c]pyridine-5-carbonyl]-amino}-acetic acid | 22.22 | 96.71 |
| 29 | [(3-Biphenyl-4-yl-4-hydroxy-isoxazolo[5,4-c]pyridine-5-carbonyl)-amino]-acetic acid | 22.22 | 99.39 |
| 30 | 2-[(4-Hydroxy-3-phenyl-isoxazolo[5,4-c]pyridine-5-carbonyl)-amino]-(S)-propionic acid | 200.00 | 100.00 |
| 31 | 2-[(4-Hydroxy-3-phenyl-isoxazolo[5,4-c]pyridine-5-carbonyl)-amino]-(R)-propionic acid | 200.00 | 61.03 |
| 32 | {[4-Hydroxy-3-(3-trifluoromethoxy-phenyl)-isoxazolo[5,4-c]pyridine-5-carbonyl]-amino}-acetic acid | 22.22 | 99.14 |
| 33 | [(4-Hydroxy-3-phenyl-7-pyridin-3-yl-isoxazolo[5,4-c]pyridine-5-carbonyl)-amino]-acetic acid | 22.22 | 99.62 |
| 34 | {[4-Hydroxy-3-(4-trifluoromethyl-phenyl)-isoxazolo[5,4-c]pyridine-5-carbonyl]-amino}-acetic acid | 22.22 | 97.80 |
| 35 | {[4-Hydroxy-3-(2-trifluoromethoxy-phenyl)-isoxazolo[5,4-c]pyridine-5-carbonyl]-amino}-acetic acid | 22.22 | 86.33 |
| 36 | [(4-Hydroxy-3-phenyl-7-pyridin-4-yl-isoxazolo[5,4-c]pyridine-5-carbonyl)-amino]-acetic acid | 22.22 | 98.50 |
| 37 | [(4-Hydroxy-3-phenyl-7-pyridin-2-yl-isoxazolo[5,4-c]pyridine-5-carbonyl)-amino]-acetic acid | 22.22 | 99.58 |
| 38 | [(4-Hydroxy-3-phenyl-7-trifluoromethyl-isoxazolo[5,4-c]pyridine-5-carbonyl)-amino]-acetic acid | 22.22 | 97.85 |
| 39 | {[4-Hydroxy-3-(4-trifluoromethoxy-phenyl)-isoxazolo[5,4-c]pyridine-5-carbonyl]-amino}-acetic acid | 22.22 | 98.69 |
| 40 | {[3-(4-tert-Butyl-phenyl)-4-hydroxy-isoxazolo[5,4-c]pyridine-5-carbonyl]-amino}-acetic acid | 22.22 | 98.76 |
| 41 | [(7-Bromo-4-hydroxy-3-phenyl-isoxazolo[5,4-c]pyridine-5-carbonyl)-amino]-acetic acid | 22.22 | 99.39 |

-continued

| Example | Name | Concentration (μM) | % Inhibition (HIF-PH2) |
|---|---|---|---|
| 42 | [(7-Hydroxy-3-phenyl-isoxazolo[4,5-c]pyridine-6-carbonyl)-amino]-acetic acid | 200.00 | 98.44 |
| 43 | (S)-2-[(7-Hydroxy-3-phenyl-isoxazolo[4,5-c]pyridine-6-carbonyl)-amino]-propionic acid | 200.00 | 98.65 |
| 44 | (R)-2-[(7-Hydroxy-3-phenyl-isoxazolo[4,5-c]pyridine-6-carbonyl)-amino]-propionic acid | 200.00 | 82.20 |
| 45 | {[3-(4-Fluoro-phenyl)-7-hydroxy-isoxazolo[4,5-c]pyridine-6-carbonyl]-amino}-acetic acid | 200.00 | 98.60 |
| 46 | {[7-Hydroxy-3-(4-methoxy-phenyl)-isoxazolo[4,5-c]pyridine-6-carbonyl]-amino}-acetic acid | 200.00 | 99.40 |
| 47 | [(7-Hydroxy-3-thiophen-2-yl-isoxazolo[4,5-c]pyridine-6-carbonyl)-amino]-acetic acid | 200.00 | 98.96 |
| 48 | [(7-Hydroxy-3-pyridin-4-yl-isoxazolo[4,5-c]pyridine-6-carbonyl)-amino]-acetic acid | 200.00 | 100.00 |
| 49 | {[3-(5-Bromo-furan-2-yl)-7-hydroxy-isoxazolo[4,5-c]pyridine-6-carbonyl]-amino}-acetic acid | 200.00 | 96.29 |
| 50 | [(7-Hydroxy-4-methyl-3-phenyl-isoxazolo[4,5-c]pyridine-6-carbonyl)-amino]-acetic acid | 200.00 | 99.52 |
| 51 | [(4-Cyano-7-hydroxy-3-thiophen-2-yl-isoxazolo[4,5-c]pyridine-6-carbonyl)-amino]-acetic acid | 200.00 | 98.79 |
| 52 | {[4-Cyano-3-(4-fluoro-phenyl)-7-hydroxy-isoxazolo[4,5-c]pyridine-6-carbonyl]-amino}-acetic acid | 200.00 | 98.58 |
| 53 | {[4-Cyano-7-hydroxy-3-(4-methoxy-phenyl)-isoxazolo[4,5-c]pyridine-6-carbonyl]-amino}-acetic acid | 200.00 | 99.37 |
| 54 | {[3-(5-Bromo-furan-2-yl)-4-cyano-7-hydroxy-isoxazolo[4,5-c]pyridine-6-carbonyl]-amino}-acetic acid | 200.00 | 99.90 |
| 55 | {[7-Hydroxy-3-(4-methoxy-phenyl)-4-phenyl-isoxazolo[4,5-c]pyridine-6-carbonyl]-amino}-acetic acid | 22.22 | 98.89 |
| 56 | {[7-Hydroxy-3-(4-methoxy-phenyl)-4-methyl-isoxazolo[4,5-c]pyridine-6-carbonyl]-amino}-acetic acid | 200.00 | 98.91 |
| 57 | [(7-Hydroxy-3-phenyl-4-phenylethynyl-isoxazolo[4,5-c]pyridine-6-carbonyl)-amino]-acetic acid | 22.22 | 98.64 |
| 58 | [(4-Ethynyl-7-hydroxy-3-phenyl-isoxazolo[4,5-c]pyridine-6-carbonyl)-amino]-acetic acid | 200.00 | 100.00 |
| 59 | [(4-Cyclopropyl-7-hydroxy-3-thiophen-2-yl-isoxazolo[4,5-c]pyridine-6-carbonyl)-amino]-acetic acid | 200.00 | 99.29 |
| 60 | {[7-Hydroxy-3-(4-methoxy-phenyl)-4-pyrazol-1-ylmethyl-isoxazolo[4,5-c]pyridine-6-carbonyl]-amino}-acetic acid | 200.00 | 100.00 |
| 61 | [(4-Acetyl-7-hydroxy-3-phenyl-isoxazolo[4,5-c]pyridine-6-carbonyl)-amino]-acetic acid | 200.00 | 100.00 |
| 62 | [(4-Benzyl-7-hydroxy-3-phenyl-isoxazolo[4,5-c]pyridine-6-carbonyl)-amino]-acetic acid | 200.00 | 100.00 |
| 63 | {[4-(1-Benzyl-1H-[1,2,3]triazol-4-yl)-7-hydroxy-3-phenyl-isoxazolo[4,5-c]pyridine-6-carbonyl]-amino}-acetic acid | 200.00 | 100.00 |
| 64 | [(7-Hydroxy-3-phenyl-4-trifluoromethyl-isoxazolo[4,5-c]pyridine-6-carbonyl)-amino]-acetic acid | 200.00 | 94.20 |
| 65 | [(3-Cyclohex-1-enyl-7-hydroxy-isoxazolo[4,5-c]pyridine-6-carbonyl)-amino]-acetic acid | 200.00 | 100.00 |
| 66 | [(3-Ethyl-7-hydroxy-isoxazolo[4,5-c]pyridine-6-carbonyl)-amino]-acetic acid | 200.00 | 99.11 |
| 67 | {[3-(3-Cyano-phenyl)-4-hydroxy-isoxazolo[5,4-c]pyridine-5-carbonyl]-amino}-acetic acid | 22.22 | 98.37 |
| 68 | {[3-(4-Cyano-phenyl)-4-hydroxy-isoxazolo[5,4-c]pyridine-5-carbonyl]-amino}-acetic acid | 22.22 | 97.41 |

-continued

| Example | Name | Concentration (μM) | % Inhibition (HIF-PH2) |
|---|---|---|---|
| 69 | {[4-Hydroxy-3-(4-phenoxy-phenyl)-isoxazolo[5,4-c]pyridine-5-carbonyl]-amino}-acetic acid | 22.22 | 99.76 |
| 70 | [(4-Hydroxy-3-methyl-isoxazolo[5,4-c]pyridine-5-carbonyl)-amino]-acetic acid | 22.22 | 99.28 |
| 71 | [(4-Hydroxy-3-methyl-7-phenyl-isoxazolo[5,4-c]pyridine-5-carbonyl)-amino]-acetic acid | 22.22 | 97.46 |
| 72 | [(4-Hydroxy-3,7-dimethyl-isoxazolo[5,4-c]pyridine-5-carbonyl)-amino]-acetic acid | 22.22 | 94.61 |
| 73 | {[4-Hydroxy-7-methyl-3-(4-trifluoromethoxy-phenyl)-isoxazolo[5,4-c]pyridine-5-carbonyl]-amino}-acetic acid | 22.22 | 97.38 |
| 74 | {[4-Hydroxy-3-(4-methoxy-phenyl)-7-methyl-isoxazolo[5,4-c]pyridine-5-carbonyl]-amino}-acetic acid | 22.22 | 94.42 |
| 75 | {[3-(2,4-Dichloro-phenyl)-4-hydroxy-isoxazolo[5,4-c]pyridine-5-carbonyl]-amino}-acetic acid | 22.22 | 98.01 |
| 76 | {[4-Hydroxy-3-(4-methanesulfonyl-phenyl)-isoxazolo[5,4-c]pyridine-5-carbonyl]amino}-acetic acid | 22.22 | 99.43 |

7. Pharmaceutical Formulations and Routes of Administration

The compositions of the present invention can be delivered directly or in pharmaceutical compositions along with suitable carriers or excipients, as is well known in the art. Present methods of treatment can comprise administration of an effective amount of a compound of the invention to a subject in need; e.g., a subject having or at risk for anemia due to, e.g., chronic renal failure, diabetes, cancer, AIDS, radiation therapy, chemotherapy, kidney dialysis, or surgery; or, e.g., a subject having or at risk for ischemia due to, e.g., myocardial infarction, congestive heart failure, cardiac cirrhosis, pulmonary insufficiency, atherosclerosis, peripheral vascular disease, or the like. In a preferred embodiment, the subject is a mammalian subject, and in a most preferred embodiment, the subject is a human subject.

An effective amount of such agents can readily be determined by routine experimentation, as can the most effective and convenient route of administration, and the most appropriate formulation. Various formulations and drug delivery systems are available in the art. See, e.g., Gennaro, A. R., ed. (1995) Remington's Pharmaceutical Sciences, supra.

Suitable routes of administration may, for example, include oral, rectal, topical, nasal, pulmonary, ocular, intestinal, and parenteral administration. Primary routes for parenteral administration include intravenous, intramuscular, and subcutaneous administration. Secondary routes of administration include intraperitoneal, intra-arterial, intra-articular, intracardiac, intracisternal, intradermal, intralesional, intraocular, intrapleural, intrathecal, intrauterine, and intraventricular administration. The indication to be treated, along with the physical, chemical, and biological properties of the drug, dictate the type of formulation and the route of administration to be used, as well as whether local or systemic delivery would be preferred.

Pharmaceutical dosage forms of a compound of the invention may be provided in an instant release, controlled release, sustained release, or target drug-delivery system. Commonly used dosage forms include, for example, solutions and suspensions, (micro-) emulsions, ointments, gels and patches, liposomes, tablets, dragees, soft or hard shell capsules, suppositories, ovules, implants, amorphous or crystalline powders, aerosols, and lyophilized formulations. Depending on route of administration used, special devices may be required for application or administration of the drug, such as, for example, syringes and needles, inhalers, pumps, injection pens, applicators, or special flasks. Pharmaceutical dosage forms are often composed of the drug, an excipient(s), and a container/closure system. One or multiple excipients, also referred to as inactive ingredients, can be added to a compound of the invention to improve or facilitate manufacturing, stability, administration, and safety of the drug, and can provide a means to achieve a desired drug release profile. Therefore, the type of excipient(s) to be added to the drug can depend on various factors, such as, for example, the physical and chemical properties of the drug, the route of administration, and the manufacturing procedure. Pharmaceutically acceptable excipients are available in the art and include those listed in various pharmacopoeias. (See, e.g., the U.S. Pharmacopeia (USP), Japanese Pharmacopoeia (JP), European Pharmacopoeia (EP), and British pharmacopeia (BP); the U.S. Food and Drug Administration (www.fda.gov) Center for Drug Evaluation and Research (CEDR) publications, e.g., Inactive Ingredient Guide (1996); Ash and Ash, Eds. (2002) Handbook of Pharmaceutical Additives, Synapse Information Resources, Inc., Endicott N.Y.; etc.)

Pharmaceutical dosage forms of a compound of the present invention may be manufactured by any of the methods well-known in the art, such as, for example, by conventional mixing, sieving, dissolving, melting, granulating, dragee-making, tabletting, suspending, extruding, spray-drying, levigating, emulsifying, (nano/micro-) encapsulating, entrapping, or lyophilization processes. As noted above, the compositions of the present invention can include one or more physiologically acceptable inactive ingredients that facilitate processing of active molecules into preparations for pharmaceutical use.

Proper formulation is dependent upon the desired route of administration. For intravenous injection, for example, the composition may be formulated in aqueous solution, if necessary using physiologically compatible buffers, including, for example, phosphate, histidine, or citrate for adjustment of the formulation pH, and a tonicity agent, such as, for example, sodium chloride or dextrose. For transmucosal or nasal administration, semisolid, liquid formulations, or patches may be preferred, possibly containing penetration enhancers. Such penetrants are generally known in the art. For oral administration, the compounds can be formulated in liquid or solid dosage forms, and as instant or controlled/sustained release formulations. Suitable dosage forms for oral ingestion by a subject include tablets, pills, dragees, hard and soft shell capsules, liquids, gels, syrups, slurries, suspensions, and emulsions. The compounds may also be formulated in rectal compositions, such as suppositories or retention enemas, e.g., containing conventional suppository bases such as cocoa butter or other glycerides.

Solid oral dosage forms can be obtained using excipients, which may include fillers, disintegrants, binders (dry and wet), dissolution retardants, lubricants, glidants, antiadherants, cationic exchange resins, wetting agents, antioxidants, preservatives, coloring, and flavoring agents. These excipients can be of synthetic or natural source. Examples of such excipients include cellulose derivatives, citric acid, dicalcium phosphate, gelatine, magnesium carbonate, magnesium/sodium lauryl sulfate, mannitol, polyethylene glycol, polyvinyl pyrrolidone, silicates, silicium dioxide, sodium benzoate, sorbitol, starches, stearic acid or a salt thereof, sugars (i.e. dextrose, sucrose, lactose, etc.), talc, tragacanth mucilage, vegetable oils (hydrogenated), and waxes. Ethanol and water may serve as granulation aides. In certain instances, coating of tablets with, for example, a taste-masking film, a stomach acid resistant film, or a release-retarding film is desirable. Natural and synthetic polymers, in combination with colorants, sugars, and organic solvents or water, are often used to coat tablets, resulting in dragees. When a capsule is preferred over a tablet, the drug powder, suspension, or solution thereof can be delivered in a compatible hard or soft shell capsule.

In one embodiment, the compounds of the present invention can be administered topically, such as through a skin patch, a semi-solid, or a liquid formulation, for example a gel, a (micro-) emulsion, an ointment, a solution, a (nano/micro)-suspension, or a foam. The penetration of the drug into the skin and underlying tissues can be regulated, for example, using penetration enhancers; the appropriate choice and combination of lipophilic, hydrophilic, and amphiphilic excipients, including water, organic solvents, waxes, oils, synthetic and natural polymers, surfactants, emulsifiers; by pH adjustment; and use of complexing agents. Other techniques, such as iontophoresis, may be used to regulate skin penetration of a compound of the invention. Transdermal or topical administration would be preferred, for example, in situations in which local delivery with minimal systemic exposure is desired.

For administration by inhalation, or administration to the nose, the compounds for use according to the present invention are conveniently delivered in the form of a solution, suspension, emulsion, or semisolid aerosol from pressurized packs, or a nebuliser, usually with the use of a propellant, e.g., halogenated carbons derived from methane and ethane, carbon dioxide, or any other suitable gas. For topical aerosols, hydrocarbons like butane, isobutene, and pentane are useful. In the case of a pressurized aerosol, the appropriate dosage unit may be determined by providing a valve to deliver a metered amount. Capsules and cartridges of, for example, gelatin, for use in an inhaler or insufflator, may be formulated. These typically contain a powder mix of the compound and a suitable powder base such as lactose or starch.

Compositions formulated for parenteral administration by injection are usually sterile and can be presented in unit dosage forms, e.g., in ampoules, syringes, injection pens, or in multi-dose containers, the latter usually containing a preservative. The compositions may take such forms as suspensions, solutions, or emulsions in oily or aqueous vehicles, and may contain formulatory agents, such as buffers, tonicity agents, viscosity enhancing agents, surfactants, suspending and dispersing agents, antioxidants, biocompatible polymers, chelating agents, and preservatives. Depending on the injection site, the vehicle may contain water, a synthetic or vegetable oil, and/or organic co-solvents. In certain instances, such as with a lyophilized product or a concentrate, the parenteral formulation would be reconstituted or diluted prior to administration. Depot formulations, providing controlled or sustained release of a compound of the invention, may include injectable suspensions of nano/micro particles or nano/micro or non-micronized crystals. Polymers such as poly(lactic acid), poly(glycolic acid), or copolymers thereof, can serve as controlled/sustained release matrices, in addition to others well known in the art. Other depot delivery systems may be presented in form of implants and pumps requiring incision.

Suitable carriers for intravenous injection for the molecules of the invention are well-known in the art and include water-based solutions containing a base, such as, for example, sodium hydroxide, to form an ionized compound, sucrose or sodium chloride as a tonicity agent; and a buffer, for example, a buffer that contains phosphate or histidine. Co-solvents, such as, for example, polyethylene glycols, may be added. These water-based systems are effective at dissolving compounds of the invention and produce low toxicity upon systemic administration. The proportions of the components of a solution system may be varied considerably, without destroying solubility and toxicity characteristics. Furthermore, the identity of the components may be varied. For example, low-toxicity surfactants, such as polysorbates or poloxamers, may be used, as can polyethylene glycol or other co-solvents, biocompatible polymers such as polyvinyl pyrrolidone may be added, and other sugars and polyols may substitute for dextrose.

A therapeutically effective dose can be estimated initially using a variety of techniques well-known in the art. Initial doses used in animal studies may be based on effective concentrations established in cell culture assays. Dosage ranges appropriate for human subjects can be determined, for example, using data obtained from animal studies and cell culture assays.

An effective amount or a therapeutically effective amount or dose of an agent, e.g., a compound of the invention, refers to that amount of the agent or compound that results in amelioration of symptoms or a prolongation of survival in a subject. Toxicity and therapeutic efficacy of such molecules can be determined by standard pharmaceutical procedures in cell cultures or experimental animals, e.g., by determining the LD50 (the dose lethal to 50% of the population) and the ED50 (the dose therapeutically effective in 50% of the population). The dose ratio of toxic to therapeutic effects is the therapeutic index, which can be expressed as the ratio LD50/ED50. Agents that exhibit high therapeutic indices are preferred.

The effective amount or therapeutically effective amount is the amount of the compound or pharmaceutical composition that will elicit the biological or medical response of a tissue, system, animal or human that is being sought by the researcher, veterinarian, medical doctor or other clinician. Dosages particularly fall within a range of circulating concentrations that includes the ED50 with little or no toxicity. Dosages may vary within this range depending upon the dosage form employed and/or the route of administration utilized. The exact formulation, route of administration, dosage, and dosage interval should be chosen according to methods known in the art, in view of the specifics of a subject's condition.

Dosage amount and interval may be adjusted individually to provide plasma levels of the active moiety that are sufficient to achieve the desired effects; i.e., the minimal effective concentration (MEC). The MEC will vary for each compound but can be estimated from, for example, in vitro data and animal experiments. Dosages necessary to achieve the MEC will depend on individual characteristics and route of administration. In cases of local administration or selective uptake, the effective local concentration of the drug may not be related to plasma concentration.

The amount of agent or composition administered may be dependent on a variety of factors, including the sex, age, and weight of the subject being treated, the severity of the affliction, the manner of administration, and the judgment of the prescribing physician.

The present compositions may, if desired, be presented in a pack or dispenser device containing one or more unit dosage forms containing the active ingredient. Such a pack or device may, for example, comprise metal or plastic foil, such as a blister pack; or glass and rubber stoppers such as in vials. The pack or dispenser device may be accompanied by instructions for administration. Compositions comprising a compound of the invention formulated in a compatible pharmaceutical carrier may also be prepared, placed in an appropriate container, and labeled for treatment of an indicated condition.

These and other embodiments of the present invention will readily occur to those of ordinary skill in the art in view of the disclosure herein and are specifically contemplated.

EXAMPLES

The invention is further understood by reference to the following examples, which are intended to be purely exemplary of the invention. The present invention is not limited in scope by the exemplified embodiments, which are intended as illustrations of single aspects of the invention only. Any methods that are functionally equivalent are within the scope of the invention. Various modifications of the invention in addition to those described herein will become apparent to those skilled in the art from the foregoing description and accompanying figures. Such modifications fall within the scope of the appended claims.

Unless otherwise stated all temperatures are in degrees Celsius (° C.). Also, in these examples and elsewhere, abbreviations have the following meanings:

| | |
|---|---|
| μCi = | Microcuries |
| μL = | Microliter |
| μM = | Micromolar |
| Boc = | tert-Butoxycarbonyl |
| br = | Broad |
| br s = | Broad singlet |
| BzOOBz or $Bz_2O_2$ = | Benzoyl peroxide |
| Cd powder = | Cadmium powder |
| $CCl_4$ = | Carbon tetrachloride |
| $CH_2Cl_2$ = | Methylene dichloride |
| $CHCl_3$ = | Chloroform |
| $(COCl_2)$ = | Oxalyl chloride |
| $Cs_2CO_3$ = | Cesium carbonate |
| CuCN = | Copper cyanide |
| $CuSO_4$ = | Copper sulfate |
| d = | Doublet |
| DMAP = | Dimethylaminopropylamine |
| DMB = | 2,4-Dimethoxy-benzyl |
| DMF = | Dimethyl formamide |

-continued

| | |
|---|---|
| DMSO = | Dimethyl sulfoxide |
| EDTA = | Ethylenediamine tetraacetic acid |
| ESI MS = | Electrospray Ionization Mass Spectrometry |
| EtOH = | Ethanol |
| EtOAc = | Ethyl acetate |
| $FeSO_4$ = | Ferrous sulfate |
| g = | Gram |
| h = | Hour |
| HCl = | Hydrochloric acid |
| $HgSO_4$ = | Mercuric sulfate |
| $H_2SO_4$ = | Sulfuric acid |
| HMPA = | hexamethylphosphoramide |
| Hz = | Hertz |
| $I_2$ = | Iodine |
| $K_2CO_3$ = | Potassium carbonate |
| KF = | Potassium fluoride |
| KOtBu = | Potassium tert-butoxide |
| $K_3PO_4$ = | Potassium phosphate |
| L = | Liter |
| LDA = | Lithium diisopropylamide |
| M = | Molar |
| m = | Multiplet |
| m/z = | Mass to charge ratio |
| $Me_4Sn$ = | Tetramethyltin (IV) |
| MeOH = | Methanol |
| mg = | Milligram |
| $MgSO_4$ = | Magnesium sulfate |
| MHz = | Mega Hertz |
| min = | Minute |
| mL = | Milliliter |
| mM = | Millimolar |
| mmol = | Millimole |
| mol = | Mole |
| MPLC = | Medium pressure liquid chromatography |
| MS = | Mass spectroscopy |
| MTBE = | Methyl tert-butyl ether |
| N = | Normal |
| $NaHCO_3$ = | Sodium bicarbonate |
| NaCl = | Sodium chloride |
| NaH = | Sodium hydride |
| $Na_2S_2O_3$ = | Sodium thiosulfate |
| NaOMe = | Sodium methoxide |
| NBS = | N-bromosuccinimide |
| $n-Bu_3SnPh$ = | Tri-n-butylphenyl tin (IV) |
| $NEt_3$ = | Triethylamine |
| NMP = | 1-Methyl-2-pyrrolidinone |
| NMR = | Nuclear magnetic resonance |
| $PPh_3$ = | Triphenyl phosphine |
| $Pd(PPh_3)_2Cl_2$ = | Dichlorobis(triphenylphosphine)palladium (II), |
| $Pd(PPh_3)_4$ = | tetrakis(triphenylphosphine)palladium(0) |
| Pd/C = | Palladium over carbon |
| q = | Quartet |
| rt = | Room temperature |
| s = | Singlet |
| $SOCl_2$ = | Thionyl chloride |
| $SO_3$ = | Sulfur trioxide |
| t = | Triplet |
| TFA = | Trifluoroacetic acid |
| THF = | Tetrahydrofuran |
| TLC = | Thin layer chromatography |
| TSOH = | p-Toluenesulfonic acid |
| xg = | Times gravity |

Example 1

[(7-Hydroxy-2-phenyl-oxazolo[4,5-c]pyridine-6-carbonyl)-amino]-acetic acid a) 4-Bromomethyl-2-phenyl-oxazole-5-carboxylic acid methyl ester 4-Methyl-2-phenyl-oxazole-5-carboxylic acid methyl ester (3.2 g, 14.7 mmol, prepared according to Cynkowski, T.; Cynkowska, G.; Ashton, P.; and Crooks, P. A. *J. Chem. Soc., Chem. Commun.* 1995, 2335), N-bromosuccinimide (2.69 g, 15.1 mmol), and benzoyl peroxide (356 mg, 1.47 mmol) were suspended in 37 mL of benzene and the mixture heated at reflux temperature for 16 hours. The reaction mixture was cooled and diluted with ethyl acetate. The mixture was washed successively with saturated bicarbonate solution, brine, saturated ammonium chloride solution, and brine. The organic solvent was dried, filtered, and concentrated. The crude product was purified by flash chromatography eluting from silica gel with a gradient of 0-40% ethyl acetate in hexanes to give 1.88 g of the title compound as a yellow solid. MS: (+) m/z 296.0, 298.0 (M+1, $^{79}$Br/$^{81}$Br).

b) 4-{[2,4-Dimethoxy-benzyl)-methoxycarbonylmethyl-amino]-methyl}-2-phenyl oxazole-5-carboxylic acid methyl ester 4-Bromomethyl-2-phenyl-oxazole-5-carboxylic acid methyl ester (1.88 g, 6.35 mmol) was dissolved in 16 mL of dry N,N-dimethylformamide. N-(2,4-dimethoxy-benzyl) glycine ethyl ester (1.52 g, 6.35 mmol) and potassium carbonate (0.97 g, 6.99 mmol) were added and the reaction mixture was stirred at room temperature for 18 hours. The reaction mixture was diluted with ethyl acetate and washed with water and brine. The organic phase was dried over anhydrous sodium sulfate, and concentrated. The residue was purified by flash chromatography eluting from silica gel with a gradient of 0-100% ethyl acetate in hexanes to produce 2.46 g of a tan oil. MS: (+) m/z 455.0 (M+1).

c) 5-(2,4-Dimethoxy-benzyl)-7-oxo-2-phenyl-4,5,6,7-tetrahydro-oxazolo[4,5-d]pyridine-6-carboxylic acid methyl ester 4-{[2,4-Dimethoxy-benzyl)-methoxycarbonylmethyl-amino]-methyl}-2-phenyl-oxazole-5-carboxylic acid methyl ester (1.96 g, 4.31 mmol), was dissolved in 43 mL of anhydrous THF and cooled to −15° C. in a brine/dry ice bath. A solution of 9.49 mL of 1.0 M potassium tert-butoxide in THF was added slowly, and the reaction mixture was stirred at −15° C. for 30 min. and then at room temperature for 2 hours. The reaction was quenched with 9.49 mL of 1N HCl and 150 mL of a saturated aqueous ammonium chloride solution, and extracted twice with 150 mL of ethyl acetate. The combined organic phases were washed with brine, dried over anhydrous sodium sulfate and concentrated. The residue was purified by flash chromatography eluting from silica gel with a gradient of 0-80% ethyl acetate in hexanes to give 0.92 g of the title compound as a yellow froth. MS: (+) m/z 445.1 (M+Na$^+$).

d) 7-Hydroxy-2-phenyl-oxazolo[4,5-c]pyridine-6-carboxylic acid methyl ester 5-(2,4-Dimethoxy-benzyl)-7-oxo-2-phenyl-4,5,6,7-tetrahydro-oxazolo[4,5-c]pyridine-6-carboxylic acid methyl ester (1.05 g, 2.49 mmol), was dissolved in 17 mL of anhydrous dichloromethane. To the solution was added 272 μL of thionyl chloride, and the reaction was stirred for 5 hours. The solution was filtered on a fine glass frit filter to collect a white solid precipitate. The solid was washed twice with cold dichloromethane and then partitioned between saturated sodium bicarbonate solution and ethyl acetate. The organic phase was washed with brine, dried over anhydrous sodium sulfate, and concentrated to give 0.20 g of the title compound as a white solid. MS: (−) m/z 269.1 (M−1).

e) [(7-Hydroxy-2-phenyl-oxazolo[4,5-c]pyridine-6-carbonyl)-amino]-acetic acid

7-Hydroxy-2-phenyl-oxazolo[4,5-c]pyridine-6-carboxylic acid methyl ester (100 mg, 0.37 mmol), and glycine (583 mg, 7.77 mmol) were suspended in 14.8 mL of 0.5N sodium methoxide in methanol. The reaction mixture was heated at reflux temperature overnight, then cooled, and concentrated. The residue was dissolved in water (30 mL), and the solution was acidified to pH 1-2 with 2N HCl, and subsequently extracted with ethyl acetate. The combined organic layers were dried, and concentrated to produce 104 mg of the title compound as a yellow solid. MS: (+) m/z 314.0 (M+1).

Example 2

{[2-(4-Fluoro-phenyl)-7-hydroxy-oxazolo[4,5-c] pyridine-6-carbonyl]-amino}-acetic acid a) 2-(4-fluoro-phenyl)-4-methyl-oxazole-5-carboxylic acid methyl ester A solution of 4-fluorobenzamide (12 g, 86.3 mmol) and methyl 2-chloroacetoacetate (10.5 mL, 86.3 mmol) in ethanol (120 mL) was refluxed overnight. Subsequently the reaction mixture was concentrated in vacuo and the residue was dissolved in ethyl acetate. The organic solution was washed with saturated sodium bicarbonate solution and brine, dried, and concentrated in vacuo. The residue was purified by flash chromatography eluting from silica gel with a gradient of 0-50% ethyl acetate in hexanes to give 2.08 g of the title compound as a white solid. MS: (+) m/z 236.2 (M+1).

b) 4-Bromomethyl-2-(4-fluoro-phenyl)-oxazole-5-carboxylic acid methyl ester

Prepared from 2-(4-fluoro-phenyl)-4-methyl-oxazole-5-carboxylic acid methyl ester under conditions analogous to example 1a. MS: (+) m/z 314.1, 315.8 (M+1, $^{79}$Br/$^{81}$Br).

c) 4-{[2,4-Dimethoxy-benzyl)-methoxycarbonylmethyl-amino]-methyl}-2-(4-fluoro-phenyl)-oxazole-5-carboxylic acid methyl ester Prepared from 4-bromomethyl-2-(4-fluoro-phenyl-oxazole-5-carboxylic acid methyl ester under conditions analogous to example 1b. MS: (+) m/z 495.2 (M+Na$^+$).

d) 5-(2,4-Dimethoxy-benzyl)-2-(4-fluoro-phenyl)-7-oxo-4,5,6,7-tetrahydro-oxazolo[4,5-c]pyridine-6-carboxylic acid methyl ester Prepared from 4-{[2,4-dimethoxy-benzyl)-methoxycarbonylmethyl-amino]-methyl}-2-(4-fluoro-phenyl)-oxazole-5-carboxylic acid methyl ester under conditions analogous to example 1c. MS: (+) m/z 461.0 (M+Na$^+$).

e) 2-(4-Fluoro-phenyl)-7-hydroxy-oxazolo[4,5-c] pyridine-6-carboxylic acid methyl ester Prepared from 5-(2,4-dimethoxy-benzyl)-2-(4-fluoro-phenyl)-7-oxo-4,5,6,7-tetrahydro-oxazolo[4,5-c]pyridine-6-carboxylic acid methyl ester under conditions analogous to example 1d. MS: (+) m/z 289.0 (M+1).

f) {[2-(4-Fluoro-phenyl)-7-hydroxy-oxazolo[4,5-c] pyridine-6-carbonyl]-amino}-acetic acid Prepared from 2-(4-fluoro-phenyl)-7-hydroxy-oxazolo[4,5-c]pyridine-6-carboxylic acid methyl ester under conditions analogous to example 1e. MS: (−) m/z 330.0 (M−1).

Example 3

[(7-Hydroxy-4-methyl-2-phenyl-oxazolo[4,5-c]pyridine-6-carbonyl)-amino]-acetic acid a) 4-Bromo-7-hydroxy-2-phenyl-oxazolo[4,5-c]pyridine-6-carboxylic acid methyl ester A suspension of 7-hydroxy-2-phenyl-oxazolo[4,5-c]pyridine-6-carboxylic acid methyl ester (3.57 g, 13.2 mmol; example 1d), N-bromosuccinimide (2.47 g, 13.9 mmol), and benzoyl peroxide (320 mg, 1.32 mmol) in 43 mL of benzene was heated at reflux temperature for 5 hours. The reaction mixture was washed successively with saturated sodium bicarbonate, brine, saturated ammonium chloride solution, and brine. The organic solution was dried, filtered, and concentrated. The residue was purified by flash chromatography eluting from silica gel with a gradient of 0-25% methanol in methylene chloride to give 2.81 g of the title compound as a light yellow solid. MS: (+) m/z 348.9, 350.9 (M+1, $^{79}$Br/$^{81}$Br).

b) 7-Hydroxy-4-methyl-2-phenyl-oxazolo[4,5-c]pyridine-6-carboxylic acid methyl ester Under a nitrogen atmosphere, a mixture of 4-bromo-7-hydroxy-2-phenyl-oxazolo[4,5-c]pyridine-6-carboxylic acid methyl ester (200 mg, 0.573 mmol), tetramethyltin (0.32 mL, 2.29 mmol), and dichlorobis(triphenylphosphine)palladium (II) (40.2 mg, 0.057 mmol) was suspended in 4.8 mL of anhydrous N,N-dimethylformamide. The reaction mixture was heated at 130° C. for 1 hour, cooled to room temperature, and diluted with ethyl acetate. The organic mixture was successively washed with saturated sodium bicarbonate solution, brine, saturated ammonium chloride solution, and brine. The organic phase was dried over anhydrous sodium sulfate and concentrated. The residue was purified by flash chromatography eluting from silica gel with a gradient of 0-100% ethyl acetate in hexanes to give 99.6 mg of the title compound as a white solid. MS: (+) m/z 285.0 (M+1).

c) [(7-Hydroxy-4-methyl-2-phenyl-oxazolo[4,5-c]pyridine-6-carbonyl)-amino]-acetic acid Prepared from 7-hydroxy-4-methyl-2-phenyl-oxazolo[4,5-c]pyridine-6-carboxylic acid methyl ester under conditions analogous to example 1e. MS: (+) m/z 328.0 (M+1).

Example 4

[(4-Ethyl-7-hydroxy-2-phenyl-oxazolo[4,5-c]pyridine-6-carbonyl)-amino]-acetic acid a) 4-Ethyl-7-hydroxy-2-phenyl-oxazolo[4,5-c]pyridine-6-carboxylic acid methyl ester Prepared from 4-bromo-7-hydroxy-2-phenyl-oxazolo[4,5-c]pyridine-6-carboxylic acid methyl ester, example 3a, and tetraethyltin under conditions analogous to example 3b. MS: (+) m/z 299.1 (M+1).

b) [(4-Ethyl-7-hydroxy-2-phenyl-oxazolo[4,5-c]pyridine-6-carbonyl)-amino]-acetic acid Prepared from 4-ethyl-7-hydroxy-2-phenyl-oxazolo[4,5-c]pyridine-6-carboxylic acid methyl ester under conditions analogous to example 1e. MS: (−) m/z 340.1 (M−1).

Example 5

[(7-Hydroxy-2,4-diphenyl-oxazolo[4,5-c]pyridine-6-carbonyl)-amino]-acetic acid a) 7-Hydroxy-2,4-diphenyl-oxazolo[4,5-c]pyridine-6-carboxylic acid methyl ester Prepared from 4-bromo-7-hydroxy-2-phenyl-oxazolo[4,5-c]pyridine-6-carboxylic acid methyl ester, example 3a, and tributylphenyltin under conditions analogous to example 3b. MS: (+) m/z 347.1 (M+1).

b) [(7-Hydroxy-2,4-diphenyl-oxazolo[4,5-c]pyridine-6-carbonyl)-amino]-acetic acid Prepared from 7-hydroxy-2,4-diphenyl-oxazolo[4,5-c]pyridine-6-carboxylic acid methyl ester, under conditions analogous to experimental example 1e. MS: (−) m/z 388.0 (M−1).

Example 6

[(7-Hydroxy-2-phenyl-4-phenylethynyl-oxazolo[4,5-c]pyridine-6-carbonyl)-amino]-acetic acid a) 7-Hydroxy-2-phenyl-4-phenylethynyl-oxazolo[4,5-c]pyridine-6-carboxylic acid methyl ester Prepared from 4-bromo-7-hydroxy-2-phenyl-oxazolo[4,5-c]pyridine-6-carboxylic acid methyl ester, example 3a, and tributyl(phenylethynyl)tin under conditions analogous to experimental example 3b. MS: (+) m/z 370.9 (M+1).

b) [(7-Hydroxy-2-phenyl-4-phenylethynyl-oxazolo[4,5-c]pyridine-6-carbonyl)-amino]-acetic acid Prepared from 7-hydroxy-2-phenyl-4-phenylethynyl-oxazolo[4,5-c]pyridine-6-carboxylic acid methyl ester under conditions analogous to example 1e. MS: (+) m/z 413.9 (M+1).

Example 7

[(4-Butyl-7-hydroxy-2-phenyl-oxazolo[4,5-c]pyridine-6-carbonyl)-amino]-acetic acid a) 4-Butyl-7-hydroxy-2-phenyl-oxazolo[4,5-c]pyridine-6-carboxylic acid methyl ester Prepared from 4-bromo-7-hydroxy-2-phenyl-oxazolo[4,5-c]pyridine-6-carboxylic acid methyl ester, example 3a, and tetrabutyltin under conditions analogous to example 3b. MS: (+) m/z 327.0 (M+1).

b) [(4-Butyl-7-hydroxy-2-phenyl-oxazolo[4,5-c]pyridine-6-carbonyl)-amino]-acetic acid Prepared from 4-butyl-7-hydroxy-2-phenyl-oxazolo[4,5-c]pyridine-6-carboxylic acid methyl ester under conditions analogous to example 1e. MS: (+) m/z 369.9 (M+1).

Example 8

{[4-(4-Fluoro-phenyl)-7-hydroxy-2-phenyl-oxazolo[4,5-c]pyridine-6-carbonyl]-amino}-acetic acid a) 4-(4-Fluoro-phenyl)-7-hydroxy-2-phenyl-oxazolo[4,5-c]pyridine-6-carboxylic acid methyl ester Prepared from 4-bromo-7-hydroxy-2-phenyl-oxazolo[4,5-c]pyridine-6-carboxylic acid methyl ester, example 3a, and tributyl(4-fluorophenyl)stannane under conditions analogous to example A-3b. MS: (+) m/z 364.9 (M+1).

b) {[4-(4-Fluoro-phenyl)-7-hydroxy-2-phenyl-oxazolo[4,5-c]pyridine-6-carbonyl]-amino}-acetic acid Prepared from 4-(4-fluoro-phenyl)-7-hydroxy-2-phenyl-oxazolo[4,5-c]pyridine-6-carboxylic acid methyl ester under conditions analogous to example 1e. MS: (+) m/z 405.9 (M−1).

Example 9

[(7-Hydroxy-2-phenyl-oxazolo[5,4-c]pyridine-6-carbonyl)-amino]-acetic acid a) 5-Bromomethyl-2-phenyl-oxazole-4-carboxylic acid methyl ester Prepared from 5-methyl-2-phenyl-oxazole-4-carboxylic acid methyl ester (prepared according to Wipf, P.; Cunningham, A.; Rice, R. L.; and Lazo, J. S. Bioorg. Med. Chem. 1997, 5, 165) under conditions analogous to example 1a. MS: (+) m/z 295.9, 297.9 (M+1, $^{79}$Br/$^{81}$Br).

b) 5-{[2,4-Dimethoxy-benzyl)-methoxycarbonylmethyl-amino]-methyl}-2-phenyl-oxazole-4-carboxylic acid methyl ester Prepared from 5-bromomethyl-2-phenyl-oxazole-4-carboxylic acid methyl ester under conditions analogous to example 1b. MS: (+) m/z 477.2 (M+Na$^+$).

c) 5-(2,4-Dimethoxy-benzyl)-7-oxo-2-phenyl-4,5,6,7-tetrahydro-oxazolo[5,4-c]pyridine-6-carboxylic acid methyl ester Prepared from 5-{[2,4-dimethoxy-benzyl)-methoxycarbonylmethyl-amino]-methyl}-2-phenyl-oxazole-4-carboxylic acid methyl ester under conditions analogous to example 1c. MS: (+) m/z 445.1 (M+Na$^+$).

d) 7-Hydroxy-2-phenyl-oxazolo[5,4-c]pyridine-6-carboxylic acid methyl ester

Prepared from 5-(2,4-dimethoxy-benzyl)-7-oxo-2-phenyl-4,5,6,7-tetrahydro-oxazolo[5,4-c]pyridine-6-carboxylic acid methyl ester under conditions analogous to example 1d. MS: (+) m/z 271.0 (M+1).

e) [(7-Hydroxy-2-phenyl-oxazolo[5,4-c]pyridine-6-carbonyl)-amino]-acetic acid

Prepared from 7-hydroxy-2-phenyl-oxazolo[5,4-c]pyridine-6-carboxylic acid methyl ester under conditions analogous to example 1e. MS: (−) m/z 312.0 (M−1).

Example 10

{[7-Hydroxy-4-(3-methoxy-phenyl)-2-phenyl-oxazolo[4,5-c]pyridine-6-carbonyl]-amino}-acetic acid a) 4-Bromo-7-(2,2-dimethyl-propionyloxy)-2-phenyl-oxazolo[4,5-c]pyridine-6-carboxylic acid methyl ester A solution of 4-bromo-7-hydroxy-2-phenyl-oxazolo[4,5-c]pyridine-6-carboxylic acid methyl ester (0.1 g, 0.286 mmol; example 3a), trimethylacetyl chloride (42.3 µL, 0.344 mmol), triethylamine (79.7 µL, 0.572 mmol), and 4-(dimethylamino)pyridine (3.5 mg, 0.03 mmol) in methylene chloride (2.5 mL) was stirred at room temperature for 2 hours. The reaction mixture was diluted with ethyl acetate and washed with saturated sodium bicarbonate solution, brine, saturated ammonium chloride solution, and brine. The organic fraction was dried over anhydrous sodium sulfate, and concentrated. The crude product was purified by flash chromatography eluting from silica gel with a gradient of 0-70% ethyl acetate in hexanes to give 51 mg of the title compound as a white solid. MS: (+) m/z 432.8, 434.8 (M+1, $^{79}$Br/$^{81}$Br).

b) 7-(2,2-Dimethyl-propionyloxy)-4-(3-methoxy-phenyl)-2-phenyl-oxazolo[4,5-c]pyridine-6-carboxylic acid methyl ester and 7-hydroxy-4-(3-methoxy-phenyl)-2-phenyl-oxazolo[4,5-c]pyridine-6-carboxylic acid methyl ester Under a nitrogen atmosphere 4-bromo-7-(2,2-dimethyl-propionyloxy)-2-phenyl-oxazolo[4,5-c]pyridine-6-carboxylic acid methyl ester (51 mg, 0.12 mmol), 3-methoxyphenylboronic acid (21.5 mg, 0.14 mmol), potassium carbonate (58.7 mg, 0.43 mmol), and tetrakis(triphenylphosphine)palladium(0) (20.4 mg, 0.018 mmol) were suspended in 3 mL of anhydrous 1,4-dioxane. The reaction mixture was heated at 100° C. for 16 hours, then cooled to room temperature, and diluted with ethyl acetate. The mixture was successively washed with water, saturated sodium bicarbonate, and brine solutions. The organic fraction was dried over anhydrous sodium sulfate and concentrated. The residue was purified by flash chromatography eluting from silica gel with a gradient of 0-50% ethyl acetate in hexanes to give 7.5 mg of 7-(2,2-Dimethyl-propionyloxy)-4-(3-methoxy-phenyl)-2-phenyl-oxazolo[4,5-c]pyridine-6-carboxylic acid methyl ester and 24.7 mg of 7-hydroxy-4-(3-methoxy-phenyl)-2-phenyl-oxazolo[4,5-c]pyridine-6-carboxylic acid methyl ester.

MS for 7-(2,2-dimethyl-propionyloxy)-4-(3-methoxy-phenyl)-2-phenyl-oxazolo[4,5-c]pyridine-6-carboxylic acid methyl ester: (+) m/z 460.9 (M+1).

MS for 7-hydroxy-4-(3-methoxy-phenyl)-2-phenyl-oxazolo[4,5-c]pyridine-6-carboxylic acid methyl ester: (+) m/z 377.0 (M+1).

c) {[7-Hydroxy-4-(3-methoxy-phenyl)-2-phenyl-oxazolo[4,5-c]pyridine-6-carbonyl]-amino}-acetic acid Sodium methoxide methanol solution (0.5 N, 0.4 mL, 0.2 mmol) was added to a solution of 7-(2,2-dimethyl-propionyloxy)-4-(3-methoxy-phenyl)-2-phenyl-oxazolo[4,5-c]pyridine-6-carboxylic acid methyl ester (7.5 mg, 0.016 mmol), and 7-hydroxy-4-(3-methoxy-phenyl)-2-phenyl-oxazolo[4,5-c]pyridine-6-carboxylic acid methyl ester (24.7 mg, 0.066 mmol) in methanol (2 mL) at room temperature. After the reaction mixture was refluxed for 1 hour, the mixture was concentrated. To the residue glycine (0.129 g, 1.72 mmol) and sodium methoxide methanol solution (0.5 N, 2.88 mL, 1.44 mmol) were then added. The mixture was then refluxed overnight, cooled, and concentrated. The residue was dissolved in water (30 mL), and the solution was washed with ethyl acetate (3×20 mL). After the solution was acidified to pH 1-2 with 2N HCl, a light yellow solid precipitated, that was collected by filtration and then dried in vacuo to give 23.5 mg of the title compound. MS: (−) m/z 417.9 (M−1).

Example 11

[(4-Hydroxy-3-phenyl-isoxazolo[5,4-c]pyridine-5-carbonyl)-amino]-acetic acid a) 5-Methyl-3-phenyl-isoxazole-4-carboxylic acid ethyl ester A mixture of 5-methyl-3-phenyl-isoxazole-4-carboxylic acid (10.0 g, 0.05 mol) and thionyl chloride (18.0 ml, 0.25 mol) in ethanol (100 ml) was refluxed for 5 h before it was cooled to room temperature and concentrated in vacuo. The residue was partitioned between ethyl acetate and water, the organic layer was washed with saturated aqueous sodium bicarbonate solution, and brine, before it was dried over anhydrous sodium sulfate and concentrated in vacuo to give the title compound as a yellow solid (10.24 g): $^1$H NMR (CDCl$_3$, 200 MHz): δ=7.61 (m, 2H), 7.43 (m, 3H), 4.25 (q, J=7.0 Hz, 2H), 2.73 (s, 3H), 1.23 (t, J=7.0 Hz, 3H).

b) 5-Bromomethyl-3-phenyl-isoxazole-4-carboxylic acid ethyl ester

A mixture of 5-methyl-3-phenyl-isoxazole-4-carboxylic acid ethyl ester (5.02 g, 0.02 mol), N-bromosuccinimide (4.06 g, 0.02 mmol) and benzoyl peroxide (263 mg, 1.09 mmol) in carbon tetrachloride (80 ml) was refluxed for 20 h before it was cooled to room temperature and partitioned between dichloromethane and water. The organic layer was washed with saturated aqueous sodium bicarbonate solution, and brine before it was dried over anhydrous sodium sulfate and concentrated in vacuo to give the crude title compound as a yellow oil (6.35 g) that was used in the following step without further purification: $^1$H NMR (CDCl$_3$, 200 MHz): δ=7.61 (m, 2H), 7.43 (m, 3H), 4.80 (s, 2H), 4.25 (q, J=7.0 Hz, 2H), 1.26 (t, J=7.0 Hz, 3H).

c) N-(2,4-dimethoxy-benzyl)-N-(ethyl ethanylat-2-yl)-5-aminomethyl-3-phenyl-isoxazole-4-carboxylic acid ethyl ester A mixture of 5-bromomethyl-3-phenyl-isoxazole-4-carboxylic acid ethyl ester (1.05 g, 3.40 mmol), (2,4-dimethoxy-benzylamino)-acetic acid ethyl ester (816 mg, 3.22 mmol) and potassium carbonate (567 mg, 4.10 mmol) in anhydrous dimethylformamide (15 ml) was stirred at room temperature for three days before it was quenched with water, extracted with ethyl acetate. The organic layer was washed with water, brine, dried over anhydrous sodium sulfate and concentrated in vacuo. The residue was purified by flash column chromatography on silica gel with a gradient of ethyl acetate and hexanes to give the title compound as a yellow oil (954 mg): MS: (+) m/z 505.27 (M+Na$^+$).

d) 4-Hydroxy-3-phenyl-isoxazolo[5,4-c]pyridine-5-carboxylic acid ethyl ester

To a yellow solution of N-(2,4-dimethoxy-benzyl)-N-(ethyl ethanylat-2-yl)-5-aminomethyl-3-phenyl-isoxazole-4-carboxylic acid ethyl ester (931 mg, 1.93 mmol) in THF (8 ml) was added 1 M KO'Bu in THF (4.2 ml, 4.25 mmol) at −78° C. The mixture was stirred at −78° C. for 20 min, then warmed to room temperature and stirred at that temperature for 2 h before it was quenched with aqueous ammonium chloride solution and extracted with ethyl acetate. The organic layer was washed with water and brine before it was dried over anhydrous sodium sulfate and concentrated in vacuo to give a yellow oil (623.4 mg). Subsequently, the oil was dissolved in dichloromethane (6 ml) and a solution of thionyl chloride (1.4 ml, 2M in dichloromethane) was added dropwise. The mixture was stirred at room temperature for 2 h before it was quenched with saturated sodium bicarbonate and extracted with dichloromethane. The organic layer was washed with water and brine before it was dried over anhydrous sodium sulfate and concentrated in vacuo. The residue was purified by flash column chromatography on silica gel with a gradient of dichloromethane and hexanes to give the title compound as a yellow solid (174 mg): MS: (−) m/z 283.20 (M−1).

e) [(4-Hydroxy-3-phenyl-isoxazolo[5,4-c]pyridine-5-carbonyl)-amino]-acetic acid

A mixture of 4-hydroxy-3-phenyl-isoxazolo[5,4-c]pyridine-5-carboxylic acid ethyl ester (61 mg, 0.21 mmol), glycine (322 mg, 4.29 mmol), and a 0.5 M solution of sodium methoxide in methanol (8.1 ml) was refluxed for 20 h before it was cooled to room temperature and concentrated in vacuo. The residue was dissolved in water (15 ml) and the solution was extracted with methyl t-butyl ether (2×20 ml). The remaining aqueous layer was acidified to pH=3 with 1N HCl. The resulting precipitate was filtered, washed with water and dried in vacuo to give the title compound as a white solid (26 mg): $^1$H NMR (DMSO-d$_6$, 200 MHz): δ=9.47 (br s, 1H), 8.82 (s, 1H), 8.04 (m, 2H), 7.59 (m, 3H), 4.01 (d, J=6.4 Hz, 2H); MS: (+) m/z 314.07 (M+1), (−) m/z 312.20 (M−1).

Example 12

[(4-Hydroxy-7-methyl-3-phenyl-isoxazolo[5,4-c]pyridine-5-carbonyl)-amino]-acetic acid a) 7-Bromo-4-hydroxy-3-phenyl-isoxazolo[5,4-c]pyridine-5-carboxylic acid ethyl ester A mixture of 4-hydroxy-3-phenyl-isoxazolo[5,4-c]pyridine-5-carboxylic acid ethyl ester (388.1 mg, 1.37 mmol), N-bromosuccinimide (255 mg, 1.43 mmol), benzoyl peroxide (16 mg, 0.07 mmol), and carbon tetrachloride (10 ml) was refluxed for 3 h before it was cooled to room temperature and partitioned between dichloromethane and water. The organic layer was washed with saturated aqueous sodium bicarbonate solution and brine before it was dried over anhydrous sodium sulfate and concentrated in vacuo. The residue was purified by flash column chromatography on silica gel with a gradient of ethyl acetate and dichloromethane to give the title compound as a white solid (432 mg): MS: (−) m/z 361.21, 363.23 (M−1, $^{79}$Br/$^{81}$Br).

b) 4-Hydroxy-7-methyl-3-phenyl-isoxazolo[5,4-c]pyridine-5-carboxylic acid ethyl ester A mixture of 7-bromo-4-hydroxy-3-phenyl-isoxazolo[5,4-c]pyridine-5-carboxylic acid ethyl ester (231 mg, 0.64 mmol), tetramethyltin (177 µl, 1.28 mmol), bis(triphenylphosphine)palladium(II) dichloride (45 mg, 0.06 mmol), and dimethylformamide (2.5 ml) was stirred at 130° C. for 1 h before it was cooled to room temperature, quenched with water, and filtered. The filtrate was partitioned between ethyl acetate and water. The organic layer was washed with brine, dried over anhydrous sodium sulfate and concentrated in vacuo. The residue was purified by flash column chromatography on silica gel with a gradient of ethyl acetate and dichloromethane to give the title compound as a white solid (95 mg): MS: (+) m/z 299.49 (M+1).

c) [(4-Hydroxy-7-methyl-3-phenyl-isoxazolo[5,4-c] pyridine-5-carbonyl)-amino]-acetic acid A mixture of 4-hydroxy-7-methyl-3-phenyl-isoxazolo[5,4-c]pyridine-5-carboxylic acid ethyl ester (93 mg, 0.31 mmol), glycine (470 mg, 6.27 mmol), and a 0.5 M solution sodium methoxide in methanol (11.9 ml) was refluxed for 42 h before it was cooled to room temperature and concentrated in vacuo. The residue was dissolved in water (20 ml) and the solution was extracted with methyl t-butyl ether (2×25 ml). The remaining aqueous layer was acidified to pH=3 with 1N HCl. The resulting precipitate was filtered, washed with water and dried in vacuo to give the title compound as a gray solid (89 mg): $^1$H NMR (DMSO-$d_6$, 200 MHz): δ=9.25 (t, 1H), 8.03 (m, 2H), 7.57 (m, 3H), 4.01 (d, J=6.2 Hz, 2H), 2.71 (s, 3H); MS: (+) m/z 327.98 (M+1), (−) m/z 325.99 (M−1).

Example 13

[(4-Hydroxy-3,7-diphenyl-isoxazolo[5,4-c]pyridine-5-carbonyl)-amino]-acetic acid a) 4-Hydroxy-3,7-diphenyl-isoxazolo[5,4-c]pyridine-5-carboxylic acid ethyl ester A mixture of 7-bromo-4-hydroxy-3-phenyl-isoxazolo[5,4-c]pyridine-5-carboxylic acid ethyl ester (125.4 mg, 0.35 mmol), phenylboronic acid (85 mg, 0.69 mmol), cesium carbonate (339 mg, 1.04 mmol), tetrakis(triphenylphosphine) palladium (40 mg, 0.03 mmol), and dioxane (1.5 ml) was refluxed for 18 h before it was cooled to room temperature and quenched with water. It was partitioned between ethyl acetate and water. The organic layer was washed with brine, dried over anhydrous sodium sulfate and concentrated in vacuo. The residue was purified by flash column chromatography on silica gel with a gradient of ethyl acetate and dichloromethane to give the title compound as a white solid (63 mg): MS: (+) m/z 361.07 (M+1).

b) [(4-Hydroxy-3,7-diphenyl-isoxazolo[5,4-c]pyridine-5-carbonyl)-amino]-acetic acid A mixture of 4-hydroxy-3,7-diphenyl-isoxazolo[5,4-c]pyridine-5-carboxylic acid ethyl ester (86 mg, 0.24 mmol), glycine (360 mg, 4.79 mmol), and a 0.5 M solution of sodium methoxide in methanol (9.1 ml) was refluxed for three days before it was cooled to room temperature and concentrated in vacuo. The residue was dissolved in water (20 ml) and the resulting solution extracted with methyl t-butyl ether (3×25 ml). The remaining aqueous layer was acidified to pH=3 with 1N HCl. The resulting precipitate was filtered, washed with water and dried in vacuo to give the title compound as a white solid (80 mg): $^1$H NMR (DMSO-$d_6$, 200 MHz): δ=9.25 (t, 1H), 8.03 (m, 2H), 7.57 (m, 3H), 4.01 (d, J=6.2 Hz, 2H), 2.71 (s, 3H); MS: (+) m/z 390.27 (M+1).

Example 14

{[3-(4-Chloro-phenyl)-4-hydroxy-isoxazolo[5,4-c] pyridine-5-carbonyl]-amino}-acetic acid a) 4-chloro-benzaldehyde oxime To a suspension of 4-chlorobenzaldehyde (70 g, 0.50 mol) and hydroxylamine hydrochloride (38.06 g, 0.55 mol) in a mixture of water (125 ml), methanol (150 ml) and ice (215 ml) was added an aqueous solution of sodium hydroxide (43.82 g NaOH in 100 ml water). Ice was occasionally added to keep the temperature below room temperature. The resulting almost clear solution was stirred for two hours before it was extracted with methyl t-butyl ether (500 ml). The remaining aqueous layer was acidified with 6 N HCl (95 ml) to pH around 5. The suspension was extracted with dichloromethane (500 ml). The organic phase was dried and concentrated to give the title compound as a white solid (63.39 g): NMR (CDCl$_3$, 200 MHz): δ=8.09 (s, 1H), 7.66 (br s, 1H), 7.49 (m, 2H), 7.34 (m, 2H).

b) 4-chloro-N-hydroxy-benzimidoyl chloride

To a solution of 4-chloro-benzaldehyde oxime (20 g, 0.13 mol) in anhydrous dimethylformamide (80 ml) was added N-chlorosuccinimide (3.51 g, 0.03 mol, 0.2 eq) at room temperature. Subsequently, HCl gas drawn from the headspace of concentrated hydrochloric acid was bubbled through the reaction mixture. Then, additional N-chlorosuccinimide (14.06 g, 0.11 mol, 0.8 eq) was then added in four portions and the mixture was stirred at room temperature for twenty hours before it was poured into ice-water (200 ml) and extracted twice with methyl t-butyl ether. The combined organic layers were washed with water and brine, and then dried and concentrated to give the title compound as a white solid (23.26 g): $^1$H NMR (CDCl$_3$, 200 MHz): δ=7.97 (s, 1H), 7.77 (m, 2H), 7.36 (m, 2 H). $^{13}$C NMR (CDCl$_3$, 50 MHz): δ=139.37, 137.10, 130.99, 128.94, 128.57 c) 3-(4-Chloro-phenyl)-5-methyl-isoxazole-4-carboxylic acid ethyl ester

To a suspension of 4-chloro-N-hydroxy-benzimidoyl chloride (1.11 g, 5.88 mmol) in dry ethanol (9 ml) was added a solution of ethyl (E)-3-(1-pyrrolidino)crotonate (1.08 g, 5.88 mmol) and triethylamine (492 μl, 3.53 mmol) in dry ethanol (9 ml) over a period of twenty minutes at room temperature. The suspension was stirred for eighteen hours before the mixture was concentrated and the residue partitioned between ethyl acetate and water. The organic layer was washed with 0.5 N HCl and brine, before it was dried and concentrated in vacuo. The residue was purified by flash column chromatography with a gradient of ethyl acetate and hexanes on silica gel (40 g) to give the title compound as a white solid (1.09 g): $^1$H NMR (CDCl$_3$, 200 MHz): δ=7.57 (m, 2H), 7.42 (m, 2H), 4.25 (q, J=7.0 Hz, 2H), 2.74 (s, 3H), 1.27 (t, J=7.0 Hz, 3H); MS: (+) m/z 266.31 (M+1).

d) 5-Bromomethyl-3-(4-chloro-phenyl)-isoxazole-4-carboxylic acid ethyl ester

Prepared in analogy to Example 11 from 3-(4-chloro-phenyl)-5-methyl-isoxazole-4-carboxylic acid ethyl ester; ESI MS (m/z): 344.17, 346.17 (M+H$^+$, $^{79}$Br/$^{81}$Br).

e) N-(2,4-Dimethoxy-benzyl)-N-(ethyl ethanylat-2-yl)-5-aminomethyl-3-(4-chloro-phenyl)-isoxazole-4-carboxylic acid ethyl ester Prepared in analogy to Example 11 from 5-bromomethyl-3-(4-chloro-phenyl)-isoxazole-4-carboxylic acid ethyl ester; ESI MS (m/z): 517.33 (M+H$^+$).

f) 3-(4-Chloro-phenyl)-4-hydroxy-isoxazolo[5,4-c]pyridine-5-carboxylic acid ethyl ester Prepared in analogy to Example 11 from N-(2,4-Dimethoxy-benzyl)-N-(ethyl ethanylat-2-yl)-5-aminomethyl-3-(4-chloro-phenyl)-isoxazole-4-carboxylic acid ethyl ester; ESI MS (m/z): 319.27 (M+H$^+$).

g) {[3-(4-Chloro-phenyl)-4-hydroxy-isoxazolo[5,4-c]pyridine-5-carbonyl]-amino}-acetic acid Prepared in analogy to Example 11 from 3-(4-chloro-phenyl)-4-hydroxy-isoxazolo[5,4-c]pyridine-5-carboxylic acid ethyl ester; ESI MS (m/z): 348.20 (M+H$^+$); 346.17 (M−H$^+$).

Example 15

{[3-(2-Chloro-phenyl)-4-hydroxy-isoxazolo[5,4-c]pyridine-5-carbonyl]-amino}-acetic acid a) 3-(2-chloro-phenyl)-5-methyl-isoxazole-4-carboxylic acid ethyl ester

Prepared in analogy to Example 1 from 3-(2-chloro-phenyl)-5-methyl-isoxazole-4-carboxylic acid; ESI MS (m/z): 266.27 (M+H$^+$).

b) 5-Bromomethyl-3-(2-chloro-phenyl)-isoxazole-4-carboxylic acid ethyl ester Prepared in analogy to Example 1 from 3-(2-chloro-phenyl)-5-methyl-isoxazole-4-carboxylic acid ethyl ester; ESI MS (m/z): 344.17, 346.17 (M+H$^+$, $^{79}$Br/$^{81}$Br).

c) N-(2,4-Dimethoxy-benzyl)-N-(ethyl ethanylat-2-yl)-5-aminomethyl-3-(2-chloro-phenyl)-isoxazole-4-carboxylic acid ethyl ester Prepared in analogy to that of Example 1 from 5-bromomethyl-3-(2-chloro-phenyl)-isoxazole-4-carboxylic acid ethyl ester; ESI MS (m/z): 517.29 (M+H$^+$).

d) 3-(2-Chloro-phenyl)-4-hydroxy-isoxazolo[5,4-c]pyridine-5-carboxylic acid ethyl ester Prepared in analogy to Example 1 from N-(2,4-Dimethoxy-benzyl)-N-(ethyl ethanylat-2-yl)-5-aminomethyl-3-(2-chloro-phenyl)-isoxazole-4-carboxylic acid ethyl ester; ESI MS (m/z): 319.27 (M+H$^+$).

e) {[3-(2-Chloro-phenyl)-4-hydroxy-isoxazolo[5,4-c]pyridine-5-carbonyl]-amino}-acetic acid Prepared in analogy to Example 1 from 3-(2-chloro-phenyl)-4-hydroxy-isoxazolo[5,4-c]pyridine-5-carboxylic acid ethyl ester; ESI MS (m/z): 348.21 (M+H$^+$); 346.19 (M+H$^+$).

Example 16

{[4-Hydroxy-3-(4-methoxy-phenyl)-isoxazolo[5,4-c]pyridine-5-carbonyl]-amino}-acetic acid a) 3-(4-Methoxy-phenyl)-5-methyl-isoxazole-4-carboxylic acid ethyl ester

Prepared in analogy to Example 1 from 3-(4-methoxy-phenyl)-5-methyl-isoxazole-4-carboxylic acid; ESI MS (m/z): 262.36 (M+H$^+$).

b) 5-Bromomethyl-3-(4-methoxy-phenyl)-isoxazole-4-carboxylic acid ethyl ester Prepared in analogy to Example 1 from 3-(4-methoxy-phenyl)-5-methyl-isoxazole-4-carboxylic acid ethyl ester; ESI MS (m/z): 340.22, 342.22 (M+H$^+$, $^{79}$Br/$^{81}$Br).

c) N-(2,4-Dimethoxy-benzyl)-N-(ethyl ethanylat-2-yl)-5-aminomethyl-3-(4-methoxy-phenyl)-isoxazole-4-carboxylic acid ethyl ester Prepared in analogy to Example 1 from 5-bromomethyl-3-(4-methoxy-phenyl)-isoxazole-4-carboxylic acid ethyl ester; ESI MS (m/z): 513.36 (M+H$^+$).

d) 3-(4-methoxy-phenyl)-4-hydroxy-isoxazolo[5,4-c]pyridine-5-carboxylic acid ethyl ester Prepared in analogy to Example 1 from N-(2,4-dimethoxy-benzyl)-N-(ethyl ethanylat-2-yl)-5-aminomethyl-3-(4-methoxy-phenyl)-isoxazole-4-carboxylic acid ethyl ester; ESI MS (m/z): 315.32 (M+H$^+$).

e) {[4-Hydroxy-3-(4-methoxy-phenyl)-isoxazolo[5,4-c]pyridine-5-carbonyl]-amino}-acetic acid Prepared in analogy to Example 1 from 3-(4-methoxy-phenyl)-4-hydroxy-isoxazolo[5,4-c]pyridine-5-carboxylic acid ethyl ester; ESI MS (m/z): 344.32 (M+H$^+$); 342.28 (M−H$^+$).

Example 17

{[3-(3-Chloro-phenyl)-4-hydroxy-isoxazolo[5,4-c]pyridine-5-carbonyl]-amino}-acetic acid a) 3-(3-Chloro-phenyl)-5-methyl-isoxazole-4-carboxylic acid ethyl ester

Prepared in analogy to Example 4 from 3-chloro-N-hydroxy-benzimidoyl chloride; ESI MS (m/z): 266 (M+H$^+$).

b) 5-Bromomethyl-3-(3-chloro-phenyl)-isoxazole-4-carboxylic acid ethyl ester Prepared in analogy to Example 11 from 3-(3-Chloro-phenyl)-5-methyl-isoxazole-4-carboxylic acid ethyl ester; ESI MS (m/z): 344.17, 346.17 (M+H$^+$, $^{79}$Br/$^{81}$Br).

c) N-(2,4-Dimethoxy-benzyl)-N-(ethyl ethanylat-2-yl)-5-aminomethyl-3-(3-chloro-phenyl)-isoxazole-4-carboxylic acid ethyl ester Prepared in analogy to Example 11 from 5-Bromomethyl-3-(3-chloro-phenyl)-isoxazole-4-carboxylic acid ethyl ester; ESI MS (m/z): 517.35 (M+H$^+$).

d) 3-(3-Chloro-phenyl)-4-hydroxy-isoxazolo[5,4-c]pyridine-5-carboxylic acid ethyl ester Prepared in analogy to Example 11 from N-(2,4-Dimethoxy-benzyl)-N-(ethyl ethanylat-2-yl)-5-aminomethyl-3-(3-chloro-phenyl)-isoxazole-4-carboxylic acid ethyl ester; ESI MS (m/z): 319.27 (M+H$^+$).

e) {[3-(3-Chloro-phenyl)-4-hydroxy-isoxazolo[5,4-c]pyridine-5-carbonyl]-amino}-acetic acid Prepared in analogy to Example 11 from 3-(3-chloro-phenyl)-4-hydroxy-isoxazolo[5,4-c]pyridine-5-carboxylic acid ethyl ester; ESI MS (m/z): 348.27 (M+H$^+$); 346.23 (M−H$^{3O}$).

Example 18

{[3-(2-Chloro-6-fluoro-phenyl)-4-hydroxy-isoxazolo[5,4-c]pyridine-5-carbonyl]-amino}-acetic acid a) 3-(2-Chloro-6-fluoro-phenyl)-5-methyl-isoxazole-4-carboxylic acid ethyl ester Prepared in analogy to Example 1 from 3-(2-chloro-6-fluoro-phenyl)-5-methyl-isoxazole-4-carboxylic acid; ESI MS (m/z): 284 (M+H$^+$).

b) 5-Bromomethyl-3-(2-chloro-6-fluoro-phenyl)-isoxazole-4-carboxylic acid ethyl ester Prepared in analogy to Example 1 from 3-(2-chloro-6-fluoro-phenyl)-5-methyl-isoxazole-4-carboxylic acid ethyl ester; ESI MS (m/z): 362, 364 (M+H$^+$, $^{79}$Br/$^{81}$Br).

c) N-(2,4-Dimethoxy-benzyl)-N-(ethyl ethanylat-2-yl)-5-aminomethyl-3-(2-chloro-6-fluoro-phenyl)-isoxazole-4-carboxylic acid ethyl ester Prepared in analogy to Example 1 from 5-bromomethyl-3-(2-chloro-6-fluoro-phenyl)-isoxazole-4-carboxylic acid ethyl ester; ESI MS (m/z): 535 (M+H$^+$).

d) 3-(2-Chloro-6-fluoro-phenyl)-4-hydroxy-isoxazolo[5,4-c]pyridine-5-carboxylic acid ethyl ester Prepared in analogy to Example 1 from N-(2,4-dimethoxy-benzyl)-N-(ethyl ethanylat-2-yl)-5-aminomethyl-3-(2-chloro-6-fluoro-phenyl)-isoxazole-4-carboxylic acid ethyl ester; ESI MS (m/z): 337.18 (M+H$^+$).

e) {[3-(2-Chloro-6-fluoro-phenyl)-4-hydroxy-isoxazolo[5,4-c]pyridine-5-carbonyl]-amino}-acetic acid Prepared in analogy to Example 1 from 3-(2-chloro-6-fluoro-phenyl)-4-hydroxy-isoxazolo[5,4-c]pyridine-5-carboxylic acid ethyl ester; ESI MS (m/z): 366.18 (M+H$^+$); 364.14 (M−H$^+$).

Example 19

{[3-(4-Fluoro-phenyl)-4-hydroxy-isoxazolo[5,4-c]pyridine-5-carbonyl]-amino}-acetic acid a) 3-(4-Fluoro-phenyl)-5-methyl-isoxazole-4-carboxylic acid ethyl ester

Prepared in analogy to Example 14 from 4-fluoro-N-hydroxy-benzimidoyl chloride; ESI MS (m/z): 250.31 (M+H$^+$).

b) 5-Bromomethyl-3-(4-fluoro-phenyl)-isoxazole-4-carboxylic acid ethyl ester Prepared in analogy to Example 11 from 3-(4-fluoro-phenyl)-5-methyl-isoxazole-4-carboxylic acid ethyl ester; ESI MS (m/z): 328.17, 330.17 (M+H$^+$, $^{79}$Br/$^{81}$Br).

c) N-(2,4-Dimethoxy-benzyl)-N-(ethyl ethanylat-2-yl)-5-aminomethyl-3-(4-fluoro-phenyl)-isoxazole-4-carboxylic acid ethyl ester Prepared in analogy to Example 11 from 5-bromomethyl-3-(4-fluoro-phenyl)-isoxazole-4-carboxylic acid ethyl ester; ESI MS (m/z): 501.36 (M+H$^+$).

d) 3-(4-Fluoro-phenyl)-4-hydroxy-isoxazolo[5,4-c]pyridine-5-carboxylic acid ethyl ester Prepared in analogy to Example 11 from N-(2,4-Dimethoxy-benzyl)-N-(ethyl ethanylat-2-yl)-5-aminomethyl-3-(4-fluoro-phenyl)-isoxazole-4-carboxylic acid ethyl ester; ESI MS (m/z): 303.28 (M+H$^+$).

e) {[3-(4-Fluoro-phenyl)-4-hydroxy-isoxazolo[5,4-c]pyridine-5-carbonyl]-amino}-acetic acid Prepared in analogy to Example 11 from 3-(4-fluoro-phenyl)-4-hydroxy-isoxazolo[5,4-c]pyridine-5-carboxylic acid ethyl ester; ESI MS (m/z): 332.21 (M+H$^+$); 330.24 (M+H$^+$).

Example 20

[(7-Cyano-4-hydroxy-3-phenyl-isoxazolo[5,4-c]pyridine-5-carbonyl)-amino]-acetic acid a) 7-Cyano-4-hydroxy-3-phenyl-isoxazolo[5,4-c]pyridine-5-carboxylic acid ethyl ester A mixture of 7-bromo-4-hydroxy-3-phenyl-isoxazolo[5,4-c]pyridine-5-carboxylic acid ethyl ester (57.3 mg, 0.16 mmol), tris(dibenzylideneacetone)dipalladium(0) (29 mg, 0.03 mmol), 1,1'-bis(diphenylphosphino)ferrocene (35 mg, 0.06 mmol), zinc cyanide (10 mg, 0.09 mmol), zinc (1 mg, 0.02 mmol), and dimethylacetamide (0.32 ml) was stirred at 120° C. for two hours before it was cooled to room temperature, quenched with water, and filtered. The filtrate was partitioned between ethyl acetate and water. The organic layer was washed with brine, dried over anhydrous sodium sulfate and concentrated in vacuo. The residue was purified by flash column chromatography on silica gel with a gradient of ethyl acetate and dichloromethane to give the title compound as a brown solid (19 mg); MS (m/z): 310.31 (M+H$^+$); 308.31 (M−H$^+$).

b) [(7-Cyano-4-hydroxy-3-phenyl-isoxazolo[5,4-c]pyridine-5-carbonyl)-amino]-acetic acid Prepared in analogy to Example 11 from 7-cyano-4-hydroxy-3-phenyl-isoxazolo[5,4-c]pyridine-5-carboxylic acid ethyl ester; ESI MS (m/z): 339.29 (M+H$^+$); 337.25 (M−H$^+$).

Example 21

{[3-(4-Chloro-phenyl)-4-hydroxy-7-methyl-isoxazolo[5,4-c]pyridine-5-carbonyl]-amino}-acetic acid a) 7-Bromo-3-(4-chloro-phenyl)-4-hydroxy-isoxazolo[5,4-c]pyridine-5-carboxylic acid ethyl ester Prepared in analogy to Example 12 from 3-(4-chloro-phenyl)-4-hydroxy-isoxazolo[5,4-c]pyridine-5-carboxylic acid ethyl ester; ESI MS (m/z): 395.12, 397.09 (M+H$^+$, $^{79}$Br/$^{81}$Br).

b) 3-(4-Chloro-phenyl)-4-hydroxy-7-methyl-isoxazolo[5,4-c]pyridine-5-carboxylic acid ethyl ester Prepared in analogy to Example 12 from 7-bromo-3-(4-chloro-phenyl)-4-hydroxy-isoxazolo[5,4-c]pyridine-5-carboxylic acid ethyl ester; ESI MS (m/z): 333.29 (M+H$^+$); 331.26 (M−H$^+$).

c) {[3-(4-Chloro-phenyl)-4-hydroxy-7-methyl-isoxazolo[5,4-c]pyridine-5-carbonyl]-amino}-acetic acid Prepared in analogy to Example 12 from 3-(4-chloro-phenyl)-4-hydroxy-7-methyl-isoxazolo[5,4-c]pyridine-5-carboxylic acid ethyl ester; ESI MS (m/z): 362.29 (M+H$^+$); 360.25 (M−H$^+$).

Example 22

{[7-Bromo-3-(4-fluoro-phenyl)-4-hydroxy-isoxazolo[5,4-c]pyridine-5-carbonyl]-amino}-acetic acid a) 7-Bromo-3-(4-fluoro-phenyl)-4-hydroxy-isoxazolo[5,4-c]pyridine-5-carboxylic acid ethyl ester Prepared in analogy to Example 12 from 3-(4-fluoro-phenyl)-4-hydroxy-isoxazolo[5,4-c]pyridine-5-carboxylic acid ethyl ester; ESI MS (m/z): 381.09, 383.07 (M+H$^+$, $^{79}$Br/$^{81}$Br).

b) {[7-Bromo-3-(4-fluoro-phenyl)-4-hydroxy-isoxazolo[5,4-c]pyridine-5-carbonyl]-amino}-acetic acid Prepared in analogy to Example 11 from 7-bromo-3-(4-fluoro-phenyl)-4-hydroxy-isoxazolo[5,4-c]pyridine-5-carboxylic acid ethyl ester; ESI MS (m/z): 407.96, 409.96 (M+H$^+$, $^{79}$Br/$^{81}$Br).

Example 23

{[7-Cyano-3-(4-fluoro-phenyl)-4-hydroxy-isoxazolo[5,4-c]pyridine-5-carbonyl]-amino}-acetic acid a) {[7-Cyano-3-(4-fluoro-phenyl)-4-hydroxy-isoxazolo[5,4-c]pyridine-5-carbonyl]-amino}-acetic acid Prepared in analogy to that of Example 20 from {[7-bromo-3-(4-fluoro-phenyl)-4-hydroxy-isoxazolo[5,4-c]pyridine-5-carbonyl]-amino}-acetic acid; ESI MS (m/z): 357.19 (M+H$^+$); 355.15 (M−H$^+$).

Example 24

{[7-Bromo-3-(4-chloro-phenyl)-4-hydroxy-isoxazolo[5,4-c]pyridine-5-carbonyl]-amino}-acetic acid a) 7-Bromo-3-(4-chloro-phenyl)-4-hydroxy-isoxazolo[5,4-c]pyridine-5-carboxylic acid ethyl ester Prepared in analogy to Example 12 from 3-(4-chloro-phenyl)-4-hydroxy-isoxazolo[5,4-c]pyridine-5-carboxylic acid ethyl ester; ESI MS (m/z): 395.12, 397.09 (M+H$^+$, $^{79}$Br/$^{81}$Br).

b) {[7-Bromo-3-(4-chloro-phenyl)-4-hydroxy-isoxazolo[5,4-c]pyridine-5-carbonyl]-amino}-acetic acid Prepared in analogy to Example 11 from 7-bromo-3-(4-chloro-phenyl)-4-hydroxy-isoxazolo[5,4-c]pyridine-5-carboxylic acid ethyl ester; ESI MS (m/z): 426.09 (M+H$^+$).

Example 25

{[3-(4-Chloro-phenyl)-7-cyano-4-hydroxy-isoxazolo[5,4-c]pyridine-5-carbonyl]-amino}-acetic acid a) {[3-(4-Chloro-phenyl)-7-cyano-4-hydroxy-isoxazolo[5,4-c]pyridine-5-carbonyl]-amino}-acetic acid Prepared in analogy to Example 20 from {[7-bromo-3-(4-chloro-phenyl)-4-hydroxy-isoxazolo[5,4-c]pyridine-5-carbonyl]-amino}-acetic acid; ESI MS (m/z): 371.15 (M−H$^+$).

Example 26

{[3-(4-Fluoro-phenyl)-4-hydroxy-7-methyl-isoxazolo[5,4-c]pyridine-5-carbonyl]-amino}-acetic acid a) 7-Bromo-3-(4-fluoro-phenyl)-4-hydroxy-isoxazolo[5,4-c]pyridine-5-carboxylic acid ethyl ester Prepared in analogy to Example 12 from 3-(4-fluoro-phenyl)-4-hydroxy-isoxazolo[5,4-c]pyridine-5-carboxylic acid ethyl ester; ESI MS (m/z): 381.09, 383.07 (M+H$^+$, $^{79}$Br/$^{81}$Br).

b) 3-(4-Fluoro-phenyl)-4-hydroxy-7-methyl-isoxazolo[5,4-c]pyridine-5-carboxylic acid ethyl ester Prepared in analogy to Example 12 from 7-bromo-3-(4-fluoro-phenyl)-4-hydroxy-isoxazolo[5,4-c]pyridine-5-carboxylic acid ethyl ester; ESI MS (m/z): 317.30 (M+H$^+$); 315.26 (M−H$^+$).

c) {[3-(4-Fluoro-phenyl)-4-hydroxy-7-methyl-isoxazolo[5,4-c]pyridine-5-carbonyl]-amino}-acetic acid Prepared in analogy to Example 11 from 3-(4-fluoro-phenyl)-4-hydroxy-7-methyl-isoxazolo[5,4-c]pyridine-5-carboxylic acid ethyl ester; ESI MS (m/z): 346.40 (M+H$^+$); 344.37 (M–H$^+$).

Example 27

{[3-(3-Chloro-phenyl)-7-(ethanic acid-2-yl)amino-4-hydroxy-isoxazolo[5,4-c]pyridine-5-carbonyl]-amino}-acetic acid a) 3-(3-Chloro-phenyl)-4-hydroxy-7-iodo-isoxazolo[5,4-c]pyridine-5-carboxylic acid ethyl ester A mixture of 3-(3-chloro-phenyl)-4-hydroxy-isoxazolo[5,4-c]pyridine-5-carboxylic acid ethyl ester (377 mg, 1.18 mmole), bis(2,4,6-trimethylpyridine)iodine(I) hexafluorophosphate (1.22 g, 2.36 mmole), and dichloromethane (12 ml) was stirred at room temperature for 20 h before it was concentrated and purified by flash column chromatography on silica gel with a gradient of dichloromethane and hexanes to give the title compound as a white solid (440 mg); MS: (+) m/z 445.02 (M+H$^+$).

b) {[3-(3-Chloro-phenyl)-7-(ethanic acid-2-yl)amino-4-hydroxy-isoxazolo[5,4-c]pyridine-5-carbonyl]-amino}-acetic acid A mixture of 3-(3-chloro-phenyl)-4-hydroxy-7-iodo-isoxazolo[5,4-c]pyridine-5-carboxylic acid ethyl ester (102 mg, 0.23 mmole), glycine (603 mg, 8.03 mmole) and a 0.5 M solution of sodium methoxide in methanol (11.5 ml) was refluxed for 18 h before it was cooled to room temperature and concentrated in vacuo. The residue was dissolved in water (15 ml) and extracted with dichloromethane (2×30 ml). The remaining aqueous layer was acidified to pH=3 with 1N HCl. The resulting suspension was extracted with ethyl acetate. The organic layer was washed with brine, dried over anhydrous sodium sulfate and concentrated in vacuo. The residue was purified by column chromatography on a C18 column with a gradient of water, acetonitrile and formic acid to give the title compound as a white solid (54 mg); MS: (+) m/z 421.18 (M+H$^+$), (+) m/z 419.14 (M–H$^+$).

Example 28

{[3-(4-Chloro-phenyl)-7-ethynyl-4-hydroxy-isoxazolo[5,4-c]pyridine-5-carbonyl]-amino}-acetic acid a) 3-(4-Chloro-phenyl)-4-hydroxy-7-trimethylsilanylethynyl-isoxazolo[5,4-c]pyridine-5-carboxylic acid ethyl ester A mixture of 7-bromo-3-(4-chloro-phenyl)-4-hydroxy-isoxazolo[5,4-c]pyridine-5-carboxylic acid ethyl ester (150 mg, 0.38 mmol), tris(dibenzylideneacetone)dipalladium(0) (27 mg, 0.04 mmol), copper (I) iodide (14 mg, 0.08 mmol), trimethylsilylacetylene (107 μl, 0.76 mmol), diisopropylamine (321 μl, 2.27 mmol), and tetrahydrofuran (3.8 ml) was refluxed for eighteen hours before it was cooled to room temperature. The mixture was partitioned between ethyl acetate and water. The organic layer was washed with brine, dried over anhydrous sodium sulfate and concentrated in vacuo. The residue was purified by flash column chromatography on silica gel with a gradient of hexanes and dichloromethane to give the title compound as a yellow solid (55 mg); MS (m/z): 415.34 (M+H$^+$); 413.37 (M–H$^+$).

b) {[3-(4-Chloro-phenyl)-7-ethynyl-4-hydroxy-isoxazolo[5,4-c]pyridine-5-carbonyl]-amino}-acetic acid Prepared in analogy to Example 11 from 3-(4-chloro-phenyl)-4-hydroxy-7-trimethylsilanylethynyl-isoxazolo[5,4-c]pyridine-5-carboxylic acid ethyl ester; ESI MS (m/z): 372.17 (M+H$^+$); 370.13 (M–H$^+$).

Example 29

[(3-Biphenyl-4-yl-4-hydroxy-isoxazolo[5,4-c]pyridine-5-carbonyl)-amino]-acetic acid a) 3-Biphenyl-4-yl-5-bromomethyl-isoxazole-4-carboxylic acid ethyl ester Prepared in analogy to Example 11 from 3-biphenyl-4-yl-5-methyl-isoxazole-4-carboxylic acid ethyl ester; ESI MS (m/z): 386.15, 388.15 (M+H$^+$, $^{79}$Br/$^{81}$Br).

b) N-(2,4-Dimethoxy-benzyl)-N-(ethyl ethanylat-2-yl)-5-aminomethyl-3-biphenyl-4-yl-isoxazole-4-carboxylic acid ethyl ester Prepared in analogy to Example 11 from 3-biphenyl-4-yl-5-bromomethyl-isoxazole-4-carboxylic acid ethyl ester; ESI MS (m/z): 559.06 (M+H$^+$).

c) 3-Biphenyl-4-yl-4-hydroxy-isoxazolo[5,4-c]pyridine-5-carboxylic acid ethyl ester Prepared in analogy to Example 11 from N-(2,4-Dimethoxy-benzyl)-N-(ethyl ethanylat-2-yl)-5-aminomethyl-3-biphenyl-4-yl-isoxazole-4-carboxylic acid ethyl ester; ESI MS (m/z): 361.29 (M+H$^+$).

d) [(3-Biphenyl-4-yl-4-hydroxy-isoxazolo[5,4-c]pyridine-5-carbonyl)-amino]-acetic acid Prepared in analogy to Example 11 from 3-biphenyl-4-yl-4-hydroxy-isoxazolo[5,4-c]pyridine-5-carboxylic acid ethyl ester; ESI MS (m/z): 390.14 (M+H$^+$); 388.17 (M–H$^+$).

Example 30

2-[(4-Hydroxy-3-phenyl-isoxazolo[5,4-c]pyridine-5-carbonyl)-amino]-(S)-propionic acid a) 2-[(4-Hydroxy-3-phenyl-isoxazolo[5,4-c]pyridine-5-carbonyl)-amino]-(S)-propionic acid Prepared in analogy to Example 11 from 4-hydroxy-3-phenyl-isoxazolo[5,4-c]pyridine-5-carboxylic acid ethyl ester and L-alanine; ESI MS (m/z): 328.20 (M+H$^+$); 326.16 (M–H$^+$).

Example 31

2-[(4-Hydroxy-3-phenyl-isoxazolo[5,4-c]pyridine-5-carbonyl)-amino]-(R)-propionic acid a) 2-[(4-Hydroxy-3-phenyl-isoxazolo[5,4-c]pyridine-5-carbonyl)-amino]-(R)-propionic acid Prepared in analogy to Example 11 from 4-hydroxy-3-phenyl-isoxazolo[5,4-c]pyridine-5-carboxylic acid ethyl ester and D-alanine; ESI MS (m/z): 328.20 (M+H$^+$); 326.16 (M−H$^+$).

Example 32

{[4-Hydroxy-3-(3-trifluoromethoxy-phenyl)-isoxazolo[5,4-c]pyridine-5-carbonyl]-amino}-acetic acid a) 5-Bromomethyl-3-(3-trifluoromethoxy-phenyl)-isoxazole-4-carboxylic acid ethyl ester Prepared in analogy to Example 11 from 5-methyl-3-(3-trifluoromethoxy-phenyl)-isoxazole-4-carboxylic acid ethyl ester; ESI MS (m/z): 394.01, 396.01 (M+H$^+$, $^{79}$Br/$^{81}$Br).

b) N-(2,4-Dimethoxy-benzyl)-N-(ethyl ethanylat-2-yl)-5-aminomethyl-3-(3-trifluoromethoxy-phenyl)-isoxazole-4-carboxylic acid ethyl ester Prepared in analogy to Example 11 from 5-bromomethyl-3-(3-trifluoromethoxy-phenyl)-isoxazole-4-carboxylic acid ethyl ester; ESI MS (m/z): 567.35 (M+H$^+$).

c) 4-Hydroxy-3-(3-trifluoromethoxy-phenyl)-isoxazolo[5,4-c]pyridine-5-carboxylic acid ethyl ester Prepared in analogy to Example 11 from N-(2,4-dimethoxy-benzyl)-N-(ethyl ethanylat-2-yl)-5-aminomethyl-3-(3-trifluoromethoxy-phenyl)-isoxazole-4-carboxylic acid ethyl ester; ESI MS (m/z): 369.11 (M+H$^+$).

d) {[4-Hydroxy-3-(3-trifluoromethoxy-phenyl)-isoxazolo[5,4-c]pyridine-5-carbonyl]-amino}-acetic acid Prepared in analogy to Example 11 from 4-Hydroxy-3-(3-trifluoromethoxy-phenyl)-isoxazolo[5,4-c]pyridine-5-carboxylic acid ethyl ester; ESI MS (m/z): 398.11 (M+H$^+$); 396.07 (M−H$^+$).

Example 33

[(4-Hydroxy-3-phenyl-7-pyridin-3-yl-isoxazolo[5,4-c]pyridine-5-carbonyl)-amino]-acetic acid a) 4-Hydroxy-3-phenyl-7-pyridin-3-yl-isoxazolo[5,4-c]pyridine-5-carboxylic acid ethyl ester Prepared in analogy to Example 12 from 7-Bromo-4-hydroxy-3-phenyl-isoxazolo[5,4-c]pyridine-5-carboxylic acid ethyl ester and 3-(1,1,1-tributylstannyl)pyridine; ESI MS (m/z): 362.23 (M+H$^+$); 360.13 (M−H$^+$).

b) [(4-Hydroxy-3-phenyl-7-pyridin-3-yl-isoxazolo[5,4-c]pyridine-5-carbonyl)-amino]-acetic acid Prepared in analogy to Example 12 from 4-hydroxy-3-phenyl-7-pyridin-3-yl-isoxazolo[5,4-c]pyridine-5-carboxylic acid ethyl ester; ESI MS (m/z): 346.40 (M+H$^+$); 344.37 (M−H$^+$).

Example 34

{[4-Hydroxy-3-(4-trifluoromethyl-phenyl)-isoxazolo[5,4-c]pyridine-5-carbonyl]-amino}-acetic acid a) 5-Bromomethyl-3-(4-trifluoromethyl-phenyl)-isoxazole-4-carboxylic acid ethyl ester Prepared in analogy to Example 11 from 5-Methyl-3-(4-trifluoromethyl-phenyl)-isoxazole-4-carboxylic acid ethyl ester; ESI MS (m/z): 378.15, 380.15 (M+H$^+$, $^{79}$Br/$^{81}$Br).

b) N-(2,4-Dimethoxy-benzyl)-N-(ethyl ethanylat-2-yl)-5-aminomethyl-3-(4-trifluoromethyl-phenyl)-isoxazole-4-carboxylic acid ethyl ester Prepared in analogy to Example 11 from 5-bromomethyl-3-(4-trifluoromethyl-phenyl)-isoxazole-4-carboxylic acid ethyl ester; ESI MS (m/z): 551.38 (M+H$^+$).

c) 4-Hydroxy-3-(4-trifluoromethyl-phenyl)-isoxazolo[5,4-c]pyridine-5-carboxylic acid ethyl ester Prepared in analogy to Example 11 from N-(2,4-dimethoxy-benzyl)-N-(ethyl ethanylat-2-yl)-5-aminomethyl-3-(4-trifluoromethyl-phenyl)-isoxazole-4-carboxylic acid ethyl ester; ESI MS (m/z): 353.27 (M+H$^+$).

d) {[4-Hydroxy-3-(4-trifluoromethyl-phenyl)-isoxazolo[5,4-c]pyridine-5-carbonyl]-amino}-acetic acid Prepared in analogy to Example 11 from 4-Hydroxy-3-(4-trifluoromethyl-phenyl)-isoxazolo[5,4-c]pyridine-5-carboxylic acid ethyl ester; ESI MS (m/z): 380.26 (M−H$^+$).

Example 35

{[4-Hydroxy-3-(2-trifluoromethoxy-phenyl)-isoxazolo[5,4-c]pyridine-5-carbonyl]-amino}-acetic acid a) 5-Bromomethyl-3-(2-trifluoromethoxy-phenyl)-isoxazole-4-carboxylic acid ethyl ester Prepared in analogy to Example 11 from 5-methyl-3-(2-trifluoromethoxy-phenyl)-isoxazole-4-carboxylic acid ethyl ester; ESI MS (m/z): 394.17, 396.17 (M+H$^+$, $^{79}$Br/$^{81}$Br).

b) N-(2,4-Dimethoxy-benzyl)-N-(ethyl ethanylat-2-yl)-5-aminomethyl-3-(2-trifluoromethoxy-phenyl)-isoxazole-4-carboxylic acid ethyl ester Prepared in analogy to Example 11 from 5-bromomethyl-3-(2-trifluoromethoxy-phenyl)-isoxazole-4-carboxylic acid ethyl ester; ESI MS (m/z): 567.35 (M+H$^+$).

c) 4-Hydroxy-3-(2-trifluoromethoxy-phenyl)-isoxazolo[5,4-c]pyridine-5-carboxylic acid ethyl ester Prepared in analogy to Example 11 from N-(2,4-dimethoxy-benzyl)-N-(ethyl ethanylat-2-yl)-5-aminomethyl-3-(2-trifluoromethoxy-phenyl)-isoxazole-4-carboxylic acid ethyl ester; ESI MS (m/z): 369.15 (M+H⁺).

d) {[4-Hydroxy-3-(2-trifluoromethoxy-phenyl)-isoxazolo[5,4-c]pyridine-5-carbonyl]-amino}-acetic acid Prepared in analogy to Example 11 from 4-Hydroxy-3-(2-trifluoromethoxy-phenyl)-isoxazolo[5,4-c]pyridine-5-carboxylic acid ethyl ester; ESI MS (m/z): 398.21 (M+H⁺); 396.24 (M−H⁺).

Example 36

[(4-Hydroxy-3-phenyl-7-pyridin-4-yl-isoxazolo[5,4-c]pyridine-5-carbonyl)-amino]-acetic acid a) 4-Hydroxy-3-phenyl-7-pyridin-4-yl-isoxazolo[5,4-c]pyridine-5-carboxylic acid ethyl ester Prepared in analogy to Example 12 from 7-Bromo-4-hydroxy-3-phenyl-isoxazolo[5,4-c]pyridine-5-carboxylic acid ethyl ester and 4-(1,1,1-tributylstannyl)pyridine; ESI MS (m/z): 362.31 (M+H⁺); 360.34 (M−H⁺).

b) [(4-Hydroxy-3-phenyl-7-pyridin-4-yl-isoxazolo[5,4-c]pyridine-5-carbonyl)-amino]-acetic acid Prepared in analogy to that of Example 12 from 4-Hydroxy-3-phenyl-7-pyridin-4-yl-isoxazolo[5,4-c]pyridine-5-carboxylic acid ethyl ester; ESI MS (m/z): 391.27 (M+H⁺); 389.30 (M−H⁺).

Example 37

[(4-Hydroxy-3-phenyl-7-pyridin-2-yl-isoxazolo[5,4-c]pyridine-5-carbonyl)-amino]-acetic acid a) 4-Hydroxy-3-phenyl-7-pyridin-2-yl-isoxazolo[5,4-c]pyridine-5-carboxylic acid ethyl ester Prepared in analogy to that of Example 12 from 7-Bromo-4-hydroxy-3-phenyl-isoxazolo[5,4-c]pyridine-5-carboxylic acid ethyl ester and 2-(1,1,1-tributylstannyl)pyridine; ESI MS (m/z): 362.31 (M+H⁺); 360.34 (M−H⁺).

b) [(4-Hydroxy-3-phenyl-7-pyridin-2-yl-isoxazolo[5,4-c]pyridine-5-carbonyl)-amino]-acetic acid Prepared in analogy to that of Example 12 from 4-Hydroxy-3-phenyl-7-pyridin-2-yl-isoxazolo[5,4-c]pyridine-5-carboxylic acid ethyl ester; ESI MS (m/z): 391.27 (M+H⁺); 389.30 (M−H⁺).

Example 38

[(4-Hydroxy-3-phenyl-7-trifluoromethyl-isoxazolo[5,4-c]pyridine-5-carbonyl)-amino]-acetic acid a) 4-Hydroxy-7-iodo-3-phenyl-isoxazolo[5,4-c]pyridine-5-carboxylic acid ethyl ester Prepared in analogy to Example 27 from 4-hydroxy-3-phenyl-isoxazolo[5,4-c]pyridine-5-carboxylic acid ethyl ester; ESI MS (m/z): 411.13 (M+H⁺).

b) 4-Hydroxy-3-phenyl-7-trifluoromethyl-isoxazolo[5,4-c]pyridine-5-carboxylic acid ethyl ester A mixture of 4-hydroxy-7-iodo-3-phenyl-isoxazolo[5,4-c]pyridine-5-carboxylic acid ethyl ester (200 mg, 0.49 mmole), methyl fluorosulfonyldifluoroacetate (470 mg, 2.45 mmole), copper(I) iodide (280 mg, 1.47 mmole), and dimethylformamide (2.5 ml) was stirred at 70° C. for sixteen hours before it was cooled to room temperature and filtered. The filtrate was partitioned between dichloromethane and water. The organic layer was washed with water, brine, dried over anhydrous sodium sulfate and concentrated in vacuo. The residue was purified by column chromatography on silica gel with a gradient of dichloromethane and hexanes to give the title compound as a yellow solid (116 mg); ESI MS (m/z): 353.20 (M+H⁺), 351.23 (M−H⁺).

c) [(4-Hydroxy-3-phenyl-7-trifluoromethyl-isoxazolo[5,4-c]pyridine-5-carbonyl)-amino]-acetic acid Prepared in analogy to Example 11 from 4-Hydroxy-3-phenyl-7-trifluoromethyl-isoxazolo[5,4-c]pyridine-5-carboxylic acid ethyl ester; ESI MS (m/z): 382.23 (M+H⁺); 380.19 (M−H⁺).

Example 39

{[4-Hydroxy-3-(4-trifluoromethoxy-phenyl)-isoxazolo[5,4-c]pyridine-5-carbonyl]-amino}-acetic acid Prepared in analogy to Example 11 from 4-hydroxy-3-(4-trifluoromethoxy-phenyl)-isoxazolo[5,4-c]pyridine-5-carboxylic acid ethyl ester; ESI MS (m/z): 398.21 (M+H⁺); 396.24 (M−H⁺).

Example 40

{[3-(4-tert-Butyl-phenyl)-4-hydroxy-isoxazolo[5,4-c]pyridine-5-carbonyl]-amino}-acetic acid a) 5-Bromomethyl-3-(4-tert-butyl-phenyl)-isoxazole-4-carboxylic acid ethyl ester Prepared in analogy to Example 11 from 3-(4-tert-butyl-phenyl)-5-methyl-isoxazole-4-carboxylic acid ethyl ester; ESI MS (m/z): 366.26, 368.23 (M+H⁺, ⁷⁹Br/⁸¹Br).

b) N-(2,4-Dimethoxy-benzyl)-N-(ethyl ethanylat-2-yl)-5-aminomethyl-3-(4-tert-butyl-phenyl)-isoxazole-4-carboxylic acid ethyl ester Prepared in analogy to Example 11 from 5-bromomethyl-3-(4-tert-butyl-phenyl)-isoxazole-4-carboxylic acid ethyl ester; ESI MS (m/z): 539.07 (M+H⁺).

c) 4-Hydroxy-3-(4-tert-butyl-phenyl)-isoxazolo[5,4-c]pyridine-5-carboxylic acid ethyl ester Prepared in analogy to Example 11 from N-(2,4-dimethoxy-benzyl)-N-(ethyl ethanylat-2-yl)-5-aminomethyl-3-(4-tert-butyl-phenyl)-isoxazole-4-carboxylic acid ethyl ester; ESI MS (m/z): 341.37 (M+H⁺).

d) {[3-(4-tert-Butyl-phenyl)-4-hydroxy-isoxazolo[5,4-c]pyridine-5-carbonyl]-amino}-acetic acid Prepared in analogy to Example 11 from 4-hydroxy-3-(4-tert-butyl-phenyl)-isoxazolo[5,4-c]pyridine-5-carboxylic acid ethyl ester; ESI MS (m/z): 370.34 (M+H⁺); 368.30 (M−H⁺).

Example 41

[(7-Bromo-4-hydroxy-3-phenyl-isoxazolo[5,4-c]pyridine-5-carbonyl)-amino]-acetic acid Prepared in analogy to that of Example 11 from 7-bromo-4-hydroxy-3-phenyl-isoxazolo[5,4-c]pyridine-5-carboxylic acid ethyl ester; ESI MS (m/z): 392.06, 394.03 (M+H$^+$, $^{79}$Br/$^{81}$Br), 390.02, 391.99.03 (M−H$^+$, $^{79}$Br/$^{81}$Br).

Example 42

[(7-Hydroxy-3-phenyl-isoxazolo[4,5-c]pyridine-6-carbonyl)-amino]-acetic acid a) 1-Phenyl-propan-1-one oxime

Hydroxylamine hydrochloride (17.1 g, 246 mmol) and sodium acetate (20.2 g, 246 mmol) were added to 110 mL of methanol and the resulting white slurry was stirred at room temperature for 30 min. Propiophenone (30 g, 224 mmol) was added and the mixture was stirred at room temperature for 20 hours. Water (100 mL) was added and the mixture was stirred for 10 min. The product was extracted with EtOAc and the organic layer was washed with saturated NaHCO$_3$ solution and dried over MgSO$_4$. The solvent was evaporated in vacuo to give 32.4 g of the title compound. $^1$H NMR (CDCl$_3$, 200 MHz): δ=9.21 (s, 1H), 7.60-7.72 (m, 2H), 7.38-7.50 (m, 3H), 2.91 (q, 2H, J=7.8 Hz), 1.23 (t, 3H, J=7.4 Hz).

b) Ethyl 4-(hydroxyimino)-3-methyl-2-oxo-4-phenylbutanoate

Diisopropylamine (21 mL, 148 mmol) was added to 50 mL of THF and cooled with an external ice bath. Butyllithium (56 mL, 141 mmol, 2.5 M in hexanes) was added and the mixture was stirred at 0° C. for 30 min, and brought to room temperature. The resulting LDA solution was added to a mixture of 1-phenyl-propan-1-one oxime (10 g, 67 mmol) and THF (50 mL) at 0° C. Following the addition, the reaction mixture was stirred at 0° C. for 1 hour and warmed to room temperature. The mixture was then transferred to a syringe and added dropwise to a flask containing a pre-cooled mixture of diethyl oxalate (46 mL, 336 mmol) and THF (150 mL) at 0° C. After the addition was complete, the reaction mixture was stirred at room temperature for 18 hours. The mixture was cooled in an ice bath and quenched with 150 mL of 3M hydrochloric acid. The organic layer was separated and the aqueous layer was extracted with EtOAc. The aqueous layer was then neutralized with solid sodium bicarbonate and extracted further with CH$_2$Cl$_2$. The organic layers were combined, dried over MgSO$_4$ and concentrated. The crude oil was purified by chromatography (0-40% EtOAc/hexanes) to give 22 g of the title compound. MS: (+) m/z 250.48 (M+1).

c) Ethyl 4-methyl-3-phenylisoxazole-5-carboxylate

Ethyl 4-(hydroxyimino)-3-methyl-2-oxo-4-phenylbutanoate (13.2 g, 53.0 mmol) and concentrated sulfuric acid (10 mL) were added to 150 mL of absolute ethanol and the mixture was refluxed for 20 hours. After the mixture cooled to room temperature, saturated sodium bicarbonate solution was added to neutralize the mixture. The product was extracted with EtOAc and the combined organic layers were dried over MgSO$_4$ and concentrated to give 12.5 g of the title compound. MS: (+) m/z 232.46 (M+1).

d) Ethyl 4-(bromomethyl)-3-phenylisoxazole-5-carboxylate

Ethyl 4-methyl-3-phenylisoxazole-5-carboxylate (0.2 g, 0.87 mmol), NBS (0.17 g, 0.95 mmol), and benzoyl peroxide (21 mg, 0.087 mmol) were added to 5 mL of carbon tetrachloride and the mixture was refluxed for 16 h. The mixture was diluted with CH$_2$Cl$_2$, and 5 g of silica gel was added. The solvent was removed in vacuo and the crude was purified by flash chromatography (0-20% EtOAc/hexanes) to give 214 mg of the title compound. MS: (+) m/z 310.31, 312.28 (M+1, $^{79}$Br/$^{81}$Br).

e) Ethyl 4-(((2,4-dimethoxybenzyl)(2-ethoxy-2-oxo-ethyl)amino)methyl)-3-phenylisoxazole-5-carboxylate Ethyl 4-(bromomethyl)-3-phenylisoxazole-5-carboxylate (28.1 g, 90.6 mmol) was dissolved in 200 mL of DMF. N-(2,4-dimethoxybenzyl)glycine ethyl ester (22.9 g, 90.6 mmol) and potassium carbonate (9.2 g, 66.4 mmol) were added, and the mixture was stirred at room temperature for 16 h. EtOAc (200 mL) and water (100 mL) were added and the aqueous layer was extracted with additional EtOAc. The combined organic layer was washed with water and brine, and dried over MgSO$_4$. After solvent was removed in vacuo, the crude product was purified by flash chromatography (0-40% EtOAc/hexanes) to give 29.6 g of the title compound. MS: (+) m/z 483.73 (M+1).

f) Ethyl 7-hydroxy-3-phenylisoxazolo[4,5-c]pyridine-6-carboxylate

Ethyl 4-(((2,4-dimethoxybenzyl)(2-ethoxy-2-oxoethyl)amino)methyl)-3-phenylisoxazole-5-carboxylate (16.1 g, 33.4 mmol) was dissolved in 300 mL of THF and cooled to −78° C. Potassium tert-butoxide solution (66.7 mL, 66.7 mmol, 1M in THF) was added dropwise, and the mixture was stirred for 14 hours, the cold bath allowed to evaporate spontaneously. The reaction mixture was quenched with 60 mL of 1M HCl and 500 mL of saturated ammonium chloride solution. The product was extracted with EtOAc and the organic layer was dried over MgSO$_4$ and concentrated to give 13.7 g of crude oil.

The crude intermediate was dissolved in 200 mL of CH$_2$Cl$_2$. Thionyl chloride (3.4 mL, 47.1 mmol) was added and within minutes a precipitate began to form. The reaction mixture was stirred for another hour and the mixture was filtered through a medium porosity funnel. The solid was rinsed twice with cold CH$_2$Cl$_2$ and dried under vacuum to give 7.9 g of the title compound. MS: (+) m/z 285.42 (M+1).

g) [(7-Hydroxy-3-phenyl-isoxazolo[4,5-c]pyridine-6-carbonyl)-amino]-acetic acid Ethyl 7-hydroxy-3-phenylisoxazolo[4,5-c]pyridine-6-carboxylate (0.11 g, 0.39 mmol) was dissolved in 10 mL of DMF. Glycine (0.58 g, 7.75 mmol) and sodium ethoxide (0.40 g, 5.81 mmol) were added and the mixture was refluxed for 14 h. The mixture was cooled to room temperature and diluted with 60 mL of water. Concentrated hydrochloric acid was added dropwise until pH was 3. The resulting suspension was filtered and the solid was dried under vacuum to give 70 mg of the title compound. MS: (+) m/z 314.00 (M+1).

Example 43

(S)-2-[(7-Hydroxy-3-phenyl-isoxazolo[4,5-c]pyridine-6-carbonyl)amino]-propionic acid Ethyl 7-hydroxy-3-phenylisoxazolo[4,5-c]pyridine-6-carboxylate (0.1 g, 0.35 mmol) was dissolved in 10 mL of DMF. L-Alanine (0.627 g, 7.04 mmol) and sodium ethoxide (0.36 g, 5.28 mmol) were added and the mixture was refluxed for 3 h. The mixture was cooled to room temperature and diluted with 70 mL of water. Concentrated hydrochloric acid was added dropwise until pH was 2. The resulting suspension was filtered and the solid dried under vacuum to give 91 mg of the title compound. MS: (+) m/z 328.00 (M+1).

Example 44

(R)-2-[(7-Hydroxy-3-phenyl-isoxazolo[4,5-c]pyridine-6-carbonyl)-amino]-propionic acid Ethyl 7-hydroxy-3-phenylisoxazolo[4,5-c]pyridine-6-carboxylate (0.1 g, 0.35 mmol) was dissolved in 10 mL of DMF. L-Alanine (0.627 g, 7.04 mmol) and sodium ethoxide (0.36 g, 5.28 mmol) were added and the mixture was refluxed for 3 h. The mixture was cooled to room temperature and diluted with 70 mL of water. Concentrated hydrochloric acid was added dropwise until pH was 2. The resulting suspension was filtered and the solid dried under vacuum to give 55 mg of the title compound. MS: (+) m/z 328.00 (M+1).

Example 45

{[3-(4-Fluoro-phenyl)-7-hydroxy-isoxazolo[4,5-c]pyridine-6-carbonyl]-amino}-acetic acid a) 1-(4-Fluoro-phenyl)-propan-1-one oxime Hydroxylamine hydrochloride (7.5 g, 108 mmol) and sodium acetate (8.9 g, 108 mmol) were added to 50 mL of methanol and the resulting white slurry was stirred at room temperature for 30 min. 1-(4-Fluorophenyl)propan-1-one (15 g, 98.6 mmol) was added and the mixture was stirred at room temperature for 20 hours. Water (50 mL) was added and the mixture was stirred for 10 min. The product was extracted with EtOAc and the organic layer was washed with saturated NaHCO$_3$ solution and dried over MgSO$_4$. The solvent was evaporated in vacuo to give 16.4 g of the title compound. MS: (+) m/z 168.36 (M+1).

b) Ethyl 4-(4-fluorophenyl)-4-(hydroxyimino)-3-methyl-2-oxobutanoate

Diisopropylamine (18.2 mL, 129 mmol) was added to 60 mL of THF and cooled with an external ice bath. Butyllithium (50 mL, 126 mmol, 2.5 M in hexanes) was added and the mixture was stirred at 0° C. for 30 min, and brought to room temperature. The resulting LDA solution was added to a mixture of 1-(4-fluorophenyl)propan-1-one oxime (10 g, 59.9 mmol) and THF (50 mL) at 0° C. Following the addition, the reaction mixture was stirred at 0° C. for 1 hour and warmed to room temperature. The mixture was then transferred to a syringe and added dropwise to a flask containing a pre-cooled mixture of diethyl oxalate (41 mL, 299 mmol) and THF (150 mL) at 0° C. After the addition was complete, the reaction mixture was stirred at room temperature for 18 hours. The mixture was cooled in an ice bath and quenched with 200 mL of 10% hydrochloric acid. The organic layer was separated and the aqueous layer was extracted with EtOAc. The aqueous layer was then neutralized with solid sodium bicarbonate and extracted further with CH$_2$Cl$_2$. The organic layers were combined, dried over MgSO$_4$ and concentrated. The crude oil was purified by chromatography (0-35% EtOAc/hexanes) to give 10.1 g of the title compound. MS: (+) m/z 268.36 (M+1).

c) Ethyl 3-(4-fluorophenyl)-4-methylisoxazole-5-carboxylate

Ethyl 4-(4-fluorophenyl)-4-(hydroxyimino)-3-methyl-2-oxobutanoate (10.1 g, 37.8 mmol) and concentrated sulfuric acid (10 mL) were added to 150 mL of absolute ethanol and the mixture was refluxed for 20 hours. After the mixture cooled to room temperature, saturated sodium bicarbonate solution was added to neutralize the mixture. The product was extracted with EtOAc and the combined organic layer was dried over MgSO$_4$ and concentrated to give 8.6 g of the title compound. MS: (+) m/z 250.41 (M+1).

d) Ethyl 4-(bromomethyl)-3-(4-fluorophenyl)isoxazole-5-carboxylate

Ethyl 3-(4-fluorophenyl)-4-methylisoxazole-5-carboxylate (8.6 g, 34.5 mmol), NBS (6.8 g, 38.0 mmol), and benzoyl peroxide (0.84 g, 3.45 mmol) were added to 200 mL of carbon tetrachloride and the mixture was refluxed for 16 h. The reaction mixture was filtered and the filtrate was removed in vacuo to give 12.4 g of the title compound. $^1$H NMR (CDCl$_3$, 200 MHz): δ=9.21 (s, 1H), 7.75-7.85 (m, 2H), 7.22-7.32 (m, 2H), 4.66 (s, 2H), 4.54 (q, 2H, J=7.0 Hz), 1.41 (t, 3H, J=7.0 Hz).

e) Ethyl 4-(((2,4-dimethoxybenzyl)(2-ethoxy-2-oxoethyl)amino)methyl)-3-(4-fluorophenyl)isoxazole-5-carboxylate Ethyl 4-(bromomethyl)-3-(4-fluorophenyl)isoxazole-5-carboxylate (12.4 g, 37.8 mmol) was dissolved in 80 mL of DMF. N-(2,4-dimethoxybenzyl)glycine ethyl ester (9.56 g, 37.8 mmol) and potassium carbonate (5.75 g, 41.6 mmol) were added, and the mixture was stirred at room temperature for 16 h. EtOAc (200 mL) and brine (200 mL) were added and the aqueous layer was extracted with additional EtOAc. The combined organic layer was washed with water and brine, and dried over MgSO$_4$. After solvent was removed in vacuo, the crude product was purified by flash chromatography (0-40% EtOAc/hexanes) to give 8.7 g of the title compound. $^1$H NMR (CDCl$_3$, 200 MHz): δ=8.00-8.13 (m, 2H), 7.01-7.18 (m, 3H), 6.38-6.45 (m, 2H), 4.48 (q, 2H, J=7.4 Hz), 4.00-4.20 (m, 4H), 3.82 (s, 5H), 3.65 (s, 3H), 3.30 (s, 2H), 1.47 (t, 3H, J=7.0 Hz), 1.20-1.30 (m, 3H).

f) Ethyl 3-(4-fluorophenyl)-7-hydroxyisoxazolo[4,5-c]pyridine-6-carboxylate

Ethyl 4-(((2,4-dimethoxybenzyl)(2-ethoxy-2-oxoethyl)amino)methyl)-3-(4-fluorophenyl)isoxazole-5-carboxylate (8.7 g, 17.4 mmol) was dissolved in 150 mL of THF and cooled to -78° C. Potassium tert-butoxide solution (34.8 mL, 34.8 mmol, 1M in THF) was added dropwise, and the mixture was stirred for 14 hours, the cold bath allowed to evaporate spontaneously. The reaction mixture was quenched with 30 mL of 1M HCl and 200 mL of saturated ammonium chloride solution. The product was extracted with EtOAc and the organic layer was dried over MgSO$_4$ and concentrated to give 7.54 g of crude oil. The crude intermediate was dissolved in 100 mL of CH$_2$Cl$_2$. Thionyl chloride (1.8 mL, 24.9 mmol) was added and within minutes a precipitate began to form. The reaction mixture was stirred for another hour and the mixture was filtered through a medium porosity funnel. The solid was rinsed twice with cold CH$_2$Cl$_2$ and dried under vacuum to give 3.63 g of the title compound. MS: (+) m/z 303.37 (M+1).

g) {[3-(4-Fluoro-phenyl)-7-hydroxy-isoxazolo[4,5-c]pyridine-6-carbonyl]-amino}-acetic acid Ethyl 3-(4-fluorophenyl)-7-hydroxyisoxazolo[4,5-c]pyridine-6-carboxylate (0.11 g, 0.36 mmol) was dissolved in 10 mL of DMF. Glycine (0.55 g, 7.28 mmol) and sodium ethoxide (0.37 g, 5.46 mmol) were added and the mixture was refluxed for 14 h. The mixture was cooled to room temperature and diluted with 60 mL of water. Concentrated hydrochloric acid was added dropwise until pH was 3. The resulting suspension was filtered and the solid was dried under vacuum to give 69 mg of the title compound. MS: (+) m/z 332.00 (M+1).

Example 46

{[7-Hydroxy-3-(4-methoxy-phenyl)-isoxazolo[4,5-c]pyridine-6-carbonyl]-amino}-acetic acid a) 1-(4-Methoxyphenyl)propan-1-one oxime

Hydroxylamine hydrochloride (7.0 g, 100 mmol) and sodium acetate (8.2 g, 100 mmol) were added to 50 mL of methanol and the resulting white slurry was stirred at room temperature for 30 min. 1-(4-Methoxyphenyl)propan-1-one (15 g, 91.4 mmol) was added and the mixture was stirred at room temperature for 20 hours, and then refluxed for 20 hours. Water (50 mL) was added and the mixture was stirred for 10 min. The product was extracted with EtOAc and the organic layer was washed with saturated NaHCO$_3$ solution and dried over MgSO$_4$. The solvent was evaporated in vacuo to give 18.3 g of the title compound. MS: (+) m/z 180.39 (M+1).

b) Ethyl 4-(hydroxyimino)-4-(4-methoxyphenyl)-3-methyl-2-oxobutanoate

Diisopropylamine (22 mL, 154 mmol) was added to 60 mL of THF and cooled with an external ice bath. Butyllithium (59 mL, 147 mmol, 2.5 M in hexanes) was added and the mixture was stirred at 0° C. for 30 min, and brought to room temperature. The resulting LDA solution was added to a mixture of 1-(4-methoxyphenyl)propan-1-one oxime (12 g, 67.0 mmol) and THF (60 mL) at 0° C. Following the addition, the reaction mixture was stirred at 0° C. for 1 hour and warmed to room temperature. The mixture was then transferred to a syringe and added dropwise to a flask containing a pre-cooled mixture of diethyl oxalate (46 mL, 335 mmol) and THF (150 mL) at 0° C. After the addition was complete, the reaction mixture was stirred at room temperature for 18 hours. The mixture was cooled in an ice bath and quenched with 200 mL of 10% hydrochloric acid. The organic layer was separated and the aqueous layer was extracted with EtOAc. The aqueous layer was then neutralized with solid sodium bicarbonate and extracted further with CH$_2$Cl$_2$. The organic layers were combined, dried over MgSO$_4$ and concentrated. The crude oil was purified by chromatography (0-40% EtOAc/hexanes) to give 17.7 g of the title compound. MS: (+) m/z 280 (M+1).

c) Ethyl 3-(4-methoxyphenyl)-4-methylisoxazole-5-carboxylate

Ethyl 4-(hydroxyimino)-4-(4-methoxyphenyl)-3-methyl-2-oxobutanoate (17.7 g, 63.4 mmol) and concentrated sulfuric acid (15 mL) were added to 180 mL of absolute ethanol and the mixture was refluxed for 20 hours. After the mixture cooled to room temperature, saturated sodium bicarbonate solution was added to neutralize the mixture. The product was extracted with EtOAc and the combined organic layer was dried over MgSO$_4$ and concentrated to give 12.4 g of the title compound. MS: (+) m/z 262.45 (M+1).

d) Ethyl 4-(bromomethyl)-3-(4-methoxyphenyl)isoxazole-5-carboxylate

Ethyl 3-(4-methoxyphenyl)-4-methylisoxazole-5-carboxylate (12.4 g, 47.5 mmol), NBS (10.1 g, 57.0 mmol), and benzoyl peroxide (1.15 g, 4.75 mmol) were added to 250 mL of carbon tetrachloride and the mixture was refluxed for 16 h. The reaction mixture was filtered and the filtrate was removed in vacuo to give a brown solid, which was used in the next reaction without purification. MS: (+) m/z 340.35, 342.33 (M+1, $^{79}$Br/$^{81}$Br).

e) Ethyl 4-(((2,4-dimethoxybenzyl)(2-ethoxy-2-oxoethyl)amino)methyl)-3-(4-methoxyphenyl)isoxazole-5-carboxylate Ethyl 4-(bromomethyl)-3-(4-methoxyphenyl)isoxazole-5-carboxylate (47.5 mmol) was dissolved in 100 mL of DMF. N-(2,4-dimethoxybenzyl)glycine ethyl ester (12.0 g, 47.5 mmol) and potassium carbonate (7.2 g, 41.6 mmol) were added, and the mixture was stirred at room temperature for 16 h. EtOAc (200 mL) and brine (200 mL) were added and the aqueous layer was extracted with additional EtOAc. The combined organic layer was washed with water and brine, and dried over MgSO$_4$. After solvent was removed in vacuo, the crude was purified by flash chromatography (0-35% EtOAc/hexanes) to give 13.7 g of the title compound. $^1$H NMR (CDCl$_3$, 200 MHz): δ=8.00 (d, 2H, J=8.8 Hz), 7.06-7.15 (m, 1H), 6.93 (d, 2H, J=8.8 Hz), 6.30-6.50 (m, 2H), 4.47 (q, 2H, J=7.4 Hz), 4.10-4.22 (m, 2H), 3.70-3.90 (m, 9H), 3.66 (s, 4H), 3.31 (s, 2H), 1.43 (t, 3H, J=7.0 Hz), 1.20-1.40 (m, 3H).

f) Ethyl 7-hydroxy-3-(4-methoxyphenyl)isoxazolo[4,5-c]pyridine-6-carboxylate Ethyl 4-(((2,4-dimethoxybenzyl)(2-ethoxy-2-oxoethyl)amino)methyl)-3-(4-methoxyphenyl)isoxazole-5-carboxylate (13.7 g, 26.7 mmol) was dissolved in 230 mL of THF and cooled to −78° C. Potassium tert-butoxide solution (53.5 mL, 53.5 mmol, 1M in THF) was added dropwise, and the mixture was stirred for 14 hours, the cold bath allowed to evaporate spontaneously. The reaction mixture was quenched with 50 mL of 1M HCl and 300 mL of saturated ammonium chloride solution. The product was extracted with EtOAc and the organic layer was dried over MgSO$_4$ and concentrated to give 11.4 g of crude oil. The crude intermediate was dissolved in 150 mL of CH$_2$Cl$_2$. Thionyl chloride (2.7 mL, 36.7 mmol) was added and the reaction mixture was stirred for 16 h. The mixture was filtered through a medium porosity funnel. The solid was rinsed twice with cold CH$_2$Cl$_2$ and dried under vacuum to give 3.51 g of the title compound. MS: (+) m/z 315.40 (M+1).

g) {[7-Hydroxy-3-(4-methoxy-phenyl)-isoxazolo[4,5-c]pyridine-6-carbonyl]-amino}-acetic acid Ethyl 7-hydroxy-3-(4-methoxyphenyl)isoxazolo[4,5-c]pyridine-6-carboxylate (0.12 g, 0.38 mmol) was dissolved in 10 mL of DMF. Glycine (0.574 g, 7.64 mmol) and sodium ethoxide (0.391 g, 5.73 mmol) were added and the mixture was refluxed for 2 h. The mixture was cooled to room temperature and diluted with 70 mL of water. Concentrated hydrochloric acid was added dropwise until pH was 3. The resulting suspension was filtered and the solid was dried under vacuum to give 94 mg of the title compound. MS: (+) m/z 344.37 (M+1).

Example 47

[(7-Hydroxy-3-thiophen-2-yl-isoxazolo[4,5-c]pyridine-6-carbonyl)-amino]-acetic acid a) 1-(Thiophen-2-yl)propan-1-one oxime Hydroxylamine hydrochloride (3.2 g, 46.3 mmol) and sodium acetate (3.8 g, 46.3 mmol) were added to 20 mL of methanol and the resulting white slurry was stirred at room temperature for 30 min. 1-(Thiophen-2-yl)propan-1-one (5.9 g, 42.1 mmol) was added and the mixture was stirred at room temperature for 20 hours. Water (20 mL) was added and the product was extracted with EtOAc and the organic layer was washed with saturated NaHCO$_3$ solution and dried over MgSO$_4$. The solvent was evaporated in vacuo to give 6.3 g of the title compound. MS: (+) m/z 156.32 (M+1).

b) Ethyl 4-(hydroxyimino)-3-methyl-2-oxo-4-(thiophen-2-yl)butanoate 1-(Thiophen-2-yl)propan-1-one oxime (6.3 g, 40.6 mmol) was dissolved in 100 mL of THF and cooled to 0° C. LDA solution (46.7 mL, 93.5 mmol, 2M in heptane/THF/ethyl benzene) was added dropwise, and the reaction mixture was stirred at 0° C. for 1 hour and then warmed to room temperature. The mixture was then transferred to an addition funnel and added dropwise to a flask containing a pre-cooled mixture of diethyl oxalate (27.6 mL, 203 mmol) and THF (100 mL) at 0° C. After the addition was complete, the reaction mixture was stirred at room temperature for 18 hours. The mixture was cooled in an ice bath and quenched with 150 mL of 10% hydrochloric acid. The organic layer was separated and the aqueous layer was extracted with EtOAc. The aqueous layer was then neutralized with solid sodium bicarbonate and extracted further with CH$_2$Cl$_2$. The organic layers were combined, dried over MgSO$_4$ and concentrated. The crude oil was purified by chromatography (0-20% EtOAc/hexanes) to give 7.7 g of the title compound. MS: (+) m/z 256.33 (M+1).

c) Ethyl 4-methyl-3-(thiophen-2-yl)isoxazole-5-carboxylate

Ethyl 4-(hydroxyimino)-3-methyl-2-oxo-4-(thiophen-2-yl)butanoate (7.7 g, 30.2 mmol) and concentrated sulfuric acid (8 mL) were added to 120 mL of absolute ethanol and the mixture was refluxed for 20 hours. After the mixture cooled to room temperature, saturated sodium bicarbonate solution was added to neutralize the mixture. The product was extracted with EtOAc and the combined organic layer was dried over MgSO$_4$ and concentrated to give 3.9 g of the title compound. MS: (+) m/z 238.38 (M+1).

d) Ethyl 4-(bromomethyl)-3-(thiophen-2-yl)isoxazole-5-carboxylate

Ethyl 4-methyl-3-(thiophen-2-yl)isoxazole-5-carboxylate (3.9 g, 16.5 mmol), NBS (3.5 g, 19.7 mmol), and benzoyl peroxide (0.4 g, 1.65 mmol) were added to 100 mL of carbon tetrachloride and the mixture was refluxed for 16 h. The reaction mixture was filtered and the filtrate was removed in vacuo. The residue, containing both unreacted starting material and the title compound, was used in the next reaction without purification. MS: (+) m/z 316, 318 (M+1, $^{79}$Br/$^{81}$Br).

e) Ethyl 4-(((2,4-dimethoxybenzyl)(2-ethoxy-2-oxoethyl)amino)methyl)-3-(thiophen-2-yl)isoxazole-5-carboxylate Ethyl 4-(bromomethyl)-3-(thiophen-2-yl)isoxazole-5-carboxylate (16.5 mmol) was dissolved in 35 mL of DMF. N-(2,4-dimethoxybenzyl)glycine ethyl ester (4.2 g, 16.5 mmol) and potassium carbonate (4.5 g, 32.9 mmol) were added, and the mixture was stirred at room temperature for 16 h. EtOAc (100 mL) and water (100 mL) were added and the aqueous layer was extracted with additional EtOAc. The combined organic layer was washed with water and brine, and dried over MgSO$_4$. After solvent was removed in vacuo, the crude was purified by flash chromatography (0-40% EtOAc/hexanes) to give 2.2 g of the title compound. MS: (+) m/z 489.44 (M+1).

f) Ethyl 7-hydroxy-3-(thiophen-2-yl)isoxazolo[4,5-c]pyridine-6-carboxylate

Ethyl 4-(((2,4-dimethoxybenzyl)(2-ethoxy-2-oxoethyl)amino)methyl)-3-(thiophen-2-yl)isoxazole-5-carboxylate (2.2 g, 4.51 mmol) was dissolved in 40 mL of THF and cooled to −78° C. Potassium tert-butoxide solution (9 mL, 9.02 mmol, 1M in THF) was added dropwise, and the mixture was stirred for 14 hours, the cold bath allowed to evaporate spontaneously. The reaction mixture was quenched with 8 mL of 1M HCl and 50 mL of saturated ammonium chloride solution. The product was extracted with EtOAc and the organic layer was dried over MgSO$_4$ and concentrated to give 2.0 g of crude oil. The crude intermediate was dissolved in 25 mL of CH$_2$Cl$_2$. Thionyl chloride (0.49 mL, 6.79 mmol) was added and the reaction mixture was stirred for 3 h. The mixture was filtered through a medium porosity funnel. The solid was rinsed three times with cold CH$_2$Cl$_2$ and dried under vacuum to give 0.88 g of the title compound. MS: (+) m/z 291.34 (M+1).

g) [(7-Hydroxy-3-thiophen-2-yl-isoxazolo[4,5-c]pyridine-6-carbonyl)-amino]-acetic acid Ethyl 7-hydroxy-3-(thiophen-2-yl)isoxazolo[4,5-c]pyridine-6-carboxylate (0.11 g, 0.38 mmol) was dissolved in 10 mL of DMF. Glycine (0.569 g, 7.59 mmol) and sodium ethoxide (0.387 g, 5.69 mmol) were added and the mixture was refluxed for 3 h. The mixture was cooled to room temperature and diluted with 70 mL of water. Concentrated hydrochloric acid was added dropwise until pH was 3. The resulting suspension was filtered and the solid was dried under vacuum to give 92 mg of the title compound. MS: (+) m/z 320.37 (M+1).

Example 48

[(7-Hydroxy-3-pyridin-4-yl-isoxazolo[4,5-c]pyridine-6-carbonyl)-amino]-acetic acid a) 1-(Pyridin-4-yl)propan-1-one oxime Hydroxylamine hydrochloride (2.8 g, 40.7 mmol) and sodium acetate (3.3 g, 40.7 mmol) were added to 20 mL of methanol and the resulting white slurry was stirred at room temperature for 30 min. 1-(Pyridin-4-yl)propan-1-one (5.0 g, 37.0 mmol) was added and the mixture was stirred at room temperature for 20 hours. Water (50 mL) and EtOAc (50 mL) were added and the organic layer was separated. The aqueous layer was basified with solid sodium bicarbonate and extracted with additional EtOAc. The combined organic layer was washed with saturated $NaHCO_3$ solution and dried over $MgSO_4$. The solvent was evaporated in vacuo to give 5.3 g of the title compound. MS: (+) m/z 151.36 (M+1).

b) Ethyl 4-(hydroxyimino)-3-methyl-2-oxo-4-(pyridin-4-yl)butanoate 1-(Pyridin-4-yl)propan-1-one oxime (5.3 g, 35.3 mmol) was dissolved in 120 mL of THF and cooled to 0° C. LDA solution (41 mL, 81.3 mmol, 2M in heptane/THF/ethyl benzene) was added dropwise, and the reaction mixture was stirred at 0° C. for 1.5 hour and then warmed to room temperature. The mixture was then transferred to a syringe and added dropwise to a flask containing a pre-cooled mixture of diethyl oxalate (24 mL, 177 mmol) and THF (100 mL) at 0° C. After the addition was complete, the reaction mixture was stirred at room temperature for 18 hours. The mixture was cooled in an ice bath and quenched with 150 mL of 10% hydrochloric acid. EtOAc (150 mL) was added and solid $NaHCO_3$ was added with vigorous stirring the aqueous layer was basic (pH>8). The aqueous layer was extracted with additional EtOAc and the combined organic layer was dried over $MgSO_4$ and concentrated. The crude product was purified by chromatography (10-60% EtOAc/hexanes) to give 5.3 g of the title compound. MS: (+) m/z 251.43 (M+1).

c) Ethyl 4-methyl-3-(pyridin-4-yl)isoxazole-5-carboxylate

Ethyl 4-(hydroxyimino)-3-methyl-2-oxo-4-(pyridin-4-yl) butanoate (4.68 g, 18.7 mmol) and triethylamine (3.4 mL, 24.3 mmol) were added to 120 mL of $CH_2Cl_2$. Mesyl chloride (1.9 mL, 24.3 mmol) was added and the mixture was stirred at room temperature for 20 h. The reaction mixture was diluted with $CH_2Cl_2$ and saturated sodium bicarbonate solution was added. The aqueous layer was extracted with additional $CH_2Cl_2$ and the combined organic layer was washed with brine and dried over $MgSO_4$. The solvent was removed in vacuo to afford 5.1 g of the title compound. MS: (+) m/z 233.35 (M+1).

d) Ethyl 4-(bromomethyl)-3-(pyridin-4-yl)isoxazole-5-carboxylate

Ethyl 4-methyl-3-(pyridin-4-yl)isoxazole-5-carboxylate (5.1 g, 22.0 mmol), NBS (4.7 g, 26.4 mmol), and benzoyl peroxide (0.53 g, 2.2 mmol) were added to 140 mL of carbon tetrachloride and the mixture was refluxed for 16 h. Solvent was removed in vacuo and the crude product was purified by flash chromatography (10-60% EtOAc/hexanes) to afford 1.5 g of the title compound. MS: (+) m/z 311, 313 (M+1, $^{79}Br/^{81}Br$).

e) Ethyl 4-(((2,4-dimethoxybenzyl)(2-ethoxy-2-oxoethyl)amino)methyl)-3-(pyridin-4-yl)isoxazole-5-carboxylate Ethyl 4-(bromomethyl)-3-(pyridin-4-yl)isoxazole-5-carboxylate (1.5 g, 4.82 mmol) was dissolved in 20 mL of DMF. N-(2,4-dimethoxybenzyl)glycine ethyl ester (1.22 g, 4.82 mmol) and potassium carbonate (1.33 g, 9.65 mmol) were added, and the mixture was stirred at room temperature for 16 h. EtOAc (100 mL) and water (100 mL) were added and the aqueous layer was extracted with additional EtOAc. The combined organic layer was washed with water and brine, and dried over $MgSO_4$. After solvent was removed in vacuo, the crude was purified by flash chromatography (0-50% EtOAc/hexanes) to give 0.49 g of the title compound. MS: (+) m/z 484.48 (M+1).

f) Ethyl 7-hydroxy-3-(pyridin-4-yl)isoxazolo[4,5-c]pyridine-6-carboxylate

Ethyl 4-(((2,4-dimethoxybenzyl)(2-ethoxy-2-oxoethyl)amino)methyl)-3-(pyridin-4-yl)isoxazole-5-carboxylate (0.49 g, 1.01 mmol) was dissolved in 20 ml, of THF and cooled to −78° C. Potassium tert-butoxide solution (2 mL, 2.02 mmol, 1M in THF) was added dropwise, and the mixture was stirred for 14 hours, the cold bath allowed to evaporate spontaneously. The reaction mixture was quenched with 2 ml, of 1M HCl and 50 mL of saturated ammonium chloride solution. The resulting mixture was then neutralized with solid sodium bicarbonate and extracted with EtOAc. The organic layer was dried over $MgSO_4$ and concentrated to give 0.26 g of solid. The crude intermediate was dissolved in 3 ml, of $CH_2Cl_2$. Thionyl chloride (0.064 mL, 0.88 mmol) was added and the reaction mixture was stirred for 5 h. The mixture was filtered through a medium porosity funnel. The solid was rinsed three times with cold $CH_2Cl_2$ and dried under vacuum to give 95 mg of the title compound. MS: (+) m/z 286.38 (M+1).

g) [(7-Hydroxy-3-pyridin-4-yl-isoxazolo[4,5-c]pyridine-6-carbonyl)-amino]-acetic acid Ethyl 7-hydroxy-3-(pyridin-4-yl)isoxazolo[4,5-c]pyridine-6-carboxylate (95 mg, 0.33 mmol) was dissolved in 10 mL of DMF. Glycine (500 mg, 6.67 mmol) and sodium ethoxide (340 mg, 5.0 mmol) were added and the mixture was refluxed for 2 h. The mixture was cooled to room temperature and diluted with 50 mL of water. Concentrated hydrochloric acid was added dropwise until pH was 3. EtOAc (50 mL) was added to the resulting suspension, and the mixture was transferred to a separatory funnel. The aqueous layer was removed, and the organic layer, which contained an insoluble solid, was filtered. The solid was dried under vacuum to give 30 mg of the title compound. MS: (+) m/z 315.34 (M+1).

Example 49

{[3-(5-Bromo-furan-2-yl)-7-hydroxy-isoxazolo[4,5-c]pyridine-6-carbonyl]-amino}-acetic acid a) 1-(Furan-2-yl)propan-1-one oxime Hydroxylamine hydrochloride (3.3 g, 47.8 mmol) and sodium acetate (3.9 g, 47.8 mmol) were added to 20 mL of methanol and the resulting white slurry was stirred at room temperature for 30 min. 1-(Furan-2-yl)propan-1-one (5.4 g, 43.5 mmol) was added and the mixture was stirred at room temperature for 20 hours. Water (20 mL) was added and the product was extracted with EtOAc and the organic layer was washed with saturated $NaHCO_3$ solution and dried over $MgSO_4$. The solvent was evaporated in vacuo to give 6.1 g of the title compound.

b) Ethyl 4-(furan-2-yl)-4-(hydroxyimino)-3-methyl-2-oxobutanoate 1-(Furan-2-yl)propan-1-one oxime (6.1 g, 43.9 mmol) was dissolved in 100 mL of THF and cooled to 0° C. LDA solution (55 mL, 110 mmol, 2M in heptane/THF/ethyl benzene) was added dropwise, and the reaction mixture was stirred at 0° C. for 1 hour and then warmed to room temperature. The mixture was then transferred to an addition funnel and added dropwise to a flask containing a pre-cooled mixture of diethyl oxalate (30 mL, 219 mmol) and THF (100 mL) at 0° C. After the addition was complete, the reaction mixture was stirred at room temperature for 18 hours. The mixture was cooled in an ice bath and quenched with 150 mL of 10% hydrochloric acid. The organic layer was separated and the aqueous layer was extracted with EtOAc. The aqueous layer was then neutralized with solid sodium bicarbonate and extracted further with $CH_2Cl_2$. The organic layers were combined, dried over $MgSO_4$ and concentrated. The crude oil was purified by chromatography (0-40% EtOAc/hexanes) to give 10 g of the title compound. MS: (+) m/z 240.42 (M+1).

c) Ethyl 3-(furan-2-yl)-4-methylisoxazole-5-carboxylate

Ethyl 4-(furan-2-yl)-4-(hydroxyimino)-3-methyl-2-oxobutanoate (10 g, 41.8 mmol) and concentrated sulfuric acid (10 mL) were added to 150 mL of absolute ethanol and the mixture was refluxed for 20 hours. After the mixture cooled to room temperature, saturated sodium bicarbonate solution was added to neutralize the mixture. The product was extracted with EtOAc and the combined organic layer was dried over $MgSO_4$ and concentrated to give 5.8 g of the title compound. MS: (+) m/z 222.40 (M+1).

d) Ethyl 3-(5-bromofuran-2-yl)-4-methylisoxazole-5-carboxylate

Ethyl 3-(furan-2-yl)-4-methylisoxazole-5-carboxylate (5.8 g, 26.2 mmol), NBS (5.6 g, 31.5 mmol), and benzoyl peroxide (0.64 g, 2.62 mmol) were added to 150 mL of carbon tetrachloride and the mixture was refluxed for 16 h. Reaction mixture was filtered and concentrated. The residue was purified by flash chromatography (0-30% EtOAc/hexanes) to give 1.7 g of the title compound. MS: (+) m/z 300.31, 322.28 (M+1, $^{79}Br/^{81}Br$).

e) Ethyl 3-(5-bromofuran-2-yl)-4-(bromomethyl)isoxazole-5-carboxylate

Ethyl 3-(5-bromofuran-2-yl)-4-methylisoxazole-5-carboxylate (1.7 g, 5.67 mmol), NBS (1.2 g, 6.8 mmol), and benzoyl peroxide (0.14 g, 0.567 mmol) were added to 50 mL of carbon tetrachloride and the mixture was refluxed for 16 h. Reaction mixture was concentrated and purified by chromatography (0-30% EtOAc/hexanes) to give 1.8 g of the title compound along with small amount of unreacted starting material. $^1$H NMR (CDCl$_3$, 200 MHz): δ=7.09 (d, 1H, J=3.4 Hz), 6.54 (d, 1H, J=3.6 Hz), 4.84 (s, 2H), 4.51 (q, 2H, J=7.0 Hz), 1.49 (t, 3H, J=7.4 Hz).

f) Ethyl 3-(5-bromofuran-2-yl)-4-(((2,4-dimethoxybenzyl)(2-ethoxy-2-oxoethyl)amino)methyl)isoxazole-5-carboxylate Ethyl 3-(5-bromofuran-2-yl)-4-(bromomethyl)isoxazole-5-carboxylate (1.8 g, 4.75 mmol) was dissolved in 20 mL of DMF. N-(2,4-dimethoxybenzyl)glycine ethyl ester (1.2 g, 4.75 mmol) and potassium carbonate (1.3 g, 9.50 mmol) were added, and the mixture was stirred at room temperature for 16 h. EtOAc (50 mL) and water (50 mL) were added and the aqueous layer was extracted with additional EtOAc. The combined organic layer was washed with water and brine, and dried over $MgSO_4$. After solvent was removed in vacuo, the crude was purified by flash chromatography (0-40% EtOAc/hexanes) to give 1.53 g of the title compound. MS: (+) m/z 551.44, 553.35 (M+1, $^{79}Br/^{81}Br$).

g) Ethyl 3-(5-bromofuran-2-yl)-7-hydroxyisoxazolo[4,5-c]pyridine-6-carboxylate Ethyl 3-(5-bromofuran-2-yl)-4-(((2,4-dimethoxybenzyl)(2-ethoxy-2-oxoethyl)amino)methyl)isoxazole-5-carboxylate (1.53 g, 2.78 mmol) was dissolved in 30 mL of THF and cooled to −78° C. Potassium tert-butoxide solution (5.6 mL, 5.55 mmol, 1M in THF) was added dropwise, and the mixture was stirred for 14 hours, the cold bath allowed to evaporate spontaneously. The reaction mixture was quenched with 5 mL of 1M HCl and 100 mL of saturated ammonium chloride solution. The product was extracted with EtOAc and the organic layer was dried over $MgSO_4$ and concentrated to give 1.32 g of crude oil. The crude intermediate was dissolved in 15 mL of $CH_2Cl_2$. Thionyl chloride (0.29 mL, 3.92 mmol) was added and the reaction mixture was stirred for 4 h. The mixture was filtered through a medium porosity funnel. The solid was rinsed three times with cold $CH_2Cl_2$ and dried under vacuum to give 63 mg of the title compound. The filtrate was concentrated and the residue was partitioned between EtOAc and saturated sodium bicarbonate solution. The aqueous layer was extracted with additional EtOAc and the combined organic layer was dried over $MgSO_4$ and concentrated. The residue was purified by flash chromatography (0-40% EtOAc/hexanes) to give additional 443 mg of the title compound. δ=11.4 (s, 1H), 8.98 (s, 1H), 7.20-7.24 (m, 1H), 6.58-6.65 (m, 1H), 4.61 (q, 2H, J=7.0 Hz), 1.55 (t, 3H, J=7.0 Hz).

h) {[3-(5-Bromo-furan-2-yl)-7-hydroxy-isoxazolo[4,5-c]pyridine-6-carbonyl]-amino}-acetic acid Ethyl 3-(5-bromofuran-2-yl)-7-hydroxyisoxazolo[4,5-c]pyridine-6-carboxylate (62 mg, 0.176 mmol) was dissolved in 10 mL of DMF. Glycine (0.264 g, 3.51 mmol) and sodium ethoxide (0.179 g, 2.63 mmol) were added and the mixture was refluxed for 3 h. The mixture was cooled to room temperature and diluted with 70 mL of water. Concentrated hydrochloric acid was added dropwise until pH was 3. The resulting suspension was filtered and the solid was dried under vacuum to give 62 mg of the title compound. MS: (+) m/z 382, 384 (M+1, $^{79}Br/^{81}Br$).

Example 50

[(7-Hydroxy-4-methyl-3-phenyl-isoxazolo[4,5-c]pyridine-6-carbonyl)-amino]-acetic acid a) Ethyl 4-bromo-7-hydroxy-3-phenylisoxazolo[4,5-c]pyridine-6-carboxylate

Ethyl 7-hydroxy-3-phenylisoxazolo[4,5-c]pyridine-6-carboxylate (1.0 g, 3.52 mmol), NBS (0.94 g, 5.28 mmol), and benzoyl peroxide (85 mg, 0.352 mmol) were added to 30 mL of carbon tetrachloride and refluxed for 16 h. Silica gel (10 g) was added and the solvent was evaporated. The crude was purified by flash chromatography (0-40% EtOAc/hexanes) to give 780 mg of the title compound. MS: (+) m/z 363.26, 365.17 (M+1, $^{79}$Br/$^{81}$Br).

b) Ethyl 7-hydroxy-4-methyl-3-phenylisoxazolo[4,5-c]pyridine-6-carboxylate

A nitrogen flushed flask was charged with ethyl 4-bromo-7-hydroxy-3-phenylisoxazolo[4,5-c]pyridine-6-carboxylate (150 mg, 0.413 mmol), DMF (2 mL), tetramethylstannane (0.17 mL, 1.24 mmol), and Pd(PPh$_3$)$_2$Cl$_2$ (58 mg, 0.083 mmol). The mixture was heated in an oil bath (bath temperature=120-130° C.) for 2 hours. After the reaction mixture was cooled to room temperature, it was purified by flash chromatography (0-30% EtOAc/hexanes) to afford 41 mg of the title compound. MS: (+) m/z 299.43 (M+1).

c) [(7-Hydroxy-4-methyl-3-phenyl-isoxazolo[4,5-c]pyridine-6-carbonyl)-amino]-acetic acid Ethyl 7-hydroxy-4-methyl-3-phenylisoxazolo[4,5-c]pyridine-6-carboxylate (41 mg, 0.138 mmol) was dissolved in 5 mL of DMF. Glycine (207 mg, 2.75 mmol) and sodium ethoxide (140 mg, 2.06 mmol) were added and the mixture was refluxed for 2 h. The mixture was cooled to room temperature and diluted with 30 mL of water. Concentrated hydrochloric acid was added dropwise until pH was 3. The aqueous phase was extracted with EtOAc and the combined organic layer was dried over MgSO$_4$ and concentrated to give 35 mg of pale yellow solid. The solid was dissolved in saturated NaHCO$_3$ (10 mL) and washed with hexanes and EtOAc. The aqueous phase was acidified to pH 3 with concentrated HCl and extracted with EtOAc. The organic layer was dried and concentrated to give 15 mg of the title compound. MS: (+) m/z 328.39 (M+1).

Example 51

[(4-Cyano-7-hydroxy-3-thiophen-2-yl-isoxazolo[4,5-c]pyridine-6-carbonyl)-amino]-acetic acid a) Ethyl 7-hydroxy-4-iodo-3-(thiophen-2-yl)isoxazolo[4,5-c]pyridine-6-carboxylate Ethyl 7-hydroxy-3-(thiophen-2-yl)isoxazolo[4,5-c]pyridine-6-carboxylate (350 mg, 1.21 mmol) was dissolved in 15 mL of CH$_2$Cl$_2$. Bis(sym-collidine)iodine hexafluorophosphate (1.24 g, 2.41 mmol) was added and the resulting mixture was stirred in the dark at room temperature for 16 h. The mixture was diluted with CH$_2$Cl$_2$ (20 mL), and 2 g of silica gel was added. The solvent was removed in vacuo and the crude product was purified by flash chromatography (0-10% MeOH/CH$_2$Cl$_2$). Fractions containing the title compound were combined and washed with 10% sodium metasulfite, and then dried over MgSO$_4$. The solvent was removed in vacuo to afford 310 mg of the title compound. MS: (+) m/z 417.18 (M+1).

b) Ethyl 4-cyano-7-hydroxy-3-(thiophen-2-yl)isoxazolo[4,5-c]pyridine-6-carboxylate Ethyl 7-hydroxy-4-iodo-3-(thiophen-2-yl)isoxazolo[4,5-c]pyridine-6-carboxylate (310 mg, 0.745 mmol) and CuCN (200 mg, 2.24 mmol) were added to 5 mL of N-methyl-2-pyrrolidone. The resulting suspension was heated in an oil bath (T=110° C.) for 1 h. The reaction mixture was cooled slightly and poured into a vigorously stirring mixture of ammonium hydroxide (4 mL, 15% aqueous solution) and EtOAc (100 mL). The mixture was acidified with concentrated hydrochloric acid to pH 3 and extracted with EtOAc. The combined organic layer was dried over MgSO$_4$ and concentrated, and the residue was purified flash chromatography (0-100% EtOAc/hexanes) to afford 136 mg of the title compound. MS: (+) m/z 316.29 (M+1).

c) [(4-Cyano-7-hydroxy-3-thiophen-2-yl-isoxazolo[4,5-c]pyridine-6-carbonyl)-amino]-acetic acid Ethyl 4-cyano-7-hydroxy-3-(thiophen-2-yl)isoxazolo[4,5-c]pyridine-6-carboxylate (136 mg, 0.432 mmol) and glycine (648 mg, 8.63 mmol) were added to sodium methoxide solution (13 mL, 6.48 mmol, 0.5 M in MeOH) and the mixture was refluxed for 3 days. The mixture was cooled to room temperature and 0.25 M hydrochloric acid was added until pH was 3. The precipitate was isolated by filtration and dried under vacuum to give 101 mg of the title compound. MS: (−) m/z 343.28 (M−1).

Example 52

{[4-Cyano-3-(4-fluoro-phenyl)-7-hydroxy-isoxazolo[4,5-c]pyridine-6-carbonyl]-amino}-acetic acid a) Ethyl 3-(4-fluorophenyl)-7-hydroxy-4-iodoisoxazolo[4,5-c]pyridine-6-carboxylate Ethyl 3-(4-fluorophenyl)-7-hydroxyisoxazolo[4,5-c]pyridine-6-carboxylate (302 mg, 1.0 mmol) was dissolved in 14 mL of CH$_2$Cl$_2$. Bis(sym-collidine)iodine hexafluorophosphate (1.19 g, 2.32 mmol) was added and the resulting mixture was stirred in the dark at room temperature for 16 h. The mixture was diluted with CH$_2$Cl$_2$ (20 mL), and 2 g of silica gel was added. The solvent was removed in vacuo and the crude product was purified by flash chromatography (0-10% MeOH/CH$_2$Cl$_2$). Fractions containing the title compound were combined and washed with 10% sodium metasulfite, and then dried over MgSO$_4$. The solvent was removed in vacuo to afford 290 mg of the title compound. MS: (+) m/z 429.21 (M+1).

b) Ethyl 4-cyano-3-(4-fluorophenyl)-7-hydroxyisoxazolo[4,5-c]pyridine-6-carboxylate Ethyl 3-(4-fluorophenyl)-7-hydroxy-4-iodoisoxazolo[4,5-c]pyridine-6-carboxylate (290 mg, 0.678 mmol) and CuCN (182 mg, 2.03 mmol) were added to 4.5 mL of N-methyl-2-pyrrolidone. The resulting suspension was heated in an oil bath (T=110° C.) for 1 h. The reaction mixture was cooled slightly and poured into a vigorously stirring mixture of ammonium hydroxide (4 mL, 15% aqueous solution) and EtOAc (100 mL). The mixture was acidified with concentrated hydrochloric acid to pH 3 and extracted with EtOAc. The combined organic layer was dried over MgSO$_4$ and concentrated, and the residue was purified flash chromatography (0-100% EtOAc/hexanes) to afford 101 mg of the title compound. MS: (+) m/z 328.32 (M+1).

c) {[4-Cyano-3-(4-fluoro-phenyl)-7-hydroxy-isoxazolo[4,5-c]pyridine-6-carbonyl]-amino}-acetic acid Ethyl 4-cyano-3-(4-fluorophenyl)-7-hydroxyisoxazolo[4,5-c]pyridine-6-carboxylate (101 mg, 0.309 mmol) and glycine (468 mg, 6.18 mmol) were added to sodium methoxide solution (9.3 mL, 4.63 mmol, 0.5 M in MeOH) and the mixture was refluxed for 3 days. The mixture was cooled to room temperature and 0.25 M hydrochloric acid was added until pH was 3. The precipitate was isolated by filtration and dried under vacuum to give 73 mg of the title compound. MS: (−) m/z 355.31 (M−1).

Example 53

{[4-Cyano-7-hydroxy-3-(4-methoxy-phenyl)-isoxazolo[4,5-c]pyridine-6-carbonyl]-amino}-acetic acid a) Ethyl 7-hydroxy-4-iodo-3-(4-methoxyphenyl) isoxazolo[4,5-c]pyridine-6-carboxylate Ethyl 7-hydroxy-3-(4-methoxyphenyl)isoxazolo[4,5-c]pyridine-6-carboxylate (500 mg, 1.59 mmol) was dissolved in 20 mL of $CH_2Cl_2$. Bis(sym-collidine)iodine hexafluorophosphate (1.64 g, 3.18 mmol) was added and the resulting mixture was stirred in the dark at room temperature for 16 h. The mixture was diluted with $CH_2Cl_2$ (100 mL), and 10 g of silica gel was added. The solvent was removed in vacuo and the crude product was purified by flash chromatography (0-10% MeOH/$CH_2Cl_2$). Fractions containing the title compound were combined and washed with 10% sodium metasulfite, and then dried over $MgSO_4$. The solvent was removed in vacuo to afford 400 mg of the title compound. MS: (+) m/z 441.24 (M+1).

b) Ethyl 4-cyano-7-hydroxy-3-(4-methoxyphenyl) isoxazolo[4,5-c]pyridine-6-carboxylate Ethyl 7-hydroxy-4-iodo-3-(4-methoxyphenyl)isoxazolo[4,5-c]pyridine-6-carboxylate (390 mg, 0.89 mmol) and CuCN (238 mg, 2.66 mmol) were added to 6 mL of N-methyl-2-pyrrolidone. The resulting suspension was heated in an oil bath (T=110° C.) for 1 h. The reaction mixture was cooled slightly and poured into a vigorously stirring mixture of ammonium hydroxide (100 mL, 30% aqueous solution) and EtOAc (100 mL). The mixture was acidified with concentrated hydrochloric acid to pH 3 and extracted with EtOAc. The combined organic layer was dried over $MgSO_4$ and concentrated, and the residue was purified flash chromatography (0-100% EtOAc/hexanes) to afford 178 mg of the title compound. MS: (+) m/z 340.42 (M+1).

c) {[4-Cyano-7-hydroxy-3-(4-methoxy-phenyl)-isoxazolo[4,5-c]pyridine-6-carbonyl]-amino}-acetic acid Ethyl 4-cyano-7-hydroxy-3-(4-methoxyphenyl)isoxazolo[4,5-c]pyridine-6-carboxylate (86 mg, 0.254 mmol) and glycine (381 mg, 5.07 mmol) were added to sodium methoxide solution (7.6 mL, 3.80 mmol, 0.5 M in MeOH) and the mixture was refluxed for 3 days. The mixture was cooled to room temperature and 0.25 M hydrochloric acid was added until pH was 3. The precipitate was isolated by filtration and dried under vacuum to give 75 mg of crude solid. The solid was dissolved in 200 mL of saturated sodium bicarbonate solution and washed with EtOAc. The aqueous layer was acidified to pH 3 with concentrated hydrochloric acid and the precipitate was collected by filtration. The solid was dried under vacuum to afford 67 mg of the title compound. MS: (−) m/z 367.34 (M−1).

Example 54

{[3-(5-Bromo-furan-2-yl)-4-cyano-7-hydroxy-isoxazolo[4,5-c]pyridine-6-carbonyl]-amino}-acetic acid a) Ethyl 3-(5-bromofuran-2-yl)-7-hydroxy-4-iodo-isoxazolo[4,5-c]pyridine-6-carboxylate Ethyl 3-(5-bromofuran-2-yl)-7-hydroxyisoxazolo[4,5-c]pyridine-6-carboxylate (250 mg, 0.71 mmol) was dissolved in 10 mL of $CH_2Cl_2$. Bis(sym-collidine)iodine hexafluorophosphate (728 mg, 1.42 mmol) was added and the resulting mixture was stirred in the dark at room temperature for 16 h. The mixture was diluted with $CH_2Cl_2$ (20 mL), and 2 g of silica gel was added. The solvent was removed in vacuo and the crude product was purified by flash chromatography (0-100% EtOAc/hexanes) to give 155 mg of the title compound. MS: (+) m/z 479.11, 481.08 (M+1, $^{79}Br/^{81}Br$).

b) Ethyl 3-(5-bromofuran-2-yl)-4-cyano-7-hydroxy-isoxazolo[4,5-c]pyridine-6-carboxylate Ethyl 3-(5-bromofuran-2-yl)-7-hydroxy-4-iodoisoxazolo[4,5-c]pyridine-6-carboxylate (155 mg, 0.324 mmol) and CuCN (87 mg, 0.971 mmol) were added to 2.2 mL of N-methyl-2-pyrrolidone. The resulting suspension was heated in an oil bath (T=110° C.) for 1 h. The reaction mixture was cooled slightly and poured into a vigorously stirring mixture of ammonium hydroxide (5 mL, 15% aqueous solution) and EtOAc (50 mL). The mixture was acidified with concentrated hydrochloric acid to pH 3 and extracted with EtOAc. The combined organic layer was dried over $MgSO_4$ and concentrated, and the residue was purified flash chromatography (0-100% EtOAc/hexanes) to afford 42 mg of the title compound. MS: (+) m/z 378.29, 380.26 (M+1, $^{79}Br/^{81}Br$).

c) {[3-(5-Bromo-furan-2-yl)-4-cyano-7-hydroxy-isoxazolo[4,5-c]pyridine-6-carbonyl]-amino}-acetic acid Ethyl 3-(5-bromofuran-2-yl)-4-cyano-7-hydroxyisoxazolo[4,5-c]pyridine-6-carboxylate (42 mg, 0.11 mmol) and glycine (334 mg, 4.44 mmol) were added to sodium methoxide solution (6.7 mL, 3.33 mmol, 0.5 M in MeOH) and the mixture was refluxed for 48 h. The mixture was cooled to room temperature and the solvent was removed in vacuo. The residue was redissolved in a minimum amount of water, and 0.25 M hydrochloric acid was added until pH was 3. The resulting precipitate was isolated by filtration and dried under vacuum to give 21 mg of crude solid. The solid was dissolved in 10 mL of saturated sodium bicarbonate solution and washed with hexanes and EtOAc. The aqueous layer was acidified to pH 3 and extracted with EtOAc. The combined organic layer was dried over $MgSO_4$ and concentrated to afford 10 mg of the title compound. MS: (−) m/z 405.21, 407.18 (M−1, $^{79}Br/^{81}Br$).

Example 55

{[7-Hydroxy-3-(4-methoxy-phenyl)-4-phenyl-isoxazolo[4,5-c]pyridine-6-carbonyl]-amino}-acetic acid a) Ethyl 7-hydroxy-3-(4-methoxyphenyl)-4-phenyl-isoxazolo[4,5-c]pyridine-6-carboxylate Ethyl 7-hydroxy-4-iodo-3-(4-methoxyphenyl)isoxazolo[4,5-c]pyridine-6-carboxylate (200 mg, 0.45 mmol), phenylboronic acid (111 mg, 0.91 mmol), Pd(PPh$_3$)$_4$ (105 mg, 0.091 mmol) and cesium carbonate (444 mg, 1.36 mmol) were added to a flask and the flask evacuated. After refilling with nitrogen, 3 mL of 1,2-dimethoxyethane was added and the resulting suspension was refluxed for 16 h. The reaction mixture diluted with EtOAc (50 mL) and the solid was filtered. The solid was added to a mixture of 10% hydrochloric acid and extracted several times with EtOAc. The combined organic layer was dried over MgSO$_4$ and concentrated, and the residue was purified flash chromatography (0-40% EtOAc/hexanes) to afford 68 mg of the title compound. MS: (+) m/z 391.41 (M+1).

b) {[7-Hydroxy-3-(4-methoxy-phenyl)-4-phenyl-isoxazolo[4,5-c]pyridine-6-carbonyl]-amino}-acetic acid Ethyl 7-hydroxy-3-(4-methoxyphenyl)-4-phenylisoxazolo[4,5-c]pyridine-6-carboxylate (70 mg, 0.18 mmol) and glycine (539 mg, 7.18 mmol) were added to sodium methoxide solution (10.8 mL, 5.38 mmol, 0.5 M in MeOH) and the mixture was refluxed for 3 days. The mixture was cooled to room temperature and the solvent was removed in vacuo. The residue was dissolved in minimum amount of water and 0.25 M hydrochloric acid was added until pH was 3. The precipitate was isolated by filtration and dried under vacuum to give 79 mg of crude solid. The solid was dissolved in 15 mL of saturated sodium bicarbonate solution and washed with hexanes and EtOAc. The aqueous layer was acidified to pH 3 with concentrated hydrochloric acid and the precipitate was collected by filtration. The solid was dried under vacuum to afford 47 mg of the title compound. MS: (+) m/z 420.37 (M+1).

Example 56

{[7-Hydroxy-3-(4-methoxy-phenyl)-4-methyl-isoxazolo[4,5-c]pyridine-6-carbonyl]-amino}-acetic acid a) Ethyl 7-hydroxy-3-(4-methoxyphenyl)-4-methyl-isoxazolo[4,5-c]pyridine-6-carboxylate Ethyl 7-hydroxy-4-iodo-3-(4-methoxyphenyl)isoxazolo[4,5-c]pyridine-6-carboxylate (280 mg, 0.64 mmol), methylboronic acid (155 mg, 127 mmol), Pd(PPh$_3$)$_4$ (147 mg, 0.13 mmol) and cesium carbonate (622 mg, 1.91 mmol) were added to a flask and the flask evacuated. After refilling with nitrogen, 6.5 mL of 1,2-dimethoxyethane was added and the resulting suspension was refluxed for 16 h. The reaction mixture diluted with EtOAc (40 mL) and the solid was filtered. The solid was added to a mixture of 10% hydrochloric acid and extracted several times with EtOAc. The combined organic layer was dried over MgSO$_4$ and concentrated, and the residue was purified flash chromatography (0-40% EtOAc/hexanes) to afford 35 mg of the title compound. MS: (+) m/z 329.41 (M+1).

b) {[7-Hydroxy-3-(4-methoxy-phenyl)-4-methyl-isoxazolo[4,5-c]pyridine-6-carbonyl]-amino}-acetic acid Ethyl 7-hydroxy-3-(4-methoxyphenyl)-4-methylisoxazolo[4,5-c]pyridine-6-carboxylate (35 mg, 0.11 mmol) and glycine (320 mg, 4.27 mmol) were added to sodium methoxide solution (6.4 mL, 3.20 mmol, 0.5 M in MeOH) and the mixture was refluxed for 3 days. The mixture was cooled to room temperature and the solvent was removed in vacuo. The residue was dissolved in minimum amount of water and 0.25 M hydrochloric acid was added until pH was 3. The precipitate was isolated by filtration and dried under vacuum to give 22 mg of crude solid. The solid was dissolved in 10 mL of saturated sodium bicarbonate solution and washed with hexanes and EtOAc. The aqueous layer was acidified to pH 3 with concentrated hydrochloric acid and extracted with EtOAc. The organic layer was dried over MgSO$_4$ and concentrated to give 19 mg of the title compound. MS: (+) m/z 358.37 (M+1).

Example 57

[(7-Hydroxy-3-phenyl-4-phenylethynyl-isoxazolo[4,5-c]pyridine-6-carbonyl)-amino]-acetic acid a) Ethyl 7-hydroxy-4-iodo-3-phenylisoxazolo[4,5-c]pyridine-6-carboxylate

Ethyl 7-hydroxy-3-phenylisoxazolo[4,5-c]pyridine-6-carboxylate (1.5 g, 5.28 mmol) was dissolved in 70 mL of CH$_2$Cl$_2$. Bis(sym-collidine)iodine hexafluorophosphate (5.4 g, 10.6 mmol) was added and the resulting mixture was stirred in the dark at room temperature for 16 h. The mixture was diluted with CH$_2$Cl$_2$ (50 mL), and 10 g of silica gel was added. The solvent was removed in vacuo and the crude product was purified by flash chromatography (0-10% MeOH/CH$_2$Cl$_2$). Fractions containing the title compound were combined and concentrated. The residue was redissolved in 50 mL of CH$_2$Cl$_2$ and washed with 10% sodium metasulfite, and the organic layer was dried over MgSO$_4$. The solvent was removed in vacuo to afford 1.68 g of the title compound. MS: (+) m/z 411.13 (M+1).

b) Ethyl 7-hydroxy-3-phenyl-4-(phenylethynyl)isoxazolo[4,5-c]pyridine-6-carboxylate Ethyl 7-hydroxy-4-iodo-3-phenylisoxazolo[4,5-c]pyridine-6-carboxylate (300 mg, 0.73 mmol), copper iodide (56 mg, 0.29 mmol), and PdCl$_2$(PPh$_3$)$_2$ (103 mg, 0.15 mmol) were added to a flask and the flask evacuated. After refilling with nitrogen, THF (5 mL), diisopropylamine (0.6 mL) and phenylacetylene (0.1 mL, 0.95 mmol) were added and the resulting mixture was stirred at room temperature for 16 h. The solvent was removed in vacuo and the residue was partitioned between 25 mL of 1M hydrochloric acid and 25 mL of EtOAc. The aqueous layer was extracted with additional EtOAc and the combined organic layer was dried over MgSO$_4$ and concentrated. The residue was purified flash chromatography (0-40% EtOAc/hexanes) to afford 195 mg of the title compound. MS: (+) m/z 385.29 (M+1).

c) [(7-Hydroxy-3-phenyl-4-phenylethynyl-isoxazolo[4,5-c]pyridine-6-carbonyl)-amino]-acetic acid Ethyl 7-hydroxy-3-phenyl-4-(phenylethynyl)isoxazolo[4,5-c]pyridine-6-carboxylate (195 mg, 0.51 mmol) and glycine (1.9 g, 25.3 mmol) were added to sodium methoxide solution (38 mL, 19.0 mmol, 0.5 M in MeOH) and the mixture was refluxed for 3 days. The mixture was cooled to room temperature and the solvent was removed in vacuo. The residue was dissolved in 100 mL of water and hydrochloric acid was added until pH was 3. The precipitate was isolated by filtration and dried under vacuum to give 173 mg of the title compound. MS: (+) m/z 414.32 (M+1).

Example 58

[(4-Ethynyl-7-hydroxy-3-phenyl-isoxazolo[4,5-c]
pyridine-6-carbonyl)-amino]-acetic acid a) Ethyl 7-hydroxy-3-phenyl-4-((trimethylsilyl)ethynyl)isoxazolo[4,5-c]pyridine-6-carboxylate Ethyl 7-hydroxy-4-iodo-3-phenylisoxazolo[4,5-c]pyridine-6-carboxylate (500 mg, 1.22 mmol), copper iodide (93 mg, 0.49 mmol), and PdCl$_2$(PPh$_3$)$_2$ (171 mg, 0.24 mmol) were added to a flask and the flask evacuated. After refilling with nitrogen, THF (20 mL), diisopropylamine (1 mL) and TMS acetylene (0.35 mL, 2.44 mmol) were added and the resulting mixture was stirred at room temperature for 16 h. The solvent was removed in vacuo and the residue was partitioned between 25 mL of 1M hydrochloric acid and 25 mL of EtOAc. The aqueous layer was extracted with additional EtOAc and the combined organic layer was dried over MgSO$_4$ and concentrated. The residue was purified flash chromatography (0-100% CH$_2$Cl$_2$/hexanes) to afford 405 mg of the title compound. MS: (+) m/z 381.35 (M+1).

b) [(4-Ethynyl-7-hydroxy-3-phenyl-isoxazolo[4,5-c]
pyridine-6-carbonyl)-amino]-acetic acid Ethyl 7-hydroxy-3-phenyl-4-((trimethylsilyl)ethynyl)isoxazolo[4,5-c]pyridine-6-carboxylate (200 mg, 0.53 mmol) was added to sodium methoxide solution (39.5 mL, 19.7 mmol, 0.5 M in MeOH) and the mixture was refluxed for 30 min. After the mixture was cooled to room temperature, glycine (1.98 g, 26.3 mmol) was added, and the mixture was refluxed for 48 h. The mixture was cooled to room temperature and the solvent was removed in vacuo. The residue was dissolved in 100 mL of water and hydrochloric acid was added until pH was 3. The precipitate was isolated by filtration and dried under vacuum to give 170 mg of crude solid. The solid was dissolved in 100 mL of saturated sodium bicarbonate solution and washed with EtOAc. The aqueous layer was acidified with concentrated hydrochloric acid to pH 3 and extracted with EtOAc. The solvent was concentrated in vacuo to give 116 mg of the title compound. MS: (−) m/z 336.28 (M−1).

Example 59

[(4-Cyclopropyl-7-hydroxy-3-thiophen-2-yl-isoxazolo[4,5-c]pyridine-6-carbonyl)-amino]-acetic acid a) Ethyl 4-cyclopropyl-7-hydroxy-3-(thiophen-2-yl)isoxazolo[4,5-c]pyridine-6-carboxylate Ethyl 7-hydroxy-4-iodo-3-(thiophen-2-yl)isoxazolo[4,5-c]pyridine-6-carboxylate (300 mg, 0.72 mmol), cyclopropylboronic acid (74 mg, 0.87 mmol), K$_3$PO$_4$ (505 mg, 2.38 mmol) and Pd(PPh$_3$)$_4$ (83 mg, 0.072 mmol) were added to a flask, and the flask evacuated. After refilling with nitrogen, toluene (4 mL) and water (43 µl, 2.38 mmol) were added, and the resulting suspension was heated in an oil bath (T=100° C.) for 18 h. After the mixture was cooled to room temperature, the mixture was diluted with EtOAc (50 mL) and the solid was removed by filtration. The filtrate was concentrated and the residue was purified first by flash chromatography (0-40% EtOAc/hexanes), then by preparative TLC (eluted with 40% EtOAc/hexanes), to afford 47 mg of the title compound. MS: (+) m/z 331.24 (M+1).

b) [(4-Cyclopropyl-7-hydroxy-3-thiophen-2-yl-isoxazolo[4,5-c]pyridine-6-carbonyl)-amino]-acetic acid Ethyl 4-cyclopropyl-7-hydroxy-3-(thiophen-2-yl)isoxazolo[4,5-c]pyridine-6-carboxylate (47 mg, 0.142 mmol) and glycine (428 mg, 5.70 mmol) were added to sodium methoxide solution (8.5 mL, 4.27 mmol, 0.5 M in MeOH) and the mixture was refluxed for 48 h. The mixture was cooled to room temperature and the solvent was removed in vacuo. The residue was redissolved in 10 mL of water and acidified to pH 3 by addition of concentrated hydrochloric acid. The resulting precipitate was isolated by filtration to give 51 mg of crude solid. The solid was dissolved in saturated sodium bicarbonate (20 mL), and washed with EtOAc. The aqueous layer was acidified to pH 3 with 4M HCl and extracted with EtOAc. The combined organic layer was dried over MgSO$_4$ and concentrated to give 36 mg of the title compound. MS: (−) m/z 358.30 (M−1).

Example 60

{[7-Hydroxy-3-(4-methoxy-phenyl)-4-pyrazol-1-ylmethyl-isoxazolo[4,5-c]pyridine-6-carbonyl]-amino}-acetic acid a) Ethyl 3-(4-methoxyphenyl)-4-methyl-7-(pivaloyloxy)isoxazolo[4,5-c]pyridine-6-carboxylate Ethyl 7-hydroxy-3-(4-methoxyphenyl)-4-methylisoxazolo[4,5-c]pyridine-6-carboxylate (56 mg, 0.17 mmol) and DMAP (1 mg) were added to pyridine (1 mL). Pivaloyl chloride (84 µl, 0.68 mmol) was added and the mixture was stirred at room temperature for 48 h. Saturated sodium bicarbonate solution (5 mL) and EtOAc (15 mL) were added, and the aqueous layer was extracted with additional EtOAc. The combined organic layer was dried over MgSO$_4$, concentrated, and the residue was purified by flash chromatography (0-20% EtOAc/hexanes) to give 58 mg of the title compound. MS: (+) m/z 413.50 (M+1).

b) Ethyl 4-(bromomethyl)-3-(4-methoxyphenyl)-7-(pivaloyloxy)isoxazolo[4,5-c]pyridine-6-carboxylate Ethyl 3-(4-methoxyphenyl)-4-methyl-7-(pivaloyloxy) isoxazolo[4,5-c]pyridine-6-carboxylate (58 mg, 0.14 mmol), NBS (28 mg, 0.15 mmol) and benzoyl peroxide (3.4 mg, 0.014 mmol) were added to 3 mL of carbon tetrachloride. The mixture was refluxed for 16 h. After the mixture was cooled to room temperature, another 1 equiv of NBS and 0.1 equiv of benzoyl peroxide were added, and the reaction mixture was refluxed for an additional 16 h. After the mixture was cooled, 20 mL of CH$_2$Cl$_2$ and 1 g of silica gel were added, and the solvent was removed in vacuo. The crude was purified by flash chromatography (0-30% EtOAc/hexanes) to give 34 mg of the title compound. MS: (+) m/z 491.28, 493.25 (M+1, $^{79}$Br/$^{81}$Br).

c) Ethyl 4-((1H-pyrazol-1-yl)methyl)-7-hydroxy-3-(4-methoxyphenyl)isoxazolo[4,5-c]pyridine-6-carboxylate Ethyl 4-(bromomethyl)-3-(4-methoxyphenyl)-7-(pivaloyloxy)isoxazolo[4,5-c]pyridine-6-carboxylate (34 mg, 0.069 mmol) and pyrazole (9.4 mg, 0.138 mmol) were added to 1 mL of toluene, and the mixture was stirred at room temperature for 48 h. An additional equiv. of pyrazole was added, and the mixture was stirred at room temperature for 16 h and then at 45° C. for 16 h. The mixture was diluted with EtOAc (20 mL) and washed with 1M hydrochloric acid. The organic layer was dried over MgSO$_4$ and concentrated, and the residue was purified by flash chromatography (0-100% EtOAc/hexanes) to give 19 mg of the title compound. MS: (+) m/z 395.29 (M+1).

d) {[7-Hydroxy-3-(4-methoxy-phenyl)-4-pyrazol-1-ylmethyl-isoxazolo[4,5-c]pyridine-6-carbonyl]-amino}-acetic acid Ethyl 4-((1H-pyrazol-1-yl)methyl)-7-hydroxy-3-(4-methoxyphenyl)isoxazolo[4,5-c]pyridine-6-carboxylate (19 mg, 0.048 mmol) and glycine (181 mg, 2.41 mmol) were added to sodium methoxide solution (3.6 mL, 1.81 mmol, 0.5 M in MeOH) and the mixture was refluxed for 3 days. The mixture was cooled to room temperature and the solvent was removed in vacuo. The residue was dissolved in 10 mL of water, and washed with EtOAc. The aqueous layer was acidified to pH 3 with 4M hydrochloric acid and extracted with EtOAc. The organic layer was dried over MgSO$_4$ and concentrated to give 14 mg of the title compound. MS: (+) m/z 424.31 (M+1).

Example 61

[(4-Acetyl-7-hydroxy-3-phenyl-isoxazolo[4,5-c]pyridine-6-carbonyl)-amino]-acetic acid 2-(4-ethynyl-7-hydroxy-3-phenylisoxazolo[4,5-c]pyridine-6-carboxamido)acetic acid (60 mg, 0.178 mmol) was dissolved in 6.6 mL of THF. Water (0.7 mL) was added, followed by 1.5 mL of a saturated solution of HgSO$_4$ in 1% H$_2$SO$_4$. The reaction mixture was stirred at room temperature for 16 h. Brine (10 mL) was added and the mixture was extracted with EtOAc. The combined organic layer was dried over MgSO$_4$ and concentrated to give a purple solid. The solid was taken up in 25 mL of saturated sodium bicarbonate solution and washed several times with EtOAc. The aqueous layer was acidified to pH 3 with 4M hydrochloric acid and extracted with EtOAc. The organic layer was dried over MgSO$_4$ and concentrated to give 65 mg of crude solid. The solid was purified by flash chromatography (0-100% EA/hexanes+2% acetic acid) to give 20 mg of the title compound. MS: (−) m/z 354.22 (M−1).

Example 62

[(4-Benzyl-7-hydroxy-3-phenyl-isoxazolo[4,5-c]pyridine-6-carbonyl)-amino]-acetic acid a) Ethyl 7-(anthracen-9-ylmethoxy)-4-iodo-3-phenylisoxazolo[4,5-c]pyridine-6-carboxylate Ethyl 7-hydroxy-4-iodo-3-phenylisoxazolo[4,5-c]pyridine-6-carboxylate (300 mg, 0.73 mmol), 9-chloromethylanthracene (249 mg, 1.10 mmol), 18-crown-6 (29 mg, 0.11 mmol) and K$_2$CO$_3$ (152 mg, 1.10 mmol) were added to DMF, and the mixture was stirred at 55° C. for 3 h. EtOAc (50 mL) was added and the organic layer was washed with brine and dried over MgSO$_4$. Solvent was removed in vacuo and the crude product was purified twice by flash chromatography (0-30% EtOAc/hexanes) to give 200 mg of the title compound. $^1$H NMR (CDCl$_3$, 200 MHz): δ=8.65-8.80 (m, 2H), 8.18 (s, 1H), 7.70-7.80 (m, 2H), 7.40-7.55 (m, 3H), 7.18-7.30 (m, 6H), 6.30 (s, 2H), 3.95 (q, 2H, J=7.0 Hz), 0.72 (t, 3H, J=7.2 Hz).

b) Ethyl 7-(anthracen-9-ylmethoxy)-4-benzyl-3-phenylisoxazolo[4,5-c]pyridine-6-carboxylate A flask was charged with ethyl 7-(anthracen-9-ylmethoxy)-4-iodo-3-phenylisoxazolo[4,5-c]pyridine-6-carboxylate (200 mg, 0.33 mmol), potassium benzyltrifluoroborate (80 mg, 0.4 mmol), PdCl$_2$(dppf) (27 mg, 0.033 mmol) and cesium carbonate (326 mg, 1.0 mmol). The flask was evacuated and refilled with nitrogen. THF (4 mL) and water (0.4 mL) were added and the mixture was refluxed for 16 h. The solvent was removed in vacuo and the residue was partitioned between EtOAc and 0.5M hydrochloric acid. The aqueous layer was extracted with additional EtOAc and the organic layer was dried over MgSO$_4$. After evaporation of solvent, the crude residue was purified by flash chromatography (0-30% EtOAc/hexanes) to give 110 mg of the title compound. MS: (+) m/z 565.38 (M+1).

c) Ethyl 4-benzyl-7-hydroxy-3-phenylisoxazolo[4,5-c]pyridine-6-carboxylate

Ethyl 7-(anthracen-9-ylmethoxy)-4-benzyl-3-phenylisoxazolo[4,5-c]pyridine-6-carboxylate (110 mg, 0.23 mmol) was dissolved in 2 mL of CH$_2$Cl$_2$ and cooled in an ice bath. Trifluoroacetic acid (0.18 mL, 2.30 mmol) was added and the mixture was stirred at 0° C. for 20 min. Solvent and excess TFA were evaporated off, and the residue was partitioned between 20 mL of EtOAc and 20 mL of saturated sodium bicarbonate solution. The pH of the mixture was adjusted to 3 by addition of 4M hydrochloric acid. The aqueous layer was extracted with additional EtOAc and the combined organic layer was dried over MgSO$_4$ and concentrated. Purification of the residue by flash chromatography (0-40% EtOAc/hexanes) gave 36 mg of the title compound. MS: (+) m/z 375.37 (M+1).

d) [(4-Benzyl-7-hydroxy-3-phenyl-isoxazolo[4,5-c]pyridine-6-carbonyl)-amino]-acetic acid Ethyl 4-benzyl-7-hydroxy-3-phenylisoxazolo[4,5-c]pyridine-6-carboxylate (36 mg, 0.096 mmol), glycine (145 mg, 1.93 mmol), sodium ethoxide (98 mg, 1.44 mmol) in 3 mL of DMF were refluxed for 2 h. After cooling to room temperature, water (15 mL) and EtOAc (20 mL) were added. The mixture was acidified to pH 2 by addition of 4M hydrochloric acid. The aqueous layer was extracted with additional EtOAc and the combined organic layer was dried over MgSO$_4$. After evaporation of solvent, the residue was redissolved in EtOAc and washed several times with water to remove residual DMF. Drying over MgSO$_4$ followed by evaporation afforded 28 mg of crude solid. The solid was dissolved in 50 mL of saturated sodium bicarbonate solution and washed with hexanes and EtOAc. The aqueous layer was acidified to pH 2 with 4M hydrochloric acid and extracted with EtOAc. The organic layer was dried over MgSO$_4$ and concentrated to give 26 mg of the title compound. MS: (+) m/z 404.33 (M+1).

Example 63

{[4-(1-Benzyl-1H-1,2,31-triazol-4-yl)-7-hydroxy-3-phenyl-isoxazolo[4,5-c]pyridine-6-carbonyl]-amino}-acetic acid a) Ethyl 4-ethynyl-7-hydroxy-3-phenylisoxazolo[4,5-c]pyridine-6-carboxylate Ethyl 7-hydroxy-3-phenyl-4-((trimethylsilyl)ethynyl)isoxazolo[4,5-c]pyridine-6-carboxylate (205 mg, 0.54 mmol) was dissolved in a 1:1 mixture of EtOH/CH$_2$Cl$_2$ (6 mL). Cesium carbonate (211 mg, 0.65 mmol) was added and the resulting slurry was stirred at room temperature for 14 h. The solvent was evaporated and the residue was partitioned between EtOAc (25 mL) and 1 M hydrochloric acid (25 mL). The aqueous layer was extracted with CH$_2$Cl$_2$ and the combined organic layer was dried over MgSO$_4$ and concentrated to give 185 mg of the title compound. MS: (+) m/z 309.29 (M+1).

b) Ethyl 4-(1-benzyl-1H-1,2,3-triazol-4-yl)-7-hydroxy-3-phenylisoxazolo[4,5-c]pyridine-6-carboxylate Ethyl 4-ethynyl-7-hydroxy-3-phenylisoxazolo[4,5-c]pyridine-6-carboxylate (185 mg, 0.60 mmol), benzyl azide (0.087 mL, 0.66 mmol), CuSO$_4$-5H$_2$O (7.5 mg, 0.03 mmol), and sodium ascorbate (18 mg, 0.09 mmol) were added to a mixture of CH$_2$Cl$_2$ (2 mL) and water (2 mL). The mixture was stirred at room temperature for 16 h. Another equiv. of benzyl azide was added, and the mixture was stirred for an additional 16 h. The mixture was diluted with CH$_2$Cl$_2$ (20 mL) and water (20 mL). The aqueous layer was extracted with additional CH$_2$Cl$_2$ and the combined organic layer was dried over MgSO$_4$ and concentrated. The crude product was purified twice by flash chromatography (first with 0-100% EtOAc/hexanes, then with 0-50% CH$_2$Cl$_2$/EtOAc) to afford 100 mg of the title compound. MS: (+) m/z 442.33 (M+1).

c) {[4-(1-Benzyl-1H-[1,2,3]-triazol-4-yl)-7-hydroxy-3-phenyl-isoxazolo[4,5-c]pyridine-6-carbonyl]-amino}-acetic acid Ethyl 4-(1-benzyl-1H-1,2,3-triazol-4-yl)-7-hydroxy-3-phenylisoxazolo[4,5-c]pyridine-6-carboxylate (100 mg, 0.227 mmol), glycine (340 mg, 4.54 mmol) and sodium ethoxide (231 mg, 3.40 mmol) were added to 8 mL of DMF and the mixture was refluxed for 2 h. After the mixture was cooled to room temperature, water (50 mL) and EtOAc (50 mL) were added. The biphasic mixture was acidified to pH 2 by addition of 4M hydrochloric acid. The aqueous layer was extracted with additional EtOAc and the combined organic layer was dried over MgSO$_4$ and concentrated to give an oily residue. The residue was dissolved in 300 mL of saturated sodium bicarbonate solution and washed with hexanes and EtOAc. The aqueous layer was acidified with concentrated hydrochloric acid to pH 2 and extracted with EtOAc. The solvent was concentrated in vacuo to give 91 mg of the title compound. MS: (+) m/z 471.29 (M+1).

Example 64

[(7-Hydroxy-3-phenyl-4-trifluoromethyl-isoxazolo[4,5-c]pyridine-6-carbonyl)-amino]-acetic acid a) Ethyl 7-hydroxy-3-phenyl-4-(trifluoromethyl)isoxazolo[4,5-c]pyridine-6-carboxylate A flask was charged with Cd powder (0.67 g, 5.93 mmol) and evacuated. After refilling with nitrogen, DMF (4 mL) was added and the suspension was cooled in an ice bath. Dibromodifluoromethane (0.3 mL, 3.29 mmol) was added dropwise and the resulting mixture was stirred at room temperature for 2 h. HMPA (4 mL) was added and the mixture was cooled in an ice bath. Copper bromide (0.28 g, 1.98 mmol) was added, and after the mixture was warmed to room temperature, ethyl 7-hydroxy-4-iodo-3-phenylisoxazolo[4,5-c]pyridine-6-carboxylate (270 mg, 0.66 mmol) was added as a neat solid. The mixture was stirred at 65° C. for 6 h. After the mixture was cooled to room temperature, 2M hydrochloric acid (50 mL) and EtOAc (50 mL) were added. The aqueous layer was extracted with CH$_2$Cl$_2$. The combined organic layer was washed with water and brine, and dried over MgSO$_4$. After solvent was removed, the crude product was purified by flash chromatography (0-100% EtOAc/hexanes) to give 58 mg of the title compound. MS: (+) m/z 353.27 (M+1).

b) [(7-Hydroxy-3-phenyl-4-trifluoromethyl-isoxazolo[4,5-c]pyridine-6-carbonyl)-amino]-acetic acid Ethyl 7-hydroxy-3-phenyl-4-(trifluoromethyl)isoxazolo[4,5-c]pyridine-6-carboxylate (58 mg, 0.17 mmol), glycine (247 mg, 3.30 mmol), and sodium ethoxide (168 mg, 2.47 mmol) were added to 6 mL of DMF and the mixture was refluxed for 2 h. After the mixture cooled to room temperature, water (50 mL) and EtOAc (50 mL) were added. The mixture was stirred vigorously and 4M hydrochloric acid was added until pH was 3. The aqueous layer was extracted with additional EtOAc and the combined organic layer was dried over MgSO$_4$ and concentrated. The residue was taken up in saturated sodium bicarbonate solution (20 mL) and washed with hexanes and EtOAc. The aqueous layer was acidified to pH 3 with 4M hydrochloric acid and extracted with EtOAc. The organic layer was dried over MgSO$_4$ and concentrated to give a crude solid, which was purified by flash chromatography (0-100% EtOAc/hexanes+2% acetic acid) to give 37 mg of the title compound. MS: (−) m/z 380.19 (M−1).

Example 65

[(3-Cyclohex-1-enyl-7-hydroxy-isoxazolo[4,5-c]pyridine-6-carbonyl)-amino]-acetic acid a) 4-Cyclohexyl-3-methyl-2,4-dioxo-butyric acid ethyl ester LHMDS solution (39.3 mL, 39.3 mmol, 1M in hexanes) was added to 200 mL of diethyl ether and the mixture was cooled to −78° C. Cyclohexyl ethyl ketone (5.0 g, 35.7 mmol) dissolved in 50 mL of ether was added dropwise, and the resulting mixture was stirred at −78° C. for 1 h. Diethyl oxalate (5.6 mL, 41.1 mmol) was then added dropwise, and the cooling bath was removed and the mixture was allowed to come to room temperature. After the mixture was stirred for 16 h, 1M hydrochloric acid (200 mL) was added and the organic layer was separated. The aqueous layer was extracted with CH$_2$Cl$_2$ (3×100 mL) and the combined organic layers were dried over MgSO$_4$ and concentrated. The crude oil was purified by chromatography (0-20% EtOAc/hexanes) to give 5.36 g of the title compound. MS: (−) m/z 239.33 (M−1).

b) 4-Cyclohexyl-4-hydroxyimino-3-methyl-2-oxo-butyric acid ethyl ester

Sodium hydroxide (0.99 g, 24.7 mmol) was dissolved in 5.5 mL of water. Hydroxylamine hydrochloride (1.71 g, 24.7 mmol) was added and the reaction mixture was stirred until complete dissolution was achieved. 4-Cyclohexyl-3-methyl-2,4-dioxo-butyric acid ethyl ester (5.15 g, 21.5 mmol) was added and the resulting mixture was stirred at ambient temperature for 16 h. Ethyl acetate (20 mL) and 1M hydrochloric acid (10 mL) was added, and the aqueous layer was extracted with additional ethyl acetate (4×20 mL). The organic layers were combined, dried over MgSO$_4$ and concentrated. The crude oil was purified by chromatography (0-30% EtOAc/hexanes) to give 3.1 g of the title compound. MS: (+) m/z 256.39 (M+1).

c) 3-Cyclohexyl-4-methyl-isoxazole-5-carboxylic acid ethyl ester

4-Cyclohexyl-4-hydroxyimino-3-methyl-2-oxo-butyric acid ethyl ester (3.1 g, 12.2 mmol) and concentrated sulfuric acid (3 mL) were added to 50 mL of absolute ethanol and the mixture was refluxed for 16 hours. After the mixture cooled to room temperature, saturated sodium bicarbonate solution was added to neutralize the mixture. The product was extracted with CH$_2$Cl$_2$ and the combined organic layer was dried over MgSO$_4$ and concentrated to give 2.64 g of the title compound. MS: (+) m/z 238.38 (M+1).

d) 3-(1-Bromo-cyclohexyl)-4-bromomethyl-isoxazole-5-carboxylic acid ethyl ester 3-Cyclohexyl-4-methyl-isoxazole-5-carboxylic acid ethyl ester (2.64 g, 11.1 mmol), NBS (1.98 g, 11.1 mmol), and benzoyl peroxide (0.27 g mg, 1.11 mmol) were added to 65 mL of carbon tetrachloride and the mixture was refluxed for 16 h. The mixture was cooled to room temperature and concentrated in vacuo. The crude product was purified by flash chromatography (0-15% EtOAc/hexanes) to give 0.92 g of the title compound. MS: (+) m/z 396.10 (M+1).

e) Ethyl 4-(((2,4-dimethoxybenzyl)(2-ethoxy-2-oxoethyl)amino)methyl)-3-(1-bromo-cyclohexyl)-isoxazole-5-carboxylate and ethyl 4-(((2,4-dimethoxybenzyl)(2-ethoxy-2-oxoethyl)amino)methyl)-3-(1-cyclohexenyl)-isoxazole-5-carboxylate 3-(1-Bromo-cyclohexyl)-4-bromomethyl-isoxazole-5-carboxylic acid ethyl ester (0.92 g, 2.33 mmol) was dissolved in 25 mL of acetonitrile. N-(2,4-dimethoxybenzyl)glycine ethyl ester (0.65 g, 2.56 mmol), potassium carbonate (0.97 g, 6.99 mmol) and potassium iodide (0.58 g, 3.49 mmol) were added, and the mixture was stirred at room temperature for 72 h. The solvent was removed in vacuo and the residue was partitioned between CH$_2$Cl$_2$ and water. The aqueous layer was extracted with additional CH$_2$Cl$_2$ and the combined organic layer was dried over MgSO$_4$ and concentrated. The crude oil was purified by flash chromatography (0-30% EtOAc/hexanes) to give 1.30 g of the title compounds as a mixture. MS (first compound): (+) m/z 567.42, 569.32 (M+1, $^{79}$Br/$^{81}$Br). MS (second compound): (+) m/z 487.67 (M+1).

f) 3-Cyclohex-1-enyl-7-hydroxy-isoxazolo[4,5-c]pyridine-6-carboxylic acid ethyl ester The above mixture of ethyl 4-(((2,4-dimethoxybenzyl)(2-ethoxy-2-oxoethyl)amino)-methyl)-3-(1-bromo-cyclohexyl)-isoxazole-5-carboxylate and ethyl 4-(((2,4-dimethoxybenzyl)(2-ethoxy-2-oxoethyl)amino)methyl)-3-(1-cyclohexenyl)-isoxazole-5-carboxylate was dissolved in 40 mL of THF and cooled to −78° C. Potassium tert-butoxide solution (6.9 mL, 6.9 mmol, 1M in THF) was added dropwise, and the mixture was stirred for 14 hours, the cold bath allowed to evaporate spontaneously. The reaction mixture was cooled in an ice bath and quenched with 20 mL of 1M HCl. The product was extracted with EtOAc and the organic layer was dried over MgSO$_4$ and concentrated to give 0.8 g of crude oil. The crude intermediate was dissolved in 12 mL of CH$_2$Cl$_2$.

Thionyl chloride (0.2 mL, 2.73 mmol) was added and the reaction mixture was stirred for 5 h at ambient temperature. The volatiles were evaporated and the residue was partitioned between CH$_2$Cl$_2$ (50 mL) and saturated sodium bicarbonate solution (50 mL). To the vigorously stirring biphasic mixture was added 4M hydrochloric acid until pH was 2. The aqueous layer was extracted with additional CH$_2$Cl$_2$ and the combined organic layer was dried over MgSO$_4$ and concentrated. The crude residue was purified by chromatography (0-100% CH$_2$Cl$_2$/hexanes) to give 210 mg of the title compound. MS: (+) m/z 289.30 (M+1).

g) [(3-Cyclohex-1-enyl-7-hydroxy-isoxazolo[4,5-c]pyridine-6-carbonyl)-amino]-acetic acid 3-Cyclohex-1-enyl-7-hydroxy-isoxazolo[4,5-c]pyridine-6-carboxylic acid ethyl ester (77 mg, 0.27 mmol) was dissolved in 10 mL of DMF. Glycine (0.40 g, 5.35 mmol) and sodium ethoxide (0.27 g, 4.01 mmol) were added and the mixture was refluxed for 2 h. The mixture was cooled to room temperature and diluted with 60 mL of water. EtOAc (50 mL) was added and the resulting biphasic mixture was stirred vigorously as 4M hydrochloric acid was added dropwise until pH was 3. The aqueous layer was extracted with additional EtOAc, and the combined organic layer was washed with water and dried over MgSO$_4$. The solvent was evaporated and the solid residue was taken up in 50 mL of saturated sodium bicarbonate solution. The aqueous phase was washed with hexanes and EtOAc. The aqueous layer was then acidified to pH 2 by addition of concentrated hydrochloric acid and the resulting precipitate was isolated by filtration to give 65 mg of the title compound. MS: (+) m/z 318.26 (M+1).

Example 66

[(3-Ethyl-7-hydroxy-isoxazolo[4,5-c]pyridine-6-carbonyl)-amino]-acetic acid a) 3-Methyl-2,4-dioxo-hexanoic acid ethyl ester

LHMDS solution (35.7 mL, 35.7 mmol, 1M in hexanes) was added to 200 mL of diethyl ether and the mixture was cooled to −78° C. 3-Pentanone (3.8 mL, 35.7 mmol) dissolved in 50 mL of ether was added dropwise, and the resulting mixture was stirred at −78° C. for 1 h. Diethyl oxalate (5.3 mL, 39.3 mmol) was added dropwise, and the cooling bath was removed and the mixture was allowed to come to room temperature. After the mixture was stirred for 16 h, the resulting precipitate was isolated by filtration. The solid was partitioned between CH$_2$Cl$_2$ (150 mL) and 1M hydrochloric acid (100 mL), and the aqueous layer was extracted with additional CH$_2$Cl$_2$. The combined organic layer was dried over MgSO$_4$ and concentrated to give 6.37 g of the title compound. MS: (−) m/z 185.28 (M−1).

b) 4-Hydroxyimino-3-methyl-2-oxo-hexanoic acid ethyl ester

Sodium hydroxide (1.58 g, 39.4 mmol) was dissolved in 8.5 mL of water. Hydroxylamine hydrochloride (2.74 g, 39.4 mmol) was added and the reaction mixture was stirred until complete dissolution was achieved. 3-Methyl-2,4-dioxo-hexanoic acid ethyl ester (6.37 g, 34.2 mmol) was added and the resulting mixture was stirred at ambient temperature for 16 h. The reaction mixture was extracted with EtOAc (3×50 mL) and the organic layers were combined, dried over MgSO$_4$ and concentrated. The crude oil was purified by chromatography (0-40% EtOAc/hexanes) to give 3.7 g of the title compound. MS: (+) m/z 202.35 (M+1).

c) 3-Ethyl-4-methyl-isoxazole-5-carboxylic acid ethyl ester

4-Hydroxyimino-3-methyl-2-oxo-hexanoic acid ethyl ester (3.7 g, 18.4 mmol) and concentrated sulfuric acid (3 mL) were added to 50 mL of absolute ethanol and the mixture was refluxed for 16 hours. After the mixture cooled to room temperature, saturated sodium bicarbonate solution was added to neutralize the mixture. The product was extracted with $CH_2Cl_2$ and the combined organic layer was dried over $MgSO_4$ and concentrated to give 3.3 g of the title compound. MS: (+) m/z 184.26 (M+1).

d) 4-Bromomethyl-3-ethyl-isoxazole-5-carboxylic acid ethyl ester

3-Ethyl-4-methyl-isoxazole-5-carboxylic acid ethyl ester (3.5 g, 19.1 mmol), NBS (3.4 g, 19.1 mmol), and benzoyl peroxide (0.46 g mg, 1.91 mmol) were added to 110 mL of carbon tetrachloride and the mixture was refluxed for 16 h. The mixture was cooled to room temperature and concentrated in vacuo. The crude product was purified by flash chromatography (0-10% EtOAc/hexanes) to give 1.03 g of the title compound. MS: (+) m/z 262.17, 264.14 (M+1, $^{79}$Br/$^{81}$Br).

e) Ethyl 4-(((2,4-dimethoxybenzyl)(2-ethoxy-2-oxo-ethyl)amino)methyl)-3-ethyl-isoxazole-5-carboxylate 4-Bromomethyl-3-ethyl-isoxazole-5-carboxylic acid ethyl ester (1.03 g, 3.93 mmol) was dissolved in 40 mL of acetonitrile. N-(2,4-dimethoxybenzyl)glycine ethyl ester (1.09 g, 4.32 mmol), potassium carbonate (1.63 g, 11.8 mmol) and potassium iodide (0.98 g, 5.90 mmol) were added, and the mixture was stirred at room temperature for 16 h. The solvent was removed in vacuo and the residue was partitioned between $CH_2Cl_2$ and water. The aqueous layer was extracted with additional $CH_2Cl_2$ and the combined organic layer was dried over $MgSO_4$ and concentrated. The crude oil was purified by flash chromatography (0-30% EtOAc/hexanes) to give 0.88 g of the title compound. MS: (+) m/z 435.53 (M+1).

f) 3-Ethyl-7-hydroxy-isoxazolo[4,5-c]pyridine-6-carboxylic acid ethyl ester

Ethyl 4-(((2,4-dimethoxybenzyl)(2-ethoxy-2-oxoethyl)amino)methyl)-3-ethyl-isoxazole-5-carboxylate (0.88 g, 2.03 mmol) was dissolved in 40 mL of THF and cooled to −78° C. Potassium tert-butoxide solution (4.1 mL, 4.1 mmol, 1M in THF) was added dropwise, and the mixture was stirred for 14 hours, the cold bath allowed to evaporate spontaneously. The reaction mixture was cooled in an ice bath and quenched with 50 mL of 1M HCl. The product was extracted with EtOAc and the organic layer was dried over $MgSO_4$ and concentrated to give 0.8 g of crude oil. The crude intermediate was dissolved in 12 mL of $CH_2Cl_2$. Thionyl chloride (0.23 mL, 3.09 mmol) was added and the reaction mixture was stirred for 5 h at ambient temperature. The volatiles were evaporated and the residue was partitioned between $CH_2Cl_2$ (50 mL) and saturated sodium bicarbonate solution (50 mL). To the vigorously stirring biphasic mixture was added 4M hydrochloric acid until pH was 2. The aqueous layer was extracted with additional $CH_2Cl_2$ and the combined organic layer was dried over $MgSO_4$ and concentrated. The crude residue was purified by chromatography (0-100% $CH_2Cl_2$/hexanes) to give 440 mg of the title compound. MS: (+) m/z 237.29 (M+1).

g) [(3-Ethyl-7-hydroxy-isoxazolo[4,5-c]pyridine-6-carbonyl)-amino]-acetic acid 3-Ethyl-7-hydroxy-isoxazolo[4,5-c]pyridine-6-carboxylic acid ethyl ester (80 mg, 0.42 mmol) was dissolved in 12 mL of DMF. Glycine (0.51 g, 6.78 mmol) and sodium ethoxide (0.35 g, 5.08 mmol) were added and the mixture was refluxed for 2 h. The mixture was cooled to room temperature and diluted with 60 mL of water. EtOAc (50 mL) was added and the resulting biphasic mixture was stirred vigorously as 4M hydrochloric acid was added dropwise until pH was 3. The aqueous layer was extracted with additional EtOAc, and the combined organic layer was washed with water and dried over $MgSO_4$. The solvent was evaporated and the solid residue was taken up in 50 mL of saturated sodium bicarbonate solution. The aqueous phase was washed with hexanes and EtOAc. The aqueous layer was then acidified to pH 2 by addition of concentrated hydrochloric acid and extracted with EtOAc (3×50 mL). The combined organic layer was dried over $MgSO_4$ and concentrated to give 56 mg of the title compound. MS: (+) m/z 266.32 (M+1).

Example 67

{[3-(3-Cyano-phenyl)-4-hydroxy-isoxazolo[5,4-c]pyridine-5-carbonyl]-amino}-acetic acid Prepared in analogy to Example 1 from 3-(3-cyano-phenyl)-4-hydroxy-isoxazolo[5,4-c]pyridine-5-carboxylic acid ethyl ester. The title compound, ESI MS (m/z): 339.20 (M+H$^+$); 337.30 (M−H$^+$).

Example 68

{[3-(4-Cyano-phenyl)-4-hydroxy-isoxazolo[5,4-c]pyridine-5-carbonyl]-amino}-acetic acid Prepared in analogy to Example 1 from 3-(4-cyano-phenyl)-4-hydroxy-isoxazolo[5,4-c]pyridine-5-carboxylic acid ethyl ester. The title compound, ESI MS (m/z): 339.27 (M+H$^+$); 337.30 (M−H$^+$).

Example 69

{[4-Hydroxy-3-(4-phenoxy-phenyl)-isoxazolo[5,4-c]pyridine-5-carbonyl]-amino}-acetic acid Prepared in analogy to Example 1 from 4-hydroxy-3-(4-phenoxy-phenyl)-isoxazolo[5,4-c]pyridine-5-carboxylic acid ethyl ester. The title compound, ESI MS (m/z): 406.30 (M+H$^+$); 404.33 (M−H$^+$).

Example 70

[(4-Hydroxy-3-methyl-isoxazolo[5,4-c]pyridine-5-carbonyl)-amino]-acetic acid a) 5-Bromomethyl-3-methyl-isoxazole-4-carboxylic acid ethyl ester

Prepared in analogy to Example 1 from 3,5-dimethyl-isoxazole-4-carboxylic acid ethyl ester. The title compound, $^1$H NMR (CDCl$_3$, 200 MHz): S=4.73 (s, 2H), 4.30 (m, H), 2.47 (s, 3H), 1.41 (m, 3H).

b) 5-{[(2,4-Dimethoxy-benzyl)-ethoxycarbonylmethyl-amino]-methyl}-3-methyl-isoxazole-4-carboxylic acid ethyl ester Prepared in analogy to Example 1 from 5-bromomethyl-3-methyl-isoxazole-4-carboxylic acid ethyl ester. The title compound, ESI MS (m/z): 421.39 (M+H$^+$).

c) 4-Hydroxy-3-methyl-isoxazolo[5,4-c]pyridine-5-carboxylic acid ethyl ester Prepared in analogy to Example 1 from 5-{[(2,4-dimethoxy-benzyl)-ethoxycarbonylmethyl-amino]-methyl}-3-methyl-isoxazole-4-carboxylic acid ethyl ester. The title compound, ESI MS (m/z): 223.16 (M+H$^+$); 221.13 (M−H$^+$).

d) [(Hydroxy-3-methyl-isoxazolo[5,4-c]pyridine-5-carbonyl)-amino]-acetic acid Prepared in analogy to Example 1 from 4-hydroxy-3-methyl-isoxazolo[5,4-c]pyridine-5-carboxylic acid ethyl ester. The title compound, ESI MS (m/z): 250.28 (M−H$^+$).

Example 71

[(4-Hydroxy-3-methyl-7-phenyl-isoxazolo[5,4-c]pyridine-5-carbonyl)-amino]-acetic acid a) 4-Hydroxy-7-iodo-3-methyl-isoxazolo[5,4-c]pyridine-5-carboxylic acid ethyl ester Prepared in analogy to Example 27(a) from 4-hydroxy-3-methyl-isoxazolo[5,4-c]pyridine-5-carboxylic acid ethyl ester. The title compound, ESI MS (m/z): 349.12 (M+H$^+$); 347.15 (M−H$^+$).

b) 4-Hydroxy-3-methyl-7-phenyl-isoxazolo[5,4-c]pyridine-5-carboxylic acid ethyl ester Prepared in analogy to Example 3 from 4-hydroxy-7-iodo-3-methyl-isoxazolo[5,4-c]pyridine-5-carboxylic acid ethyl ester. The title compound, ESI MS (m/z): 299.29 (M+H$^+$); 297.32 (M−H$^+$).

c) [(4-Hydroxy-3-methyl-7-phenyl-isoxazolo[5,4-c]pyridine-5-carbonyl)-amino]-acetic acid Prepared in analogy to Example 1 from 4-hydroxy-3-methyl-7-phenyl-isoxazolo[5,4-c]pyridine-5-carboxylic acid ethyl ester. The title compound, ESI MS (m/z): 328.25 (M+H$^+$); 326.28 (M−H$^+$).

Example 72

[(4-Hydroxy-3,7-dimethyl-isoxazolo[5,4-c]pyridine-5-carbonyl)-amino]-acetic acid a) 4-Hydroxy-3,7-dimethyl-isoxazolo[5,4-c]pyridine-5-carboxylic acid ethyl ester Prepared in analogy to Example 2 from 4-hydroxy-7-iodo-3-methyl-isoxazolo[5,4-c]pyridine-5-carboxylic acid ethyl ester. The title compound, ESI MS (m/z): 237.29 (M+H$^+$); 235.25 (M−H$^+$).

b) [(4-Hydroxy-3,7-dimethyl-isoxazolo[5,4-c]pyridine-5-carbonyl)-amino]-acetic acid Prepared in analogy to Example 1 from 4-hydroxy-3,7-dimethyl-isoxazolo[5,4-c]pyridine-5-carboxylic acid ethyl ester. The title compound, ESI MS (m/z): 266.25 (M+H$^+$); 264.28 (M−H$^+$).

Example 73

{[4-Hydroxy-7-methyl-3-(4-trifluoromethoxy-phenyl)-isoxazolo[5,4-c]pyridine-5-carbonyl]-amino}-acetic acid a) 7-Bromo-4-hydroxy-3-(4-trifluoromethoxy-phenyl)-isoxazolo[5,4-c]pyridine-5-carboxylic acid ethyl ester A mixture of 4-hydroxy-3-(4-trifluoromethoxy-phenyl)-isoxazolo[5,4-c]pyridine-5-carboxylic acid ethyl ester (508 mg, 1.38 mmole) and bis(2,4,6-trimethylpyridine)bromide(I) hexafluorophosphate (964 mg, 2.07 mmole) in dichloromethane (9 ml) was stirred at room temperature for 17 h before it was concentrated and purified by flash column chromatography on silica gel with a gradient of dichloromethane and hexanes to give the title compound as a white solid (271 mg): ESI MS (m/z): 447.22, 448.06 (M+H$^+$, $^{79}$Br/$^{81}$Br), 445.19, 447.16 (M−H$^+$, $^{79}$Br/$^{81}$Br).

b) 4-Hydroxy-7-methyl-3-(4-trifluoromethoxy-phenyl)-isoxazolo[5,4-c]pyridine-5-carboxylic acid ethyl ester Prepared in analogy to Example 2 from 7-bromo-4-hydroxy-3-(4-trifluoromethoxy-phenyl)-isoxazolo[5,4-c]pyridine-5-carboxylic acid ethyl ester. The title compound, ESI MS (m/z): 383.25 (M+H$^+$); 381.28 (M−H$^+$).

c) {[4-Hydroxy-7-methyl-3-(4-trifluoromethoxy-phenyl)-isoxazolo[5,4-c]pyridine-5-carbonyl]-amino}-acetic acid Prepared in analogy to Example 1 from 4-hydroxy-7-methyl-3-(4-trifluoromethoxy-phenyl)-isoxazolo[5,4-c]pyridine-5-carboxylic acid ethyl ester. The title compound, ESI MS (m/z): 412.21 (M+H$^+$); 410.24 (M−H$^+$).

Example 74

{[4-Hydroxy-3-(4-methoxy-phenyl)-7-methyl-isoxazolo[5,4-c]pyridine-5-carbonyl]-amino}-acetic acid a) 7-Bromo-4-hydroxy-3-(4-methoxy-phenyl)-isoxazolo[5,4-c]pyridine-5-carboxylic acid ethyl ester Prepared in analogy to Example 2 from 4-hydroxy-3-(4-methoxy-phenyl)-isoxazolo[5,4-c]pyridine-5-carboxylic acid ethyl ester. The title compound ESI MS (m/z): 393.18, 395.18 (M+H⁺, ⁷⁹Br/⁸¹Br), 391.21, 393.25 (M−H⁺, ⁷⁹Br/⁸¹Br).

b) 4-Hydroxy-3-(4-methoxy-phenyl)-7-methyl-isoxazolo[5,4-c]pyridine-5-carboxylic acid ethyl ester Prepared in analogy to Example 2 from 7-bromo-4-hydroxy-3-(4-methoxy-phenyl)-isoxazolo[5,4-c]pyridine-5-carboxylic acid ethyl ester. The title compound, ESI MS (m/z): 329.27 (M+H⁺); 327.30 (M−H⁺).

c) {[4-Hydroxy-3-(4-methoxy-phenyl)-7-methyl-isoxazolo[5,4-c]pyridine-5-carbonyl]-amino}-acetic acid Prepared in analogy to Example 1 from 4-hydroxy-3-(4-methoxy-phenyl)-7-methyl-isoxazolo[5,4-c]pyridine-5-carboxylic acid ethyl ester. The title compound, ESI MS (m/z): 358.30 (M+H⁺); 356.33 (M−H⁺).

Example 75

{[3-(2,4-Dichloro-phenyl)-4-hydroxy-isoxazolo[5,4-c]pyridine-5-carbonyl]-amino}-acetic acid Prepared in analogy Example 1 from 3-(2,4-dichloro-phenyl)-4-hydroxy-isoxazolo[5,4-c]pyridine-5-carboxylic acid ethyl ester. The title compound, ESI MS (m/z): 382.23 (M+H⁺); 380.19 (M−H⁺).

Example 76

{[4-Hydroxy-3-(4-methanesulfonyl-phenyl)-isoxazolo[5,4-c]pyridine-5-carbonyl]-amino}-acetic acid Prepared in analogy to Example 1 from 4-hydroxy-3-(4-methanesulfonyl-phenyl)-isoxazolo[5,4-c]pyridine-5-carboxylic acid ethyl ester. The title compound, ESI MS (m/z): 392.29 (M+H⁺); 390.25 (M−H⁺).

We claim:
1. A compound of Formula I:

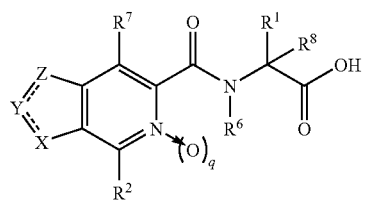

I wherein
q is 0 or 1;
X and Z are independently selected from the group consisting of —O—, =N—, and =C(R³)—;
Y is =C(R⁵)— or =N—, with the proviso that at least one of the following is present
a) one of X or Z is —O— and the other is =N—, and Y is =C(R⁵)—; or
b) one of X or Z is —O— and the other is =C(R³)—, and Y is =N—;

R¹ is selected from the group consisting of hydrogen, deuterium, alkyl, and substituted alkyl;

R² is selected from the group consisting of hydrogen, halo, cyano, nitro, alkyl, substituted alkyl, alkenyl, substituted alkenyl, alkynyl, substituted alkynyl, alkoxy, substituted alkoxy, cycloalkyl, substituted cycloalkyl, cycloalkoxy, substituted cycloalkoxy, amino, substituted amino, aminoacyl, acylamino, aryl, substituted aryl, aryloxy, substituted aryloxy, heteroaryl, substituted heteroaryl, heteroaryloxy, substituted heteroaryloxy, heterocyclyl, substituted heterocyclyl, heterocyclyloxy, substituted heterocyclyloxy, alkylthio, substituted alkylthio, cycloalkylthio, substituted cycloalkylthio, arylthio, substituted arylthio, heteroarylthio, substituted heteroarylthio, heterocyclicthio, substituted heterocyclicthio, and acyl;

R³ and R⁵ are independently selected from the group consisting of hydrogen, hydroxy, cyano, halo, nitro, acyl, amino, substituted amino, acylamino, sulfonyl, substituted sulfonyl, alkyl, substituted alkyl, alkenyl, substituted alkenyl, alkynyl, substituted alkynyl, cycloalkyl, substituted cycloalkyl, cycloalkoxy, substituted cycloalkoxy, alkoxy, substituted alkoxy, aryl, substituted aryl, aryloxy, substituted aryloxy, alkylthio, substituted alkylthio, cycloalkylthio, substituted cycloalkylthio, arylthio, substituted arylthio, heteroarylthio, substituted heteroarylthio, heterocyclicthio, substituted heterocyclicthio, heterocyclic, substituted heterocyclic, heterocyclyloxy, substituted heterocyclyloxy, heteroaryl, substituted heteroaryl, heteroaryloxy, and substituted heteroaryloxy;

R⁶ is selected from the group consisting of hydrogen, alkyl, and substituted alkyl;

R⁷ is selected from the group consisting of hydroxy, alkoxy, substituted alkoxy, cycloalkoxy, substituted cycloalkoxy, aryloxy, substituted aryloxy, heteroaryloxy, substituted heteroaryloxy, heterocyclyloxy, substituted heterocyclyloxy, mercapto, alkylthio, substituted alkylthio, cycloalkylthio, substituted cycloalkylthio, arylthio, substituted arylthio, heteroarylthio, substituted heteroarylthio, heterocyclicthio, substituted heterocyclicthio, amino, substituted amino, and acylamino; and R⁸ is selected from the group consisting of hydrogen, deuterium, and methyl;

or a pharmaceutically acceptable salt, single stereoisomer, mixture of stereoisomers, ester, or prodrug thereof.

2. The compound of claim 1, wherein q is 0.
3. The compound of claim 1, wherein R¹ is hydrogen or alkyl; R⁶ and R⁸ are hydrogen; and R⁷ is hydroxy.
4. The compound of claim 1, wherein R² is selected from the group consisting of hydrogen, cyano, halo, amino, substituted amino, alkyl, substituted alkyl, alkynyl, substituted alkynyl, cycloalkyl, aryl, substituted aryl, heteroaryl, substituted heteroaryl, and acyl.
5. The compound of claim 1, wherein R³ is selected from the group consisting of alkyl, substituted alkyl, substituted alkoxy, cycloalkyl, substituted cycloalkyl, aryl, substituted aryl, heteroaryl, and substituted heteroaryl.
6. The compound of claim 1, wherein R⁵ is selected from the group consisting of aryl, and substituted aryl.

7. The compound of claim 1, wherein the compound is of Formula I(a) or I(a)'

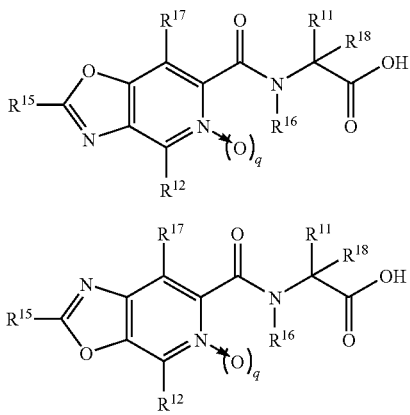

wherein
q is 0 or 1;
$R^{11}$ is selected from the group consisting of hydrogen, deuterium, alkyl, and substituted alkyl;
$R^{12}$ is selected from the group consisting of hydrogen, halo, cyano, nitro, alkyl, substituted alkyl, alkenyl, substituted alkenyl, alkynyl, substituted alkynyl, alkoxy, substituted alkoxy, cycloalkyl, substituted cycloalkyl, cycloalkoxy, substituted cycloalkoxy, amino, substituted amino, aminoacyl, acylamino, aryl, substituted aryl, aryloxy, substituted aryloxy, heteroaryl, substituted heteroaryl, heteroaryloxy, substituted heteroaryloxy, heterocyclyl, substituted heterocyclyl, heterocyclyloxy, substituted heterocyclyloxy, alkylthio, substituted alkylthio, cycloalkylthio, substituted cycloalkylthio, arylthio, substituted arylthio, heteroarylthio, substituted heteroarylthio, heterocyclicthio, substituted heterocyclicthio, and acyl;
$R^{15}$ is selected from the group consisting of hydrogen, hydroxy, cyano, halo, nitro, acyl, amino, substituted amino, acylamino, sulfonyl, substituted sulfonyl, alkyl, substituted alkyl, alkenyl, substituted alkenyl, alkynyl, substituted alkynyl, cycloalkyl, substituted cycloalkyl, cycloalkoxy, substituted cycloalkoxy, alkoxy, substituted alkoxy, aryl, substituted aryl, aryloxy, substituted aryloxy, alkylthio, substituted alkylthio, cycloalkylthio, substituted cycloalkylthio, arylthio, substituted arylthio, heteroarylthio, substituted heteroarylthio, heterocyclicthio, substituted heterocyclicthio, heterocyclycoxy, substituted heterocyclicoxy, heterocyclic, substituted heterocyclic, heteroaryl, substituted heteroaryl, heteroaryloxy, and substituted heteroaryloxy;
$R^{16}$ is selected from the group consisting of hydrogen, alkyl, and substituted alkyl;
$R^{17}$ is selected from the group consisting of hydroxy, alkoxy, substituted alkoxy, cycloalkoxy, substituted cycloalkoxy, aryloxy, substituted aryloxy, heteroaryloxy, substituted heteroaryloxy, heterocyclyloxy, substituted heterocyclyloxy, mercapto, alkylthio, substituted alkylthio, cycloalkylthio, substituted cycloalkylthio, arylthio, substituted arylthio, heteroarylthio, substituted heteroarylthio, heterocyclicthio, substituted heterocyclicthio, amino, substituted amino, and acylamino; and
$R^{18}$ is selected from the group consisting of hydrogen, deuterium, and methyl;

or a pharmaceutically acceptable salt, single stereoisomer, mixture of stereoisomers, ester, or prodrug thereof.

8. The compound of claim 7, wherein $R^{11}$, $R^{16}$ and $R^{18}$ are hydrogen; and $R^{17}$ is hydroxy.

9. The compound of claim 7, wherein $R^{12}$ is selected from the group consisting of hydrogen, alkyl, alkynyl, substituted alkynyl, aryl, and substituted aryl.

10. The compound of claim 7, wherein $R^{15}$ is aryl or substituted aryl.

11. The compound of claim 7, wherein
$R^{11}$, $R^{16}$, and $R^{18}$ are hydrogen;
$R^{12}$ is selected from the group consisting of hydrogen, alkyl, alkynyl, substituted alkynyl, aryl, and substituted aryl;
$R^{15}$ is selected from the group consisting of aryl and substituted aryl; and
$R^{17}$ is hydroxy.

12. The compound of claim 7, wherein
$R^{11}$, $R^{16}$, and $R^{18}$ are hydrogen;
$R^{12}$ is selected from the group consisting of hydrogen, methyl, ethyl, butyl, phenylethynyl, phenyl, 4-fluorophenyl, and 3-methoxyphenyl;
$R^{15}$ is phenyl or 4-fluorophenyl; and
$R^{17}$ is hydroxy.

13. The compound of claim 1, wherein the compound is of Formula I(b) or I(b)'

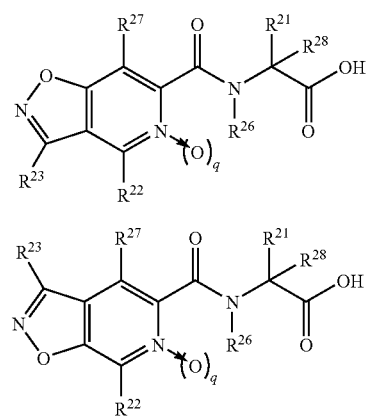

wherein
q is 0 or 1;
$R^{21}$ is selected from the group consisting of hydrogen, deuterium, alkyl, and substituted alkyl;
$R^{22}$ is selected from the group consisting of hydrogen, halo, cyano, nitro, alkyl, substituted alkyl, alkenyl, substituted alkenyl, alkynyl, substituted alkynyl, alkoxy, substituted alkoxy, cycloalkyl, substituted cycloalkyl, cycloalkoxy, substituted cycloalkoxy, amino, substituted amino, aminoacyl, acylamino, aryl, substituted aryl, aryloxy, substituted aryloxy, heteroaryl, substituted heteroaryl, heteroaryloxy, substituted heteroaryloxy, heterocyclyl, substituted heterocyclyl, heterocyclyloxy, substituted heterocyclyloxy, alkylthio, substituted alkylthio, cycloalkylthio, substituted cycloalkylthio, arylthio, substituted arylthio, heteroarylthio, substituted heteroarylthio, heterocyclicthio, substituted heterocyclicthio, and acyl;
$R^{23}$ is selected from the group consisting of hydrogen, hydroxy, cyano, halo, nitro, acyl, amino, substituted amino, acylamino, sulfonyl, substituted sulfonyl, alkyl, substituted alkyl, alkenyl, substituted alkenyl, alkynyl, substituted alkynyl, cycloalkyl, substituted cycloalkyl, cycloalkoxy, substituted cycloalkoxy, alkoxy, substituted alkoxy, aryl, substituted aryl, aryloxy, substituted aryloxy, alkylthio, substituted alkylthio, cycloalkylthio, substituted cycloalkylthio, arylthio, substituted arylthio, heteroarylthio, substituted heteroarylthio, heterocyclicthio, substituted heterocyclicthio, heterocyclicoxy, substituted heterocyclicoxy, heterocyclic, substituted heterocyclic, heteroaryl, substituted heteroaryl, heteroaryloxy, and substituted heteroaryloxy;

$R^{26}$ is selected from the group consisting of hydrogen, alkyl, and substituted alkyl;

$R^{27}$ is selected from the group consisting of hydroxy, alkoxy, substituted alkoxy, cycloalkoxy, substituted cycloalkoxy, aryloxy, substituted aryloxy, heteroaryloxy, substituted heteroaryloxy, heterocyclyloxy, substituted heterocyclyloxy, mercapto, alkylthio, substituted alkylthio, cycloalkylthio, substituted cycloalkylthio, arylthio, substituted arylthio, heteroarylthio, substituted heteroarylthio, heterocyclicthio, substituted heterocyclicthio, amino, substituted amino, and acylamino; and $R^{28}$ is selected from the group consisting of hydrogen, deuterium, and methyl;

or a pharmaceutically acceptable salt, single stereoisomer, mixture of stereoisomers, ester, or prodrug thereof.

14. The compound of claim 13, wherein $R^{21}$ is hydrogen or alkyl; $R^{26}$ and $R^{28}$ are hydrogen; and $R^{27}$ is hydroxyl.

15. The compound of claim 13, wherein $R^{22}$ is selected from the group consisting of hydrogen, cyano, halo, amino, substituted amino, alkyl, substituted alkyl, alkynyl, substituted alkynyl, cycloalkyl, aryl, heteroaryl, substituted heteroaryl, and acyl.

16. The compound of any of claim 13, wherein $R^{23}$ is alkyl, substituted alkyl, cycloalkyl, substituted cycloalkyl, aryl, substituted aryl, heteroaryl, or substituted heteroaryl.

17. The compound of claim 13, wherein $R^{21}$ is hydrogen or alkyl;

$R^{22}$ is selected from the group consisting of hydrogen, cyano, halo, amino, substituted amino, alkyl, substituted alkyl, alkynyl, substituted alkynyl, cycloalkyl, aryl, heteroaryl, substituted heteroaryl, and acyl;

$R^{23}$ is alkyl, substituted alkyl, cycloalkyl, substituted cycloalkyl, aryl, substituted aryl, heteroaryl, or substituted heteroaryl;

$R^{26}$ and $R^{28}$ are hydrogen; and $R^{27}$ is hydroxy.

18. The compound of claim 13, wherein $R^{21}$ is hydrogen or methyl;

$R^{22}$ is selected from the group consisting of hydrogen, cyano, bromo, (ethanic acid-2-yl)amino, methyl, trifluoromethyl, pyrazol-1-ylmethyl, cyclopropyl, benzyl, ethynyl, phenylethynyl, phenyl, pyridin-2-yl, pyridin-3-yl, pyridin-4-yl, 1-benzyl-1H-[1,2,3]triazol-4-yl, and acetyl;

$R^{23}$ is selected from the group consisting of methyl, ethyl, cyclohex-1-enyl, phenyl, 4-t-butylphenyl, 4-trifluoromethylphenyl, 2-trifluoromethoxyphenyl, 4-trifluoromethoxyphenyl, 2-chlorophenyl, 3-chlorophenyl, 4-chlorophenyl, 2-chloro-6-fluorophenyl, 4-fluorophenyl, 2,4-dichlorophenyl, 4-methoxyphenyl, 3-cyanophenyl, 4-cyanophenyl, 4-phenoxyphenyl, 4-methanesulfonylphenyl, biphenyl-4-yl, 3-trifluoromethoxyphenyl, thiophen-2-yl, 5-bromo-furan-2-yl, and pyridine-4-yl;

$R^{26}$ and $R^{28}$ are hydrogen; and $R^{27}$ is hydroxy.

19. A compound selected from the group consisting of [7-hydroxy-2-phenyl-oxazolo[4,5-c]pyridine-6-carbonyl)-amino]-acetic acid, {[2-(4-fluoro-phenyl)-7-hydroxy-oxazolo[4,5-c]pyridine-6-carbonyl]-amino}-acetic acid, [(7-hydroxy-4-methyl-2-phenyl-oxazolo[4,5-c]pyridine-6-carbonyl)-amino]-acetic acid, [(4-ethyl-7-hydroxy-2-phenyl-oxazolo[4,5-c]pyridine-6-carbonyl)-amino]-acetic acid, [(7-hydroxy-2,4-diphenyl-oxazolo[4,5-c]pyridine-6-carbonyl)-amino]-acetic acid, [(7-hydroxy-2-phenyl-4-phenylethynyl-oxazolo[4,5-c]pyridine-6-carbonyl)-amino]-acetic acid, [(4-butyl-7-hydroxy-2-phenyl-oxazolo[4,5-c]pyridine-6-carbonyl)-amino]-acetic acid, {[4-(4-fluoro-phenyl)-7-hydroxy-2-phenyl-oxazolo[4,5-c]pyridine-6-carbonyl]-amino}-acetic acid, [(7-hydroxy-2-phenyl-oxazolo[5,4-c]pyridine-6-carbonyl)-amino]-acetic acid, {[7-hydroxy-4-(3-methoxy-phenyl)-2-phenyl-oxazolo[4,5-c]pyridine-6-carbonyl]amino}-acetic acid, [(4-Hydroxy-3-phenyl-isoxazolo[5,4-c]pyridine-5-carbonyl)-amino]-acetic acid, [(4-hydroxy-7-methyl-3-phenyl-isoxazolo[5,4-c]pyridine-5-carbonyl)-amino]-acetic acid, [(4-hydroxy-3,7-diphenyl-isoxazolo[5,4-c]pyridine-5-carbonyl)-amino]-acetic acid, {[3-(4-chloro-phenyl)-4-hydroxy-isoxazolo[5,4-c]pyridine-5-carbonyl]-amino}-acetic acid, {[3-(2-chloro-phenyl)-4-hydroxy-isoxazolo[5,4-c]pyridine-5-carbonyl]-amino}-acetic acid, {[4-hydroxy-3-(4-methoxy-phenyl)-isoxazolo[5,4-c]pyridine-5-carbonyl]-amino}-acetic acid, {[3-(3-chloro-phenyl)-4-hydroxy-isoxazolo[5,4-c]pyridine-5-carbonyl]-amino}-acetic acid, {[3-(2-chloro-6-fluoro-phenyl)-4-hydroxy-isoxazolo[5,4-c]pyridine-5-carbonyl]-amino}-acetic acid, {[3-(4-fluoro-phenyl)-4-hydroxy-isoxazolo[5,4-c]pyridine-5-carbonyl]-amino}-acetic acid, [(7-cyano-4-hydroxy-3-phenyl-isoxazolo[5,4-c]pyridine-5-carbonyl)-amino]-acetic acid, {[3-(4-chloro-phenyl)-4-hydroxy-7-methyl-isoxazolo[5,4-c]pyridine-5-carbonyl]-amino}-acetic acid, {[7-bromo-3-(4-fluoro-phenyl)-4-hydroxy-isoxazolo[5,4-c]pyridine-5-carbonyl]-amino}-acetic acid, {[7-cyano-3-(4-fluoro-phenyl)-4-hydroxy-isoxazolo[5,4-c]pyridine-5-carbonyl]-amino}-acetic acid, {[7-bromo-3-(4-chloro-phenyl)-4-hydroxy-isoxazolo[5,4-c]pyridine-5-carbonyl]-amino}-acetic acid, {[3-(4-chloro-phenyl)-7-cyano-4-hydroxy-isoxazolo[5,4-c]pyridine-5-carbonyl]-amino}-acetic acid, {[3-(4-fluoro-phenyl)-4-hydroxy-7-methyl-isoxazolo[5,4-c]pyridine-5-carbonyl]-amino}-acetic acid, {[3-(3-chloro-phenyl)-7-(ethanic acid-2-yl)amino-4-hydroxy-isoxazolo[5,4-c]pyridine-5-carbonyl]-amino}-acetic acid, {[3-(4-chloro-phenyl)-7-ethynyl-4-hydroxy-isoxazolo[5,4-c]pyridine-5-carbonyl]-amino}-acetic acid, [(3-biphenyl-4-yl-4-hydroxy-isoxazolo[5,4-c]pyridine-5-carbonyl)-amino]-acetic acid, (S)-2-[(4-hydroxy-3-phenyl-isoxazolo[5,4-c]pyridine-5-carbonyl)-amino]-propionic acid, (R)-2-[(4-hydroxy-3-phenyl-isoxazolo[5,4-c]pyridine-5-carbonyl)-amino]-propionic acid, {[4-hydroxy-3-(3-trifluoromethoxy-phenyl)-isoxazolo[5,4-c]pyridine-5-carbonyl]-amino}-acetic acid, [(4-hydroxy-3-phenyl-7-pyridin-3-yl-isoxazolo[5,4-c]pyridine-5-carbonyl]-amino acetic acid, {[4-hydroxy-3-(4-trifluoromethyl-phenyl)-isoxazolo[5,4-c]pyridine-5-carbonyl]-amino}-acetic acid, {[4-hydroxy-3-(2-trifluoromethoxy-phenyl)-isoxazolo[5,4-c]pyridine-5-carbonyl]-amino}-acetic acid, [(4-hydroxy-3-phenyl-7-pyridin-4-yl-isoxazolo[5,4-c]pyridine-5-carbonyl)-amino]-acetic acid, [(4-hydroxy-3-phenyl-7-pyridin-2-yl-isoxazolo[5,4-c]pyridine-5-carbonyl)-amino]-acetic acid, [(4-hydroxy-3-phenyl-7-trifluoromethyl-isoxazolo[5,4-c]pyridine-5-carbonyl)-amino]-acetic acid, {[4-hydroxy-3-(4-trifluoromethoxy-phenyl)-isoxazolo[5,4-c]pyridine-5-carbonyl]-amino}-acetic acid, {[3-(4-tert-butyl-phenyl)-4-hydroxy-isoxazolo[5,4-c]pyridine-5-carbonyl]amino}-acetic acid, [(7-bromo-4-hydroxy-3-phenyl-isoxazolo[5,4-c]pyridine-5-carbonyl)-amino]-acetic acid, [(7-hydroxy-3-phenyl-isoxazolo[4,5-c]pyridine-6-carbonyl)-amino]-acetic acid, (S)-2-[(7-hydroxy-3-phenyl-isoxazolo[4,5-c]pyridine-6-carbonyl)-amino]-propionic acid, (R)-2-[(7-hydroxy-3-phenyl-isoxazolo[4,5-c]pyridine-6-carbonyl)-amino]-propionic acid, {[3-(4-fluoro-phenyl)-7-hydroxy-isoxazolo[4,5-c]pyridine-6-carbonyl]-amino}-acetic acid, {[7-hydroxy-3-(4-methoxy-phenyl)-isoxazolo[4,5-c]pyridine-6-carbonyl]-amino}-acetic acid, [(7-hydroxy-3-thiophen-2-yl-isoxazolo[4,5-c]pyridine-6-carbonyl)-amino]-acetic acid, [(7-hydroxy-3-pyridin-4-yl-isoxazolo[4,5-c]pyridine-6-carbonyl)-amino]-acetic acid, {[3-(5-bromo-furan-2-yl)-7-hydroxy-isoxazolo[4,5-c]pyridine-6-carbonyl]-amino}-acetic acid, [(7-hydroxy-4-methyl-3-phenyl-isoxazolo[4,5-c]pyridine-6-carbonyl)-amino]-acetic acid, [(4-cyano-7-hydroxy-3-thiophen-2-yl-isoxazolo[4,5-c]pyridine-6-carbonyl)-amino]-acetic acid, {[4-cyano-3-(4-fluoro-phenyl)-7-hydroxy-isoxazolo[4,5-c]pyridine-6-carbonyl]amino}-acetic acid, {[4-cyano-7-hydroxy-3-(4-methoxy-phenyl)-isoxazolo[4,5-c]pyridine-6-carbonyl]-amino}-acetic acid, {[3-(5-bromo-furan-2-yl)-4-cyano-7-hydroxy-isoxazolo[4,5-c]pyridine-6-carbonyl]-amino}-acetic acid, {[7-hydroxy-3-(4-methoxy-phenyl)-4-phenyl-isoxazolo[4,5-c]pyridine-6-carbonyl]-amino}-acetic acid, {[7-hydroxy-3-(4-methoxy-phenyl)-4-methyl-isoxazolo[4,5-c]pyridine-6-carbonyl]-amino}-acetic acid, [(7-hydroxy-3-phenyl-4-phenylethynyl-isoxazolo[4,5-c]pyridine-6-carbonyl)-amino]-acetic acid, [(4-ethynyl-7-hydroxy-3-phenyl-isoxazolo[4,5-c]pyridine-6-carbonyl)-amino]-acetic acid, [(4-cyclopropyl-7-hydroxy-3-thiophen-2-yl-isoxazolo[4,5-c]pyridine-6-carbonyl)-amino]acetic acid, {[7-hydroxy-3-(4-methoxy-phenyl)-4-pyrazol-1-ylmethyl-isoxazolo[4,5-c]pyridine-6-carbonyl]-amino}-acetic acid, [(4-acetyl-7-hydroxy-3-phenyl-isoxazolo[4,5-c]pyridine-6-carbonyl)-amino]-acetic acid, [(4-benzyl-7-hydroxy-3-phenyl-isoxazolo[4,5-c]pyridine-6-carbonyl)-amino]-acetic acid, {[4-(1-benzyl-1H-[1,2,3]triazol-4-yl)-7-hydroxy-3-phenyl-isoxazolo[4,5-c]pyridine-6-carbonyl]-amino}-acetic acid, [(7-hydroxy-3-phenyl-4-trifluoromethyl-isoxazolo[4,5-c]pyridine-6-carbonyl)-amino]-acetic acid, [(3-cyclohex-1-enyl-7-hydroxy-isoxazolo[4,5-c]pyridine-6-carbonyl)-amino]-acetic acid, [(3-ethyl-7-hydroxy-isoxazolo[4,5-c]pyridine-6-carbonyl)-amino]-acetic acid, {[3-(3-Cyano-phenyl)-4-hydroxy-isoxazolo[5,4-c]pyridine-5-carbonyl]-amino}-acetic acid, {[3-(4-Cyano-phenyl)-4-hydroxy-isoxazolo[5,4-c]pyridine-5-carbonyl]-amino}-acetic acid, {[4-Hydroxy-3-(4-phenoxy-phenyl)-isoxazolo[5,4-c]pyridine-5-carbonyl]amino}-acetic acid, [(4-Hydroxy-3-methyl-isoxazolo[5,4-c]pyridine-5-carbonyl)-amino]-acetic acid, [(4-Hydroxy-3-methyl-7-phenyl-isoxazolo[5,4-c]pyridine-5-carbonyl)-amino]-acetic acid, [(4-Hydroxy-3,7-dimethyl-isoxazolo[5,4-c]pyridine-5-carbonyl)-amino]-acetic acid, {[4-Hydroxy-7-methyl-3-(4-trifluoromethoxy-phenyl)-isoxazolo[5,4-c]pyridine-5-carbonyl]-amino}-acetic acid, {[4-Hydroxy-3-(4-methoxy-phenyl)-7-methyl-isoxazolo[5,4-c]pyridine-5-carbonyl]-amino}-acetic acid, {[3-(2,4-Dichloro-phenyl)-4-hydroxy-isoxazolo[5,4-c]pyridine-5-carbonyl]-amino}-acetic acid, and {[4-Hydroxy-3-(4-methanesulfonyl-phenyl)-isoxazolo[5,4-c]pyridine-5-carbonyl]-amino}-acetic acid.

20. A pharmaceutical composition comprising one or more compounds of claim 1 and a pharmaceutically acceptable excipient.

21. The composition of claim 20 further comprising at least one additional therapeutic agent selected from the group consisting of vitamin $B_{12}$, folic acid, ferrous sulfate, recombinant human erythropoietin, and an erythropoiesis stimulating agent (ESA).

22. A method of treating, pretreating, or delaying onset or progression of a condition mediated at least in part by hypoxia inducible factor (HIF), the method comprising administering to a patient a therapeutically effective amount of a composition of claim 20.

23. The method of claim 22, wherein the condition mediated, at least in part, by HIF is tissue damage associated with ischemia or hypoxia.

24. The method of claim 23, wherein the ischemia is associated with an acute event selected from the group consisting of myocardial infarction, pulmonary embolism, intestinal infarction, chronic kidney failure, ischemic stroke, and renal ischemic-reperfusion injury.

25. The method of claim 23, wherein the ischemia is associated with a chronic event selected from the group consisting of cardiac cirrhosis, transient ischemic attack, macular degeneration, peripheral artery disease, and congestive heart failure.

26. A method of treating, pretreating, or delaying onset or progression of a condition mediated at least in part by erythropoietin (EPO), the method comprising administering to a patient a therapeutically effective amount of a composition of claim 20.

27. A method of treating, pretreating, or delaying onset or progression of anemia, the method comprising administering to a patient a therapeutically effective amount of a composition of claim 20.

28. A method of inhibiting the activity of a HIF hydroxylase enzyme, the method comprising bringing into contact the HIF hydroxylase enzyme and an inhibitory-effective amount of a compound of claim 1.

29. The method of claim 28, wherein the HIF hydroxylase enzyme is an asparaginyl hydroxylase.

30. The method of claim 29, wherein the asparaginyl hydroxylase is a factor inhibiting HIF.

31. The method of claim 28, wherein the HIF hydroxylase enzyme is a prolyl hydroxylase.

32. The method of claim 31, wherein the prolyl hydroxylase is selected from the group consisting of human EGLN1, EGLN2, and EGLN3.

* * * * *